(12) United States Patent
Keith

(10) Patent No.: US 7,084,267 B1
(45) Date of Patent: Aug. 1, 2006

(54) PROMOTER REGIONS OF THE MOUSE AND HUMAN TELOMERASE RNA COMPONENT GENES

(76) Inventor: William Nicol Keith, c/o CRC Dept. of Medical Oncology, University of Glasgow, CRC Beatson Laboratories, Garscube Estate, Switchback Road, Glasgow G61 1BD (GB)

(*) Notice: Subject to any disclaimer, the term of this patent is extended or adjusted under 35 U.S.C. 154(b) by 0 days.

(21) Appl. No.: 09/601,267

(22) PCT Filed: Jan. 29, 1999

(86) PCT No.: PCT/GB99/00308

§ 371 (c)(1), (2), (4) Date: Aug. 25, 2000

(87) PCT Pub. No.: WO99/38964

PCT Pub. Date: Aug. 5, 1999

(30) Foreign Application Priority Data

Jan. 29, 1998 (GB) ................................. 9801902.9

(51) Int. Cl.
C07H 21/04 (2006.01)

(52) U.S. Cl. .................. 536/24.1; 435/320.1; 536/23.1

(58) Field of Classification Search ............... 536/24.1, 536/24.2, 23.1; 435/6, 320.1, 325
See application file for complete search history.

(56) References Cited

U.S. PATENT DOCUMENTS 5,583,016 A * 12/1996 Villeponteau et al. ...... 435/91.3
6,054,575 A * 4/2000 Villeponteau et al. ... 536/24.31

FOREIGN PATENT DOCUMENTS

| WO | WO 95/06486 | 3/1995 |
| WO | WO 96/01614 | 1/1996 |
| WO | WO 96/01835 | 1/1996 |
| WO | WO 98/11207 | 3/1998 |

OTHER PUBLICATIONS

Hickley et al. The mouse telomerase RNA 5'-end lies just upstream of the telomerase template sequence. Nucleic acids Research. vol. 26, No. 2, pp. 532-536, Jan. 15, 1998.*
Zhao et al. Cloning and Characterization of human and mouse telomerase RNA gene promoter sequences. Oncogene, vol. 16, pp. 1345-1350, Mar. 12, 1998.*
Palmiter et al.; Cell Lineage Ablation in Transgenic Mice by Cell-Specific Expression of a Toxin Gene, *Cell*, 50:435-443 (1987).
Feng et al.; The RNA Component of Human Telomerase, *Science*, 269:1236-1241 (1995).
Ring et al.; Suicide Gene Expression Induced in Tumour Cells Transduced with Recombinant Adenoviral, Retroviral and Plasmid Vectors Containing the ERBB2 Promoter, *Gene Therapy*, 3:1094-1103 (1996).
Hinkley et al.; The Mouse Telomerase RNA 5'-End Lies Just Upstream of the Telomerase Template Sequence, *Nucleic Acids Research*, 26(2):532-536 (1998).
Parkinson et al.; The Genetic Basis of Human Keratinocyte Immortalisation in Squamous Cell Carcinoma Development: the Role of Telomerase Reactivation, *European J. of Cancer*, 33(5):727-734 (1997.)
Landberg et al.; Telomerase Activity is Associated with Cell Cycle Deregulation in Human Breast Cancer, *Cancer Research*, 57:549-554 (1997).
I. Hart; Tissue Specific Promoters in Targeting Systemically Delivered Gene Therapy, *Seminars in Oncology*, 23(1):154-158 (1996).
Harley et al.; Telomerase, Checkpoints and Cancer, *Cancer Surveys*, 29:263-284 (1997).
C. Greider; Telomere Length Regulation, *Annu. Rev. Biochem.*, 65:337-365 (1996).
Zhao et al.; Cloning and Characterization of Human and Mouse Telomerase RNA Gene Promoter Sequences, *Oncogene*, 16:1345-1350 (1998).
McKie et al.; The Primitive Protozoon Trichomonas Vaginalis Contains Two Methionine γ-Lyase Genes That Encode Members of the γ-Family of Pyridoxal 5'-Phosphate-dependent Enzymes, *T. Journal of Biological Chemistry*, 273(10):5549-5556 (1998).

* cited by examiner

Primary Examiner—Kenneth R. Horlick
Assistant Examiner—Christopher M. Babic
(74) Attorney, Agent, or Firm—Dann Dorfman Herrell and Skillman; Kathleen D. Rigaut

(57) ABSTRACT

The present invention relates to the identification of the genomic promoter region of the human and mouse telomerase RNA gene. Telomerase activity is necessary for the unrestricted proliferative capacity of many human cancers. It is proposed that mutation or dysregulation of the telomerase repression pathway may cause reactivation or upregulation of telomerase expression in cancer. The invention provides details of elements important for the regulation of telomerase RNA genes, including the Sp family of transcription factors. There is further provided methods for screening elements having the ability for suppressing telomerase RNA gene promoter activity and use of such elements in the treatment of cancers. In addition, evidence is also provided for the development of new transcription based therapies for cancer and for genetic approaches to targeting therapeutic genes to cancer cells. Namely, (1) transcriptional repression and the disruption of signal transduction pathways regulating telomerase activation. (2) Tumour specific gene expression for genetic therapy via telomerase RNA gene promoters.

20 Claims, 29 Drawing Sheets

```
   1 agctactcag gaggctgaga cacgagaatc gcttgaaccc gggaggcaga ggttgcagtg
  61 agccgagatc acgccactag actccatcca gctgggcgca aagagcaaga ctccgtctca
 121 aaaaaaaaaa tcgttacaat ttatgtgga  ttactcccct cttttacct  catcaagaca
 181 cagcactact ttaaagcaaa gtcaatgatt gaaacgcctt tctttcctaa taaagggag
 241 attcagtcct taagattaat aatgtagtag ttacacttga ttaaagccat cctctgctca
 301 aggagaagct ggagaaggca ttctaaggaa aaagggcag  ggttgaact  cggacgcatc
 361 ccactgagcc gagacaagat tctgctgtag tcagtgctgc ctggaatct  attttcacaa
 421 agttctccaa aaaatgtgat gatcaaaact aggaattagt gttctgtgtc ttaggccta
 481 aaatcttcct gtgaattcca tttttaaggt agtcgagtg  aaccgcgtct ggtctgcaga
 541 ggatagaaaa aagccctct  gatacctcaa gttagtttca cctttaaaga agtcggaag
 601 taaagacgca agccttttcc cgacgtgcg  gaaggcaac  gtccttcctc atggccggaa
 661 atggaacttt aatttcccgt tccccccaac cagcccgcc  gagagagtga ctctcacgag
 721 agccgcgaga gtcagcttgg ccaatccgtg cggtcggcgg ccgctccctt tataagccga
 781 ctcgcccggc agcgcaccgg gttgcggagg gtgggcctgg gagggtggt  ggccatttt
 841 tgtctaaccc taactgagaa gggcgtaggc gccgtgcttt tgctcccgc  gcgctgtttt
 901 tctcgctgac tttcagcggg cggaaaagcc tcggcctgcc gccttccacc gttcattcta
 961 gagcaaacaa aaaatgtcag ctgctggccc gttcgccct  cccggggacc tgcggcgggt
1021 cgcctgccca gccccgaac  cccgcctga  ggccgcggtc ggccggggc  ttctccggag
1081 gcacctactg ccaccgcgaa gagttggctc tgtcagccgc gggtctctcg gggggcgaggg
1141 cgagttcag  gcctttcagg ccgcaggaag aggaacggag cgagtcccg  cgcgcgggcgc
1201 gattcctga  gctgtgggac gtgcacccag gactcggctc acacatgcag ttcgctttcc
1261 tgtttggtggg gggaacgccg atcgtgcgca tccgtcaccc ctcgccggca gtggggcttt
1321 gtgaaccccc aaacctgact gactgggcca gtgtgctgca aattgcagg  agacgtgaag
1381 gcacctccaa agtcggccaa aatgaatggg cagtgagccg ggttgcctg  gagccgttcc
1441 tgcgtgggtt ctccgtctt  ccgcttttg  ttgccttta  tggtttgtatt acaacttagt
1501 tcctgctctg cagattttgt tgaggtttt  gcttctccca agtagatct  cgaccagtcc
1561 cctcaacggg gtgtgggaga acagtcattt tttttttgaga gatcatttaa catttaatga
1621 atatttaatt agaagatcta aatgaacatt ggaaattgtg ttcctttaat ggtcatcggt
1681 ttatgccaga ggttagaagt ttcttttttg aaaaattaga ccttggcgat gacctgagc
1741 agtaggatat aaccccccaca agctt
```

*Fig. 1*

```
   1 aagcttggac ttgacaaaga aactgcagat catctggacc cccccccccc cccatttagg
  61 tttaacaatg taccagctat ctgacttaag caaactgtgt tcctcataga taaggcggga
 121 ctgctcatgg tcattgtgaa gttcagttgg gataaacaaa ttttaaggtg cataacaaaa
 181 aacacaaaat gttggtgttt gtttaaaaaa aactaaagaa tttctggagg caggcagtta
 241 cagaaaacat gctgatattc tgagttgcct gctagttggt gccattccac cagagtgaac
 301 acatctctgt tgaccctgat tttctgtagg tctgtctgtg tgtctgtcct ttctccagca
 361 agggctgacc ctaatcgggg tcccaggacc caagccttga gaaaggcagt agtatgtcat
 421 ctagttgaaa tgacacattc tctacagtgt ccaaatgaca tctttgtgct agacagaaca
 481 tttttattgga tggactatgg ctgaccactt ggcttggggg ggggggggaag gggccgccaa
 541 gggcgggggt ccctcatttg cttgttatta acacttgctt gtttgtttac ttgttagtag
 601 gaatctgctc taccacgtgg gttctacatg gttccacagg ggtcacctgg tccgttttttg
 661 ttttctggga cagttttcac aaatgttgtc tagactccac gttggctttg aagcctacag
 721 ctatgagcct ctgtgccagt ttatgcagta gtatctctcg ggttgtcctt caccgttagt
 781 agtggtgctc ttagaaggca ccgtgatttt ttgctttcca tctctttccc ctgccatgcc
 841 ttctgtggtt ctctgccagg caccaaactg ttcagaaact ctccagcccg gtagagaacg
 901 gtaggggaa agaactgacg tgtggaaggg atgggcaggg agaagaggca ccgaactcgg
 961 tcttaaacaa aaaaaaaaaa aaaggagca ttagaaaaaa aaacaaattt gtgaccttga
1021 actacagacc tcctgcctca gcctcctaca agctgggatt ataggctcgg gtcagctacc
1081 cttgaaatct ttttctttct ggaactcagt acctggttgg ccatgcactc acaagagatc
1141 cgcctgcctt ctgtctctca aattctggaa ttaaagattt gcgccacttt tccccacttc
1201 cacccccggc tgtgggagtg gactgggttg aaggtggaat ttttttttttt tttttttttt
1261 tttagtgaaa aaaggggggga ttggaaatat ccctacttttc aactctagta tatttcagaa
1321 accaagcctc agagatgtgc gtgcgtgcgt gtgtgtgtgt gtatgtgtgt gtgtctcaca
1381 gcaagaaaca gattttatta tttatttttt atttatttat ttttgcaag tgactggcta
1441 ggaagagtgg ggaagcggga ggacaaatgg ggaagaggga gcatttccgc aagtgctggg
1501 ctcgaccaat cagcgcgcgc catggggtat ttaaggtcga gggcggctag gcctcggcac
1561 ctaaccctga ttttcattag ctgtgggttc tggtctttttg ttctccgccc gctgttttttc
1621 tcgctgactt ccagcgggcc aggaaagtcc agacctgcag cgggccaccg cgcgttcccg
1681 agcctcaaaa acaaacgtca gcgcaggagc tccaggttcg ccgggagctc cgcggcgccg
1741 ggccgccag tcccgtaccc gcctacaggc cgcggccggc ctgggtctt aggactccgc
1801 tgccgccgcg aagagctcgc ctctgtcagc cgcggggcgc cggggctgg ggccaggccg
1861 ggcgagcgcc gcgaaggaca ggaatggaac tggtccccgt gttcggtgtc ttacctgagc
1921 tgtgggaagt gcaccggaa ctcggttctc acaaccccca ttcccgctgg ggaaatgccc
1981 cgctgcaggg cgggccgcta gaacctgcga cttctgggga aagggcttc ggtgtgagac
2041 ggtagccagc caaagggtat atatcgccct cacgcccgt ccccctccac ttttgtctaa
2101 tactcctgtt tctgttgtgc agattttgca ggcgtttcgc tggctctgcc tgaacgagct
2161 atgcagccat gtggtccttg ggggtggggg tggggatggg aggactacag gcgtagatct
2221 tcatactggg tttgtgtagt gctgggaatt gaacctagtt tcctaagttc tctatcaact
```

*Fig. 2*

```
2281 ggtattccca ttgtatggga gattttttt  ttcttttgta tatggggggcg ttgaacattt
2341 tgtaaacaat tagaaaatct agtagttttt taatgaaaat gttcactttt ctttgtcttt
2401 gggatgcaaa acattacatt gaagctgaga agtttaaaga tgcgtgtctt cccctgccta
2461 ccttcgcgtt cacacagaac ctgttatctt ttcagaaaag aaaatgagat aggcagggtg
2521 gatctggagt ttcaaggccc ttgcctggtc tgcagagtga gttaggccac accagaaaag
2581 tatgtgtcaa aaacaaagaa gaaaggcttt gtgggggggtg gggtagcaaa cgatcttaat
2641 cccctgtgct tgggaggccc gcaagggggga tatctgtgaa ggagacaaac aaagctacac
2701 tgtgtggtaa acaaaaaacg aggaggagga gcaagaagaa tatgagagcc cacggaagga
2761 agagtatcag tccccaggcc accagttcct cagggggtaac tatgtttgtg agtgtctcgg
2821 tgccttgact tcctcagtac ttttctgggt tttagtcata aaaaacattg aagagatgaa
2881 gaagtgtatg tttagtaagt acataccaaa agtttgtgag ctatatgcat atagcaactc
2941 agtcacctga aacaggcccc ttgcagctaa catatttctt agtattacta ttataaagac
3001 tagggggagtt tctaagccgg cactccttac aagggacgaa gccatgttca gctccagctt
3061 gccaagattc tgaaacccaa cgtcaagcct gacgagttcg agcctggcat ctctcagccg
3121 ctgctcgagc tggagatgac cacggatctc aaggcacagc tgtgggaact caacatcacc
3181 gaagccaagg aaaattgaag ttggtggtgg tcagaaggct gttataattt ttgtaccagt
3241 tcctcagctt aaatctttcc agaaaatcca agtctggcta gtttgtgaat tggagaaaaa
3301 gttcagcgga aagcacgtgt cttcattgct cagaagagga tctgtccaag ccaaccagga
3361 aaagctgtac gaaaaataag ccaaagcacc ctagaagctg caccctgaca gcagtgcatg
3421 tcttctcaag tgaaattgtg ggaaagagga tccatccgtg tgaaactgga tggcaatctg
3481 gagcaggttc atcttcctct ctggtacatc ccatgtctcc tcatctccat cctcccctct
3541 gcctctgtgt ctcatctcta aaactctcag cccatcttcc tttaccactg cccaatcaca
3601 ggctctagcc ttacctttca cctgccctca cctgcttata gacagcaatc tacatttctc
3661 ccttttgtc  caattaaaag actcttttct ctcggatata aaatgagcac aactattatt
3721 accattctgt aatttataaa gtatagatag acctaacacc cagtctatca ttttgacagt
3781 taaataaagc attctgcaat cctatcctaa ctttaaaagg cttataattc tacacttgtt
3841 atgtcctggt tcagcttgta tattagaaaa ccatctcaaa ttatatatat atatatatta
3901 cacacacaca tatgtatata tacatatata tgtatacaca cacacacata tatatatgta
3961 tatgtatgta tgtatgtata tatatatact tttaatgcta aatagcctgg gttggctaag
4021 actacttcaa tcctgccaga attc
```

*Fig. 2 (cont)*

```
         ┌hProm867
-798     └agctactcaggaggctgagacacgagaatcgcttgaacccgggaggcaga -748     ggttgcagtgagccgagatcacgccactagactccatccagcctgggcga
                 Zeste
-698     aagagcaagactccgtctcaaaaaaaaaaatcgttacaatttatggtgga
                                      ┌hProm697
-648     ttactcccctcttttacctcatcaagacacagcactactttaaagcaaa
                                        GR
-598     gtcaatgattgaaacgcctttctttcctaataaaagggagattcagtcct
              cMYB            NF1 PEA3
-548     taagattaataatgtagtagttacacttgattaaagccatcctctgctca
             AFP1/BRN2
-498     aggagaagctggagaaggcattctaaggaaaaaggggcagggttggaact
                                  PEA3/c-Ets-2 Sp1/NF-E2 cMYB
            ┌hProm505
-448     cggacgcatccc└actgagccgagacaagattctgctgtagtcagtgctgc
                   Zeste                              GCN4/AP1
-398     ctgggaatctattttcacaaagttctccaaaaatgtgatgatcaaaact
         myogenin            GR              GR
-348     aggaattagtgttctgtgtcttaggccctaaaatcttcctgtgaattca
                GR/PR/AR        F2F/Pit-1a            Pit-1a
                                ┌hProm341
-298     tttttaaggtagtcgaggtgaaccgcgtctggtctgcagaggatagaaaa
                                                      GATA-1
-248     aaggccctctgatacctcaagttagtttcacctttaaagaaggtcggaag
                                                      E1A-F
-198     taaagacgcaaagcctttcccggacgtgcggaagggcaacgtccttcctc
                 NF1                                  PEA3  PU.1
-148     atggccggaaatggaactttaatttcccgttcccccaaccagcccgccc
                                                          Sp1
-98      gagagagtgactctcacgagagccgcgagagtcagcttggccaatccgtg
               AP1                GCN4/AP1     CCAAT Box ┌▶
            ┌hProm111
-48      cggtcggcggccgctcccttataagccgactcgcccggcagcgcaccgg
         PEA2/PEBP2      GAGA    TBP/TFIID
         gttgcggagggtgggcctgggaggggtggtggccattttttgtctaaccc
                                                     template
         taactgagaagggcgta┌hProm
```

Fig. 4A

```
         ┌mProm628
-514     tgtgaccttgaactacagacctcctgcctcagcctcctacaagctgggat
             PPAR/ELP    GR -464     tataggctcgggtcagctaccttgaaatcttttctttctggaactcag
                                 H4TF-1

-414     tacctggttggccatgcactcacaagagatccgcctgccttctgtctctc
                       AP1/GCN4/Zeste        SP-1
                            ┌mProm458
-364     aaattctggaattaaagatttgcgccacttttcccc acttccaccccgg
                             C/EBPalpha, beta    AP-2
              ┌mProm418
-314     ctgtgggagtggactgggttgaaggtggaatttttttttttttttttt
              p300

-264     ttttagtgaaaaaggggggattggaaatatccctactttcaactctagt
                                 CP1

-214     atatttcagaaaccaagcctcagagatgtgcgtgcgtgcgtgtgtgtgtg
                        ┌mProm267
-164     tgtatgtgtgtgtgtctcacagcaagaaacagattttattatttatttt
                   GR                         F2F/Pit-1a
                              ┌mProm208
-114     tatttatttatttttgcaagtgactggataggaagagtggggaagcggg
                      IRF-1,2   GCN4/AP1       AP-2  c-ETS-2
                                                         ┌mProm136
-64      aggacaaatggggaagagggagcatttccgcaagtgctgggctcgaccaa
           GR    AP-2 c-ETS-2                   AP-2   CCAAT Box/AP-1

-14      tcagcgcgcgccatggggtatttaaggtcgagggcggctaggcctcggca cctaaccctgattttcattagctgtgggttctggtcttttgttctccgcc
         template                     ┌mProm
         cgctgttttctcgctgacttccagcgg
```

Fig. 4B

Oligo's Used: human

| Name | Sequence | Comments |
|---|---|---|
| hTR5 | TACGCCCTTCTCAGTTAGGGTTAG | |
| hTR14 | GGATCCTACGCCCTTCTCAGTTAGGGTTAG | hTR5 with BamHI site |
| hTR13F | ACTGAGCCGAGACAAGATTC | |
| hTR17F | GGATCCACTGAGCCGAGACAAGATTC | hTR13F with BamHI site |
| hTR10F | AGCTACTCAGGAGGCTGAGA | |
| hTR20F | GCGCTCGAGAGCTACTCAGGAGGCTGAGA | hTR10F with XhoI site plus gcg clamp |
| hTR11F | CATCAAGACACAGCACTACT | |
| hTR21F | GCGCTCGAGCATCAAGACACAGCACTACT | hTR11F with XhoI site plus gcg clamp |
| hTR6F | GTCTGGTCTGCAGAGGATAG | |
| hTR22F | GCGCTCGAGGTCTGGTCTGCAGAGGATAG | hTR6F with Xho site plus gcg clamp |
| hTR5 | TACGCCCTTCTCAGTTAGGGTTAG | |
| hTR23R | CGCAAGCTTTACGCCCTTCTCAGTTAGGGTTAG | hTR5 with HindIII site plus cgc clamp |
| hTRe | CTGAGCTGTGGGACGTGCAC | |
| hTRf | AGACGGGAGAACCCACGCAG | |
| hTRg | CTCGGCTCACACATGCAGTT | |
| hTRh | TCTGCAGAGCAGGAACTAAGT | |
| TRC3F | CTAACCCTAACTGAGAAGGGCGTA | |
| TRC3R | GGCGAACGGGCCAGCAGCTGACATT | |

Oligo's Used: Mouse

| Name | Sequence | Comments |
|---|---|---|
| mTR16F | GTGTCTCACAGCAAGAAACA | |
| mtr25f | GCGCTCGAGGTGTCTCACAGCAAGAAACA | This is mtr16f with XhoI site plus gcg clamp |
| mTR17F | GTGACTGGCTAGGAAGAGTG | |
| mtr26f | GCGCTCGAGGTGACTGGCTAGGAAGAGTG | This is mtr17f with XhoI site plus gcg clamp |
| mTR18F | TGTGACCTTGAACTACAGAC | |
| mtr27f | GCGCTCGAGTGTGACCTTGAACTACAGAC | This is mtr18f with XhoI site plus gcg clamp |
| mTR19F | GGACTGGGTTGAAGGTGGAA | |
| mtr28f | GCGCTCGAGGGACTGGGTTGAAGGTGGAA | This is mtr19f with XhoI site plus gcg clamp |
| mTR20F | TGCGCCACTTTTCCCCACTT | |
| mtr29f | GCGCTCGAGTGCGCCACTTTTCCCCACTT | This is mtr20f with XhoI site plus gcg clamp |
| mTRr1 | CCGCTGGAAGTCAGCGAGAA | |
| mtr30r | CGCAAGCTTCCGCTGGAAGTCAGCGAGAA | This is mTRr1 with HindIII site plus cgc clamp |
| mTR36F | GCGCTCGAGTCGACCAATCAGCGCGCGCCAT | This is Xho I site PCR primer plus gcg clamp |
| mTRr1 | CCGCTGGAAGTCAGCGAGAA | |
| mTRf1 | TCGACCAATCAGCGCGCGCCAT | |

*Fig. 6*

```
TTGTGACCTTGAACTACAGAGACCTCCTGCCTCAGCCTCCTACAAGCTGGGATTATAGGCTCGGGTCAGCTACCCTTGAAA
TTCTTTTTCTTTCTGGAACTCAGTCAGTTGGCCATGCACTCACAAGAGATCCGCCTGCCTTCTGTCAAATTCTGGA
ATTAAAGATTGCGCCACTTTTCCCCACTTCCACTTCCACCCCGGCTGTGGGACTGGGTTGAAGGTGGAATTTTTTTT
TTTTTTTTAGTGAAAAAAGGGGGATTGGAAATATCCCTCAACTCTAGTATATTCAGAAACCAAGCCTCAG
AAATGCGCGTGCGTGCGTGTGTGTATGTGTGTCTCACAGCAAGAAACAGATTTTATTATTTATTTTTA
TTTATTATTTTTGCAAGTGACTGGCTAGGAAGAGTGGGAGCGGGAGGAAGCGGGAAGAGGAGCATTCCGC
AAGTGCTGGGCTCGACCAATCAGCGCGCGCCATGGGGTATTAAGGTCGAGGGCGGCTAGGCCTCGGCACCTAACCCTG
ATTTTCATTAGCTGTGGGTTCTGGTCTTTCGTCTTTCCGTTCTCCCGCCCGCTGTTTTTCGCTGACTTCCAGCGGA
```

*Fig. 9*

2923 (wt)  -107 Sp1-2                                              CCAAT-box
           AGCCCGCCCGAGAGAGTGACTCTCACGAGAGCCGCGAGAGTCAGCTTGGCCAA -55

2923 (wt)  -54
           TCCGTGCGGTCGGGCGGCCGCTCCCTTTATAAGCCGACTCGCCCGGCAGCGCACC -1
                                              Sp1-1
           +1                                                            +52
           GGGTTGCGGGAGGCCTGGGGTGGGGTGCGGGAGGGGTGGTGGCCATTTTTGTCTAACC
                                     RCE              Sp1-4

+53           +69
           CTAACTGAGAAGGGCGTA

*Fig. 11*

| Oligonucleotide | Position | Sequence* | Purpose |
|---|---|---|---|
| h11[a] | -2 to +36 | CCGGGTTGCCGGAGGGTGGGCCTGGGAGGGGTGGTGGCC | RCE(+12,+16 and +30, +34) and Sp1.4 binding site |
| h111[a] | " | CCGGGTTGCCGGAAAATGGGCCTGGGAGGGGTGGTGCC | RCE1 mutation from ggg to aaa (+11/+13,) |
| h112[a] | " | CCGGGTTGCCGGAGGGTGGGCCTGGGTAAGGTGGTGCC | Sp1.4 mutation from agg to taa (+24/+26) |
| h113[a] | " | CCGGGTTGCCGGAAAATGGGCCTGGGTAAGGTGGTGCC | Mutant of both RCE1 and Sp1.4 binding site(+11/+13, +24/+26) |
| h11c[a] | -2 to +23 | CCGGGTTGCCGGAGGGTGGGCCTGGG | RCE1 binding site |
| h11d[a] | +14 to +36 | GCTGGGAGGGGTGGTGCC | Sp1.4 or RCE2 binding site |
| h111a[a,b] | " | CCGGGTTGCCGGAAAATGGGCCTGGG | RCE1 mutation from ggg to aaa(+11/+13) |
| h112b[a,b] | +15 to +36 | GGGCCTGGGTAAGGTGGTGCC | Sp1.4 mutation from agg to taa |
| h112c[a,b] | " | GGGCCTGGGTAAGGTAATGGCC | Sp1.4 and RCE2 mutant from agggtgg to taaggtaa(+24/+26, +30/+31) |
| h11e[a] | " | GGGCCTGGGAGGGGTAATGGCC | RCE2 mutant from gg to (+30/+31) |
| h10[a] | -63 to -42 | CTTGGCCAATCCGTCGCGGTCGG | h10 footprinting region containing CCAAT binding site |
| h101[a] | -63 to -42 | CTTGGAGTCTCCGTGCGGTCGG | CCAAT motif mutation from ccaa to agtc, (-58/-55) |
| h10m11[b] | -74 to -45 | GCGAGAGTCAGCTTGGAGTCTCCGTGCGG | CCAAT motif mutation from ccaa to agtc, (-58/-55) |
| h10m2[a,b] | -63 to -42 | CTTGGCCAATCCTGATGGTCGG | h10 mutation from gtgc to tgat, (-51/-47) |
| h9[a] | -44 to -17 | CGGCGGCCGCTCCCTTCCTTTATAAGCCGACT | h9 footprinting region containing SP1.1 binding site |
| h91[a] | -44 to -21 | CTTACGCCGCTCCCTTTATAAGCC | h9 mutation from gggcg to ttac, (-43/-40) |
| h910[b] | -53 to -29 | CCGTCCGGTCTTACGCCCGCTCCC | h9 mutation from gggcg to ttac, (-43/-40) |
| h911[b] | -44 to -21 | CGGCGTAAACTCCCTTTATAAGCC | h9 mutation from gccg to taaa, (-39/-36) |
| h92[a] | -44 to -21 | CGGCGGCCATAGCCTTTATAAGCC | h9 mutation from gctc to atag, (-36/-33) |
| h921[a] | -44 to -21 | CGGCGGCCGCTCATGCTATAAGCC | h9 mutation from cctt to atgc, (-32/-29) |
| h93[a] | -44 to -21 | CGGCGGCCGCTCCCTTCGACAGCC | h9 mutation from tata to cgac, (-28/-25) |
| h930[b] | -38 to -14 | CCGCTCCCTTCGACAGCCGACTCGC | h9 mutation from tata to cgac, (-28/-25) |
| h4[a] | -110 to -91 | ACCAGCCCGCCGAGAGAGT | h4 footprinting region containing SP1.2 binding site |
| h41m[a] | -110 to -91 | ACCAGCCCGAACGAGAGAGT | Sp1.2 mutation from cc to aa, (-101/-100) |
| h5[a] | -471 to -452 | GAAAAAGGGCAGGGTTGGA | SP1.3 binding site |
| h5m[a] | -471 to -452 | GAAAAAGGTTCAGGGTTGGA | Sp1.3 mutation from gg to tt, (-463/-462) |

\* Nucleotides corresponding to promoter sequences are given in uppercase letters from 5' end to 3' end; specific nucleotides mentioned in Purpose colum are undetlined. Highlight indicate mutagenesis nucleotide.
[a] Complementary lowerstrand sequence for EMSA not show.
[b] For PCR-directed in vitro mutagenesis, complementary lowstrand sequence not shown.

*Fig. 12*

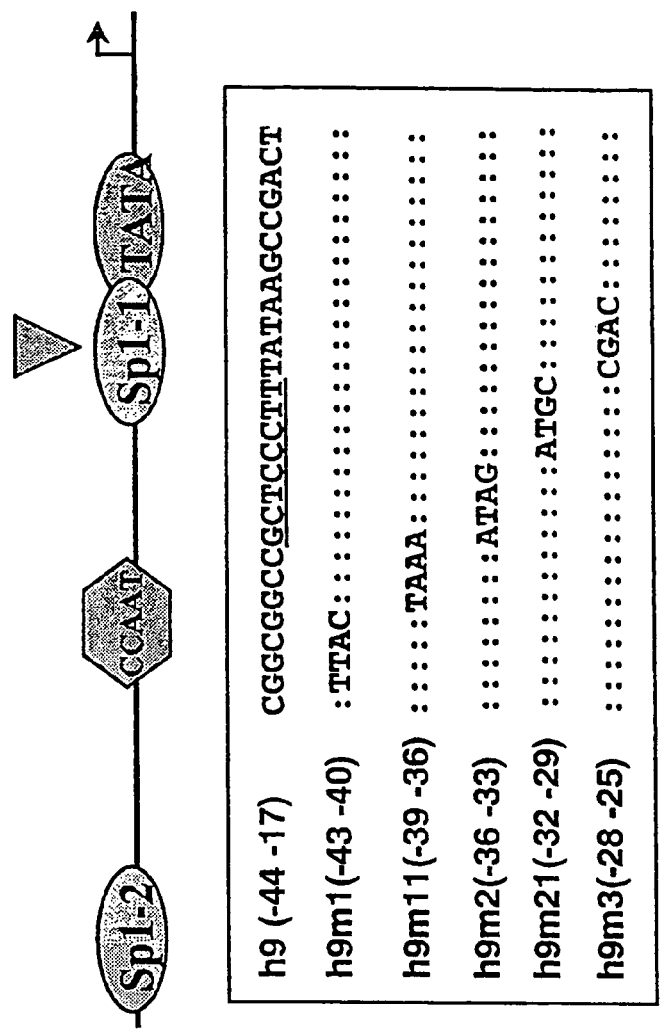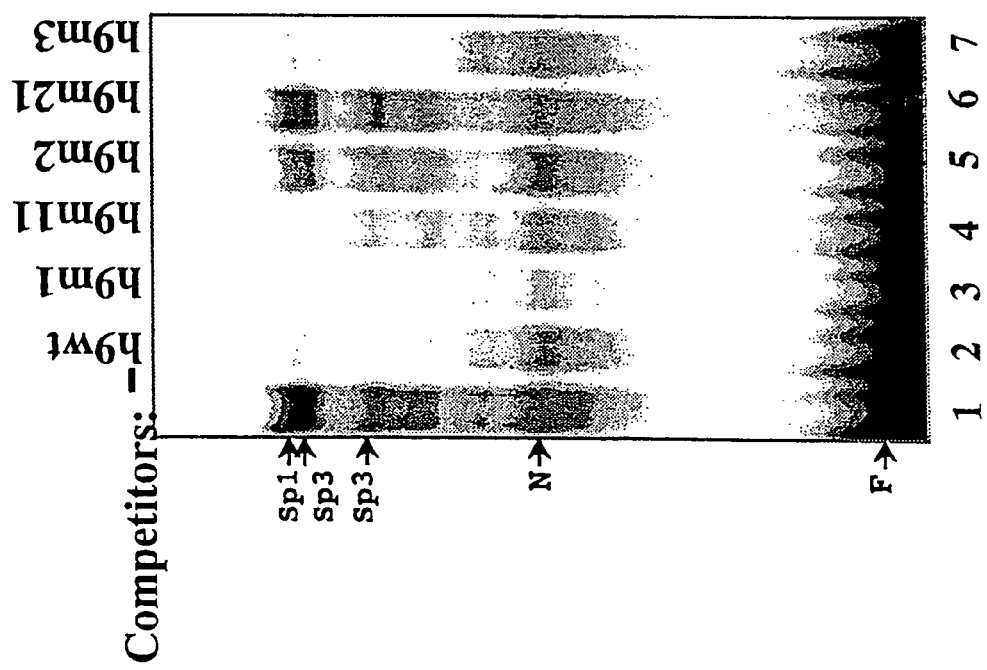
Fig. 16

- Gel shift assays identify DNA/protein binding activity
- Do mutation of these binding sites influence the promoter activity?
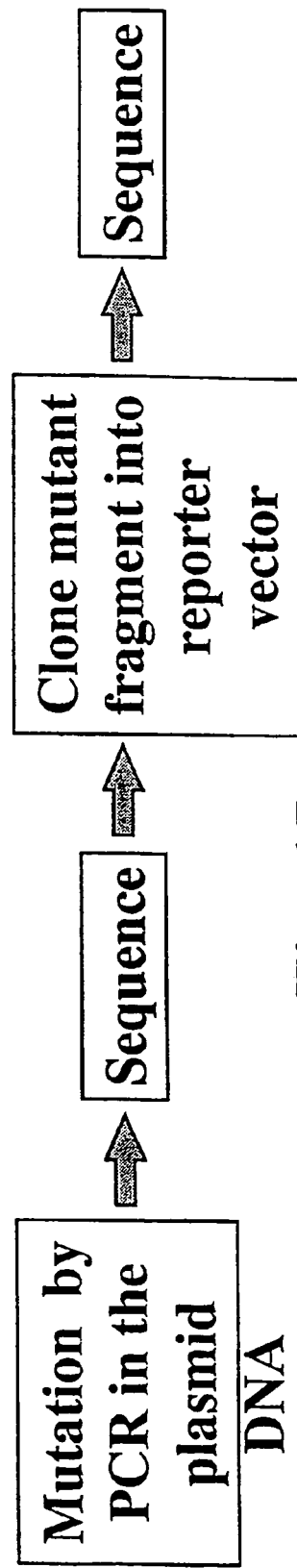
Fig. 17

```
                      -107                                                       -55
2923(-107 +69)    AGCCCGCCCGAGAGAGTGACTCTCACGAGAGCCGCGAGAGTCAGCTTGGCCAA
29m23(mSp1.2)     ------AA--------------------------------------------
1011              ------------------------------------------------AGTC
29m292(mSp1-1,2)  ------AA--------------------------------------------
29m921(mSp1-1,2)  ------AA--------------------------------------------

-54                                                             -1
2923(-107 +69)    TCCGTGCGGTCGGCGGCCGCTCCCTTTATAAGCCGACTCGCCCGGCAGCGCACC
102               ---TGAT-----------------------------------------------
910               ------------TTAC--------------------------------------
911               ----------------TAAA----------------------------------
92(mSp1.1)        ----------------ATAG----------------------------------
29m292(mSp1-1,2)  ----------------ATAG----------------------------------
921(mSp1.1)       ------------------ATGC--------------------------------
29m921(mSp1-1,2)  ------------------ATGC--------------------------------
930(mTATA)        -----------------------CGAC---------------------------
26n23(-51 +69)    ------------------------------------------------------

+1                                                            +53
26n23(-51 +69)    GGGTTGCGGAGGGTGGGCCTGGGAGGGGTGGTGGCCATTTTTTGTCTAACC
29111(mRCE)       -------AAA-----------------------------------------
29112(mSp1.4)     ---------------------TAA---------------------------
111(Sp1.4)*       --//-//---AAA--------------------------------------
112(RCE)*         --//-//--------------TAA---------------------------
113(mSP1+mRCE)*   --//-//---AAA--------TAA---------------------------
115*              --//-//--------------TAA---AA----------------------
114*              --//-//---AAA--------TAA---AA----------------------

+54            +69
                  CTAACTGAGAAGGGCGTA
```

\* Double mutagenesis by using pLh29m292 as template.

*Fig. 19*

SEQUENCE LISTING

<160> NUMBER OF SEQ ID NOS: 86

<210> SEQ ID NO 1
<211> LENGTH: 1765
<212> TYPE: DNA
<213> ORGANISM: Homo sapiens

<400> SEQUENCE: 1

```
agctactcag gaggctgaga cacgagaatc gcttgaaccc gggaggcaga ggttgcagtg      60
agccgagatc acgccactag actccatcca gcctgggcga aagagcaaga ctccgtctca     120
aaaaaaaaaa tcgttacaat ttatggtgga ttactcccct cttttttacct catcaagaca    180 cagcactact ttaaagcaaa gtcaatgatt gaaacgcctt tctttcctaa taaaagggag     240
attcagtcct taagattaat aatgtagtag ttacacttga ttaaagccat cctctgctca     300
aggagaagct ggagaaggca ttctaaggaa aaaggggcag ggttggaact cggacgcatc     360
ccactgagcc gagacaagat tctgctgtag tcagtgctgc ctgggaatct attttcacaa     420
agttctccaa aaaatgtgat gatcaaaact aggaattagt gttctgtgtc ttaggcccta     480
aaatcttcct gtgaattcca tttttaaggt agtcgaggtg aaccgcgtct ggtctgcaga     540
ggatagaaaa aaggccctct gatacctcaa gttagtttca cctttaaaga aggtcggaag     600
taaagacgca aagcctttcc cggacgtgcg gaagggcaac gtccttcctc atggccggaa    660
atggaacttt aatttcccgt tccccccaac cagcccgccc gagagagtga ctctcacgag    720
agccgcgaga gtcagcttgg ccaatccgtg cggtcggcgg ccgctcccttt ataagccga    780 ctcgcccggc agcgcaccgg gttgcggagg gtgggcctgg gagggtggt ggccattttt   840
```

-continued

```
tgtctaaccc taactgagaa gggcgtaggc gccgtgcttt tgctcccgc gcgctgtttt      900
tctcgctgac tttcagcggg cggaaaagcc tcggcctgcc gccttccacc gttcattcta    960
gagcaaacaa aaaatgtcag ctgctggccc gttcgcccct cccggggacc tgcggcgggt   1020
cgcctgccca gccccgaac cccgcctgga ggccgcggtc ggcccggggc ttctccggag    1080
gcacctactg ccaccgcgaa gagttggctc tgtcagccgc gggtctctcg ggggcgaggg   1140
cgaggttcag gcctttcagg ccgcaggaag aggaacggag cgagtccccg cgcgcggcgc   1200
gattccctga gctgtgggac gtgcacccag gactcggctc acacatgcag ttcgctttcc   1260
tgttggtggg gggaacgccg atcgtgcgca tccgtcaccc ctcgccggca gtgggggctt   1320
gtgaaccccc aaacctgact gactgggcca gtgtgctgca aattggcagg agacgtgaag   1380
gcacctccaa agtcggccaa atgaatgggg cagtgagccg gggttgcctg gagccgttcc   1440
tgcgtgggtt ctcccgtctt ccgcttttttg ttgccttttta tggttgtatt acaacttagt   1500
tcctgctctg cagattttgt tgaggttttt gcttctccca agtagatct cgaccagtcc    1560
cctcaacggg gtgtgggaga acagtcattt tttttttgaga gatcatttaa catttaatga   1620
atatttaatt agaagatcta aatgaacatt ggaaattgtg ttcctttaat ggtcatcggt    1680
ttatgccaga ggttagaagt ttctttttttg aaaaattaga ccttggcgat gaccttgagc   1740
agtaggatat aacccccaca agctt                                         1765
```

<210> SEQ ID NO 2
<211> LENGTH: 4044
<212> TYPE: DNA
<213> ORGANISM: Mus sp.

<400> SEQUENCE: 2

```
aagcttggac ttgacaaaga aactgcagat catctggacc ccccccccc cccatttagg      60
tttaacaatg taccagctat ctgacttaag caaactgtgt tcctcataga taaggcggga    120
ctgctcatgg tcattgtgaa gttcagttgg gataaacaaa ttttaaggtg cataacaaaa    180
aacacaaaat gttggtgttt gtttaaaaaa aactaaagaa tttctggagg caggcagtta    240
cagaaaacat gctgatattc tgagttgcct gctagttggt gccattccac cagagtgaac    300
acatctctgt tgaccctgat tttctgtagg tctgtctgtg tgtctgtcct ttctccagca    360
agggctgacc ctaatcgggg tcccaggacc caagccttga gaaaggcagt agtatgtcat    420
ctagttgaaa tgcacattc tctacagtgt ccaaatgaca tctttgtgct agacagaaca    480
ttttattgga tggactatgg ctgaccactt ggcttggggg gggggggaag gggccgccaa    540
gggcgggggt ccctcatttg cttgttatta acacttgctt gtttgtttac ttgttagtag    600
gaatctgctc taccacgtgg gttctacatg gttccacagg ggtcacctgg tccgtttttg    660
ttttctggga cagttttcac aaatgttgtc tagactccac gttggctttg aagcctacag    720
ctatgagcct ctgtgccagt ttatgcagta gtatctctcg ggttgtcctt caccgttagt    780
agtggtgctc ttagaaggca ccgtgatttt ttgctttcca tctctttccc ctgccatgcc    840
ttctgtggtt ctctgccagg caccaaactg ttcagaaact ctccagcccg gtagagaacg    900
gtaggggggaa agaactgacg tgtggaaggg atgggcaggg agaagaggca ccgaactcgg   960
tcttaaacaa aaaaaaaaaa aaaggagca ttagaaaaaa aaacaaattt gtgaccttga    1020
actacagacc tcctgcctca gcctcctaca agctgggatt ataggctcgg gtcagctacc   1080
cttgaaatct ttttctttct ggaactcagt acctggttgg ccatgcactc acaagagatc   1140
```

-continued

```
cgcctgcctt ctgtctctca aattctggaa ttaaagattt gcgccacttt tccccacttc    1200
cacccccggc tgtgggagtg gactgggttg aaggtggaat tttttttttt tttttttttt    1260
tttagtgaaa aaggggggga ttggaaatat ccctactttc aactctagta tatttcagaa    1320
accaagcctc agagatgtgc gtgcgtgcgt gtgtgtgtgt gtatgtgtgt gtgtctcaca    1380
gcaagaaaca gattttatta tttattttt atttatttat tttttgcaag tgactggcta     1440
ggaagagtgg ggaagcggga ggacaaatgg ggaagaggga gcatttccgc aagtgctggg    1500
ctcgaccaat cagcgcgcgc catgggtat ttaaggtcga gggcggctag gcctcggcac     1560
ctaaccctga ttttcattag ctgtgggttc tggtctttg ttctccgccc gctgtttttc     1620
tcgctgactt ccagcgggcc aggaaagtcc agacctgcag cgggccaccg cgcgttcccg    1680
agcctcaaaa acaaacgtca gcgcaggagc tccaggttcg ccgggagctc cgcggcgccg    1740
ggccgcccag tcccgtaccc gcctacaggc cgcggccggc ctgggtctt aggactccgc     1800 tgccgccgcg aagagctcgc ctctgtcagc gcgggggcgc cggggctgg ggccaggccg     1860 ggcgagcgcc gcgaaggaca ggaatggaac tggtccccgt gttcggtgtc ttacctgagc    1920
tgtgggaagt gcacccggaa ctcggttctc acaaccccca ttcccgctgg ggaaatgccc    1980
cgctgcaggg cgggccgcta gaacctgcga cttctgggga aaggggcttc ggtgtgagac    2040
ggtagccagc caagggtat atatcgccct cacgccccgt cccctccac ttttgtctaa      2100 tactcctgtt tctgttgtgc agattttgca ggcgtttcgc tggctctgcc tgaacgagct    2160
atgcagccat gtggtccttg ggggtggggg tgggatggg aggactacag gcgtagatct     2220
tcatactggg tttgtgtagt gctgggaatt gaacctagtt tcctaagttc tctatcaact    2280
ggtattccca ttgtatggga gatttttttt ttcttttgta tatgggggcg ttgaacattt    2340
tgtaaacaat tagaaaatct agtagttttt taatgaaaat gttcacttt ctttgtcttt     2400 gggatgcaaa acattacatt gaagctgaga agtttaaaga tgcgtgtctt cccctgccta    2460
ccttcgcgtt cacacagaac ctgttatctt ttcagaaaag aaaatgagat aggcagggtg    2520
gatctggagt tcaaggcccc ttgcctggtc tgcagagtga gttaggccac accagaaaag    2580
tatgtgtcaa aaacaaagaa gaaaggcttt gtgggggtg gggtagcaaa cgatcttaat     2640
cccctgtgct tgggaggccc gcaaggggga tatctgtgaa ggagacaaac aaagctacac    2700
tgtgtggtaa acaaaaaacg aggaggagga gcaagaagaa tatgagagcc cacggaagga    2760
agagtatcag tccccaggcc accagttcct caggggtaac tatgtttgtg agtgtctcgg    2820
tgccttgact tcctcagtac ttttctgggt tttagtcata aaaaacattg aagagatgaa    2880
gaagtgtatg tttagtaagt acataccaaa agtttgtgag ctatatgcat atagcaactc    2940
agtcacctga acaggcccc ttgcagctaa catatttctt agtattacta ttataaagac     3000
taggggagtt tctaagccgg cactccttac aagggacgaa gccatgttca gctccagctt    3060
gccaagattc tgaaacccaa cgtcaagcct gacgagttcg agcctggcat ctctcagccg    3120
ctgctcgagc tggagatgac cacggatctc aaggcacagc tgtgggaact caacatcacc    3180
gaagccaagg aaaattgaag ttggtggtgg tcagaaggct gttataattt ttgtaccagt    3240
tcctcagctt aaatctttcc agaaaatcca agtctggcta gtttgtgaat tggagaaaaa    3300
gttcagcgga aagcacgtgt cttcattgct cagaagagga tctgtccaag ccaaccagga    3360
aaagctgtac gaaaaataag ccaaagcacc ctagaagctg cacctgaca gcagtgcatg     3420 tcttctcaag tgaaattgtg ggaaagagga tccatccgtg tgaaactgga tggcaatctg    3480
gagcaggttc atcttcctct ctggtacatc ccatgtctcc tcatctccat cctcccctct    3540
```

-continued

```
gcctctgtgt ctcatctcta aaactctcag cccatcttcc tttaccactg cccaatcaca    3600
ggctctagcc ttaccttcca cctgccctca cctgcttata gacagcaatc tacatttctc    3660
cctttttgtc caattaaaag actcttttct ctcggatata aaatgagcac aactattatt    3720
accattctgt aatttataaa gtatagatag acctaacacc cagtctatca tttttgacagt   3780 taaataaagc attctgcaat cctatcctaa ctttaaaagg cttataattc tacacttgtt    3840
atgtcctggt tcagcttgta tattagaaaa ccatctcaaa ttatatatat atatatatta    3900
cacacacaca tatgtatata tacatatata tgtatacaca cacacacata tatatatgta    3960
tatgtatgta tgtatgtata tatatatact tttaatgcta aatagcctgg gttggctaag    4020
actacttcaa tcctgccaga attc                                           4044
```

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 3

```
tacgcccttc tcagttaggg ttag                                             24
```

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 4

```
ggatcctacg cccttctcag ttagggttag                                       30
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5

```
actgagccga gacaagattc                                                  20
```

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 6

```
ggatccactg agccgagaca agattc                                           26
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7

```
agctactcag gaggctgaga                                                  20
```

-continued

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 8
gcgctcgaga gctactcagg aggctgaga                              29

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
catcaagaca cagcactact                                        20

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 10
gcgctcgagc atcaagacac agcactact                              29

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
gtctggtctg cagaggatag                                        20

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 12
gcgctcgagg tctggtctgc agaggatag                              29

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 13
tacgcccttc tcagttaggg ttag                                   24

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Primer

```
<400> SEQUENCE: 14
cgcaagcttt acgcccttct cagttagggt tag                              33

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15
ctgagctgtg ggacgtgcac                                             20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
agacgggaga acccacgcag                                             20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 17
ctcggctcac acatgcagtt                                             20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 18
tctgcagagc aggaactaag t                                           21

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 19
ctaaccctaa ctgagaaggg cgta                                        24

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 20
ggcgaacggg ccagcagctg acatt                                       25

<210> SEQ ID NO 21
```

```
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 21
gtgtctcaca gcaagaaaca                                            20

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 22
gcgctcgagg tgtctcacag caagaaaca                                  29

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 23
gtgactggct aggaagagtg                                            20

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 24
gcgctcgagg tgactggcta ggaagagtg                                  29

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 25
tgtgaccttg aactacagac                                            20

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 26
gcgctcgagt gtgaccttga actacagac                                  29

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 27
```

```
ggactgggtt gaaggtggaa                                              20

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 28
gcgctcgagg gactgggttg aaggtggaa                                    29

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 29
tgcgccactt ttccccactt                                              20

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 30
gcgctcgagt gcgccacttt tccccactt                                    29

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 31
ccgctggaag tcagcgagaa                                              20

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 32
cgcaagcttc cgctggaagt cagcgagaa                                    29

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 33
gcgctcgagt cgaccaatca gcgcgcgcca t                                 31

<210> SEQ ID NO 34
<211> LENGTH: 20
<212> TYPE: DNA
```

<213> ORGANISM: Artificial Sequence
<220> FEATURE:
<223> OTHER INFORMATION: Description of Artificial Sequence: Primer

<400> SEQUENCE: 34
ccgctggaag tcagcgagaa                                             20

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 35
tcgaccaatc agcgcgcgcc at                                          22

<210> SEQ ID NO 36
<211> LENGTH: 867
<212> TYPE: DNA
<213> ORGANISM: Homo sapiens

<400> SEQUENCE: 36
agctactcag gaggctgaga cacgagaatc gcttgaaccc gggaggcaga ggttgcagtg    60
agccgagatc acgccactag actccatcca gcctgggcga agagcaaga ctccgtctca   120 aaaaaaaaaa tcgttacaat ttatggtgga ttactcccct cttttacct catcaagaca   180 cagcactact ttaaagcaaa gtcaatgatt gaaacgcctt tctttcctaa taaaagggag   240
attcagtcct taagattaat aatgtagtag ttacacttga ttaaagccat cctctgctca   300
aggagaagct ggagaaggca ttctaaggaa aaaggggcag ggttggaact cggacgcatc   360
ccactgagcc gagacaagat tctgctgtag tcagtgctgc ctgggaatct attttcacaa   420
agttctccaa aaaatgtgat gatcaaaact aggaattagt gttctgtgtc ttaggcccta   480
aaatcttcct gtgaattcca tttttaaggt agtcgaggtg aaccgcgtct ggtctgcaga   540
ggatagaaaa aaggccctct gatacctcaa gttagtttca cctttaaaga aggtcggaag   600
taaagacgca aagcctttcc cggacgtgcg gaagggcaac gtccttcctc atggccggaa   660
atggaacttt aatttcccgt tccccccaac cagcccgccc gagagagtga ctctcacgag   720
agccgcgaga gtcagcttgg ccaatccgtg cggtcggcgg ccgctccctt tataagccga   780
ctcgcccggc agcgcaccgg gttgcggagg gtgggcctgg gagggtggt ggccattttt   840 tgtctaaccc taactgagaa gggcgta                                      867

<210> SEQ ID NO 37
<211> LENGTH: 628
<212> TYPE: DNA
<213> ORGANISM: Mus sp.

<400> SEQUENCE: 37
tgtgaccttg aactacagac ctcctgcctc agcctcctac aagctgggat tataggctcg    60
ggtcagctac ccttgaaatc ttttttctttc tggaactcag tacctggttg gccatgcact   120
cacaagagat ccgcctgcct tctgtctctc aaattctgga attaaagatt gcgccacttt   180
ttccccactt ccaccccggc tgtgggagt ggactgggtt gaaggtggaa tttttttttt   240
tttttttttt ttttagtgaa aaagggggg attggaaata tccctacttt caactctagt   300
atatttcaga aaccaagcct cagagatgtg cgtgcgtgcg tgtgtgtgtg tgtatgtgtg   360
tgtgtctcac agcaagaaac agattttatt atttattttt tatttatta ttttttgcaa   420

```
gtgactggct aggaagagtg gggaagcggg aggacaaatg gggaagaggg agcatttccg      480
caagtgctgg gctcgaccaa tcagcgcgcg ccatgggta  tttaaggtcg agggcggcta      540
ggcctcggca cctaaccctg attttcatta gctgtgggtt ctggtctttt gttctccgcc      600
cgctgttttt ctcgctgact ccagcgg                                         628
```

```
<210> SEQ ID NO 38
<211> LENGTH: 622
<212> TYPE: DNA
<213> ORGANISM: Mus sp.

<400> SEQUENCE: 38
ttgtgacctt gaactacaga cctcctgcct cagcctccta caagctggga ttataggctc      60
gggtcagcta cccttgaaat tctttttctt tctggaactc agtacctggt tggccatgca     120
ctcacaagag atccgcctgc cttctgtcaa attctggaat taaagatttg cgccactttt     180
ccccacttcc accccggct  gtgggagtgg actgggttga agtggaatt  ttttttttt      240 tttttttagt gaaaaaaggg gggattgaa  atatccctac tttcaactct agtatatttc     300
agaaaccaag cctcagaaat gtgcgtgcgt gcgtgtgtgt gtgtgtatgt gtgtgtgtct     360
cacagcaaga aacagatttt attatttatt ttttatttat ttatttttg  caagtgactg     420 gctaggaaga gtggggaagc gggaggacaa atggggaaga gggagcattt ccgcaagtgc     480
tgggctcgac caatcagcgc gcgccatggg gtatttaagg tcgagggcgg ctaggcctcg     540
gcacctaacc ctgattttca ttagctgtgg gttctggtct ttcgttctcc gcccgctgtt     600
tttctcgctg acttccagcg ga                                              622
```

```
<210> SEQ ID NO 39
<211> LENGTH: 176
<212> TYPE: DNA
<213> ORGANISM: Homo sapiens

<400> SEQUENCE: 39
agcccgcccg agagagtgac tctcacgaga gccgcgagag tcagcttggc caatccgtgc      60
ggtcggcggc cgctcccttt ataagccgac tcgcccggca gcgcaccggg ttgcggaggg     120
tgggcctggg aggggtggtg gccatttttt gtctaaccct aactgagaag ggcgta         176
```

```
<210> SEQ ID NO 40
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 40
ccgggttgcg gagggtgggc ctgggagggg tggtggcc                              38
```

```
<210> SEQ ID NO 41
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 41
ccgggttgcg gaaatgggc  ctgggagggg tggtggcc                              38
```

```
<210> SEQ ID NO 42
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 42 ccggggttgcg gagggtgggc ctgggtaagg tggtggcc                    38

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 43 ccggggttgcg gaaaatgggc ctgggtaagg tggtggcc                    38

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 44 ccggggttgcg gagggtgggc ctggg                                   25

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 45
gcctgggagg ggtggtggcc                                          20

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 46 ccggggttgcg gaaaatgggc ctggg                                   25

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 47
gggcctgggt aaggtggtgg cc                                       22
```

```
<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 48
gggcctgggt aagtaatgg cc                                           22

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 49
gggcctggga ggggtaatgg cc                                          22

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 50
cttggccaat ccgtgcggtc gg                                          22

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 51
cttggagtct ccgtgcggtc gg                                          22

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 52
gcgagagtca gcttggagtc tccgtgcgg                                   29

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 53
cttggccaat cctgatggtc gg                                          22

<210> SEQ ID NO 54
```

```
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 54
cggcggccgc tccctttata agccgact                                28

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 55
cttacgccgc tccctttata agcc                                    24

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 56
ccgtgcggtc ttacgccgct ccc                                     23

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 57
cggcgtaaac tccctttata agcc                                    24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 58
cggcggccat agcctttata agcc                                    24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 59
cggcggccgc tcatgctata agcc                                    24

<210> SEQ ID NO 60
<211> LENGTH: 24
```

```
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 60
cggcggccgc tcccttcgac agcc                                           24

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 61
ccgctccctt cgacagccga ctcgc                                          25

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 62
accagcccgc ccgagagagt                                                20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 63
accagcccga acgagagagt                                                20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 64
gaaaaagggg cagggttgga                                                20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 65
gaaaaaggtt cagggttgga                                                20

<210> SEQ ID NO 66
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      sequence

<400> SEQUENCE: 66
cttacgccgc tcccttata agccgact                                           28

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic
      sequence

<400> SEQUENCE: 67
cggcgtaaac tcccttata agccgact                                           28

<210> SEQ ID NO 68
<211> LENGTH: 28
<212> TYPE: DNA
<213> ORGANISM: Artificial Sequence
<220> FEATURE:
<223> OTHER INFORMATION: Description of Artificial Sequence: Synthetic
      sequence

<400> SEQUENCE: 68
cggcggccat agcctttata agccgact                                          28

<210> SEQ ID NO 69
<211> LENGTH: 28
<212> TYPE: DNA
<213> ORGANISM: Artificial Sequence
<220> FEATURE:
<223> OTHER INFORMATION: Description of Artificial Sequence: Synthetic
      sequence

<400> SEQUENCE: 69
cggcggccgc tcatgctata agccgact                                          28

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Synthetic
      sequence

<400> SEQUENCE: 70
cggcggccgc tcccttcgac agccgact                                          28

<210> SEQ ID NO 71
<211> LENGTH: 53
<212> TYPE: DNA
<213> ORGANISM: Artificial Sequence
<220> FEATURE:
<223> OTHER INFORMATION: Description of Artificial Sequence: Mutant
      construct

<400> SEQUENCE: 71
agcccgaacg agagagtgac tctcacgaga gccgcgagag tcagcttggc caa              53

<210> SEQ ID NO 72
<211> LENGTH: 53
<212> TYPE: DNA
<213> ORGANISM: Artificial Sequence
```

```
<220> FEATURE:
<223> OTHER INFORMATION: Description of Artificial Sequence: Mutant
      construct

<400> SEQUENCE: 72
agcccgcccg agagagtgac tctcacgaga gccgcgagag tcagcttgga gtc          53

<210> SEQ ID NO 73
<211> LENGTH: 107
<212> TYPE: DNA
<213> ORGANISM: Artificial Sequence
<220> FEATURE:
<223> OTHER INFORMATION: Description of Artificial Sequence: Mutant
      construct

<400> SEQUENCE: 73
agcccgaacg agagagtgac tctcacgaga gccgcgagag tcagcttggc caatccgtgc     60
ggtcggcggc catagccttt ataagccgac tcgcccggca gcgcacc                  107

<210> SEQ ID NO 74
<211> LENGTH: 107
<212> TYPE: DNA
<213> ORGANISM: Artificial Sequence
<220> FEATURE:
<223> OTHER INFORMATION: Description of Artificial Sequence: Mutant
      construct

<400> SEQUENCE: 74
agcccgaacg agagagtgac tctcacgaga gccgcgagag tcagcttggc caatccgtgc     60
ggtcggcggc cgctcatgct ataagccgac tcgcccggca gcgcacc                  107

<210> SEQ ID NO 75
<211> LENGTH: 54
<212> TYPE: DNA
<213> ORGANISM: Artificial Sequence
<220> FEATURE:
<223> OTHER INFORMATION: Description of Artificial Sequence: Mutant
      construct

<400> SEQUENCE: 75
tcctgatggt cggcggccgc tccctttata agccgactcg cccggcagcg cacc           54

<210> SEQ ID NO 76
<211> LENGTH: 54
<212> TYPE: DNA
<213> ORGANISM: Artificial Sequence
<220> FEATURE:
<223> OTHER INFORMATION: Description of Artificial Sequence: Mutant
      construct

<400> SEQUENCE: 76
tccgtgcggt cttacgccgc tccctttata agccgactcg cccggcagcg cacc           54

<210> SEQ ID NO 77
<211> LENGTH: 54
<212> TYPE: DNA
<213> ORGANISM: Artificial Sequence
<220> FEATURE:
<223> OTHER INFORMATION: Description of Artificial Sequence: Mutant
      construct

<400> SEQUENCE: 77
tccgtgcggt cggcgtaaac tccctttata agccgactcg cccggcagcg cacc           54

<210> SEQ ID NO 78
```

<211> LENGTH: 54
<212> TYPE: DNA
<213> ORGANISM: Artificial Sequence
<220> FEATURE:
<223> OTHER INFORMATION: Description of Artificial Sequence: Mutant
      construct

<400> SEQUENCE: 78
tccgtgcggt cggcggccat agcctttata agccgactcg cccggcagcg cacc        54

<210> SEQ ID NO 79
<211> LENGTH: 54
<212> TYPE: DNA
<213> ORGANISM: Artificial Sequence
<220> FEATURE:
<223> OTHER INFORMATION: Description of Artificial Sequence: Mutant
      construct

<400> SEQUENCE: 79
tccgtgcggt cggcggccgc tcatgctata agccgactcg cccggcagcg cacc        54

<210> SEQ ID NO 80
<211> LENGTH: 54
<212> TYPE: DNA
<213> ORGANISM: Artificial Sequence
<220> FEATURE:
<223> OTHER INFORMATION: Description of Artificial Sequence: Mutant
      construct

<400> SEQUENCE: 80
tccgtgcggt cggcggccgc tcccttcgac agccgactcg cccggcagcg cacc        54

<210> SEQ ID NO 81
<211> LENGTH: 120
<212> TYPE: DNA
<213> ORGANISM: Artificial Sequence
<220> FEATURE:
<223> OTHER INFORMATION: Description of Artificial Sequence: Mutant
      construct

<400> SEQUENCE: 81
gtgcggtcgg cggccgctcc ctttataagc cgactcgccc ggcagcgcac cgggttgcgg    60
agggtgggcc tgggaggggt ggtggccatt ttttgtctaa ccctaactga aagggcgta   120

<210> SEQ ID NO 82
<211> LENGTH: 51
<212> TYPE: DNA
<213> ORGANISM: Artificial Sequence
<220> FEATURE:
<223> OTHER INFORMATION: Description of Artificial Sequence: Mutant
      construct

<400> SEQUENCE: 82
gggttgcgga aaatgggcct gggaggggtg gtggccattt tttgtctaac c           51

<210> SEQ ID NO 83
<211> LENGTH: 51
<212> TYPE: DNA
<213> ORGANISM: Artificial Sequence
<220> FEATURE:
<223> OTHER INFORMATION: Description of Artificial Sequence: Mutant
      construct

<400> SEQUENCE: 83
gggttgcgga gggtgggcct gggtaaggtg gtggccattt tttgtctaac c           51

```
-continued

<210> SEQ ID NO 84
<211> LENGTH: 51
<212> TYPE: DNA
<213> ORGANISM: Artificial Sequence
<220> FEATURE:
<223> OTHER INFORMATION: Description of Artificial Sequence: Mutant
      construct

<400> SEQUENCE: 84
gggttgcgga aaatgggcct gggtaaggtg gtggccattt tttgtctaac c          51

<210> SEQ ID NO 85
<211> LENGTH: 51
<212> TYPE: DNA
<213> ORGANISM: Artificial Sequence
<220> FEATURE:
<223> OTHER INFORMATION: Description of Artificial Sequence: Mutant
      construct

<400> SEQUENCE: 85
gggttgcgga gggtgggcct gggtaaggta atggccattt tttgtctaac c          51

<210> SEQ ID NO 86
<211> LENGTH: 51
<212> TYPE: DNA
<213> ORGANISM: Artificial Sequence
<220> FEATURE:
<223> OTHER INFORMATION: Description of Artificial Sequence: Mutant
      construct

<400> SEQUENCE: 86
gggttgcgga aaatgggcct gggtaaggta atggccattt tttgtctaac c          51
```

PROMOTER REGIONS OF THE MOUSE AND HUMAN TELOMERASE RNA COMPONENT GENES

FIELD OF THE INVENTION

The present invention relates to the cloning of a genomic promoter region of the human and mouse telomerase RNA gene. Particularly, but not exclusively, it relates to the identity of elements important for the regulation of telomerase RNA genes.

BACKGROUND OF THE INVENTION

Telomeres are found at the end of linear chromosomes and consist of short repetitive sequences essential for the maintenance of normal chromosome structure and function (Wellinger & Sen, 1997). With each cell division, telomeres shorten due to the inability of DNA polymerases to replicate the ends of linear DNA molecules. However, telomere erosion is counteracted by the activity of the enzyme telomerase, a ribonuclear protein with reverse transcriptase activity, which adds telomeric repeats to the chromosomal termini (Morin, 1997; Nakamura et al., 1997). The genes for the human, (hTR), and mouse, (terc), RNA components have recently been cloned, as has the human protein component, (hTRT) (Blasco et al., 1995; Feng et al., 1995; Nakamura et al., 1997; Soder et al., 1997b; Soder et al., 1997c). Whilst telomerase expression is detectable in normal embryonic tissues and germline stem cells, telomerase expression is repressed in most normal postnatal somatic cells (Blasco et al., 1995; Feng et al., 1995; Prowse & Greider, 1995; Soder et al., 1997a; Wright et al., 1996). The lack of telomerase expression may be the major reason for the progressive loss of telomeric sequences in somatic cells, which is considered to be one regulatory mechanism which monitors the number of times a cell divides before entering replicative senescence (Campisi, 1997). However, although telomerase appears to be stringently repressed in normal somatic tissues, there is substantial evidence to suggest that telomerase is expressed in the majority of human cancers and contributing to the immortal phenotype through the maintenance of telomere integrity (Holt et al., 1997; Kim, 1997; Shay & Bacchetti, 1997).

The regulation of telomerase expression is a complex issue including transcriptional activity of the telomerase RNA and protein component genes, interaction of telomerase with other telomere associated proteins and post-translational modification of the enzyme complex. However, at present there are few studies which directly address the mechanisms regulating telomerase expression in normal and cancer cells (Bodnar et al., 1996; Broccoli et al., 1997; Li et al., 1997; Mandal & Kumar, 1997; Morin, 1997; Nakamura et al., 1997; Soder et al., 1997a).

Studies aimed at relating genome stability to human cellular senescence have recently placed considerable emphasis on telomerase expression as a central unifying mechanism underlying the immortal phenotype of many cancers (Breslow et al., 1997). The absence of telomerase activity from normal somatic cells has led to the proposal that telomere shortening may be a molecular clock which contributes to the onset of cellular senescence in normal cells (Harley & Villeponteau, 1995; Holt et al., 1996). Conversely, the reactivation or expression of telomerase may be a major mechanism by which cancer overcome normal cellular senescence (Kim et al., 1994; Parkinson et al., 1997). Information on telomerase activity in tumours almost exclusively derives from the in vitro telomere repeat amplification protocol, (TRAP), and these have shown that telomerase activity may be present in greater than 80% of tumour biopsies yet absent or reduced in normal somatic tissue (Breslow et al., 1997; Kim et al., 1994; Raymond et al., 1996; Shay & Wright, 1996). However, TRAP assay alone will not reveal the true complexities of telomerase regulation, and it is generally recognised that a number of molecular approaches will be required to understand telomere length regulation and telomerase activity (Breslow et al., 1997; Holt et al., 1996; Lundblad & Wright, 1996; Parkinson et al., 1997; Raymond et al., 1996; Soder et al., 1997b). Recently, the present inventors and others have introduced a number of more direct in situ approaches to study the telomerase RNA gene, (hTR) and its expression in tumours (Soder et al., 1997; Yashima et al., 1997b).

U.S. Pat. No. 5,583,016 (Geron Corp.) Discloses a 2.4 kb sequence of the Telomerase RNA gene. However, there is no disclosure of the promoter elements or provision of functional evidence to show the promoter is active.

SUMMARY OF THE INVENTION

The levels of telomerase RNA gene expression vary during normal development and between normal and cancerous cells and tissues (Avilion et al., 1996; Bestilny et al., 1996; Blasco et al., 1995; Blasco et al., 1996; Bodnar et al., 1996; Broccoli et al., 1996; Feng et al., 1995; Kuniyasu et al., 1997; Soder et al., 1997a). The present inventors have appreciated that knowledge of telomerase RNA gene expression should aid understanding of the signal transduction pathways linking telomere attrition to proliferation, cellular senescence, differentiation and oncogenesis. As a first step towards this goal, they have cloned the promoter regions of the human, (hTR), and mouse, (terc), telomerase RNA genes in order to identify the regulatory elements controlling telomerase RNA gene transcription. Further, the present inventors have investigated the possible levels of telomerase regulation in vivo.

These studies have a number of implications for the development of new transcription based therapies for cancer (Cai et al., 1996; Connors, 1995; Miller & Whelan, 1997; Peterson & Baichwal, 1993). Directly down-regulating expression of the telomerase RNA gene through manipulation of transcription factors should be an effective anticancer therapy and the cloning of the hTR gene promoter will allow the analysis of therapeutic molecules which modulate hTR promoter activity (Cai et al., 1996; Peterson & Baichwal, 1993; Sharma et al., 1997). Indeed, by using a human cell line which has telomerase activity, (HeLa) and one which expresses the hTR gene but is telomerase negative, (GM847), (Bryan et al., 1997), the present inventors provide a system in which the specificity of transcriptional manipulation of hTR may be examined. In comparison to HeLa, the growth of GM847 does not appear to be dependant on telomerase expression, thus transcriptional targeting of hTR in GM847 should have no cellular effects, whereas HeLa should be sensitive to the predicted anti-proliferative effects of the transcriptional targeting. In addition, the present inventors show tumour-specific patterns of hTR gene expression with clear differentials in expression between cancerous and adjacent normal tissue, (Soder et al., 1997a (not yet published); Soder et al., 1997b).

Broadly, the present invention provides materials and methods relating to the telomerase RNA (TR) gene promoter and its effects in tumour development.

According to a first aspect there is provided a nucleic acid molecule comprising the TR gene promoter.

In a second aspect there is provided a nucleic acid molecule comprising a human TR gene promoter, preferably the promoter comprising a sequence of nucleotides shown in FIG. 4a. The promoter may comprise one or more fragments of the sequence shown in FIG. 4a, sufficient to promote gene expression. In particular, it may comprise or consist essentially of a sequence of nucleotides extending at least 200 base pairs (bp), or 250 bp, 272 bp, or 300 bp, preferably at least 320 bp, more preferably at least 340 bp, even more preferably at least 400 bp upstream of the transcription start site. More preferably, the promoter may comprise a sequence of nucleotides of at least 230 bp in length starting at position −42 bp upstream of the transcription start site (FIG. 4a and FIG. 5a). Even more preferably the promoter may comprise a sequence of nucleotides of at least 230 bp in length between positions −272 bp and −42 bp (FIG. 4a and FIG. 5a).

In a further preferred form the promoter comprises or consists essentially of the construct designated hProm505 being a sequence of nucleotides of 505 bp in length from position −436 as shown in FIG. 4 or the construct designated hProm867 being 867 bp in length from position −798 bp (FIG. 4a and FIG. 5a).

In a third aspect of the present invention there is provided a nucleic acid molecule comprising mouse Telomerase RNA (terc) gene promoter, preferably comprising or consisting essentially of the sequence as shown in FIG. 4b. In a preferred form, the present invention provides a nucleic acid molecule comprising a terc promoter, said promoter comprising or consisting essentially of a nucleotide sequence extending at least 94 bp, preferably at least 100 bp, more preferably at least 120 bp, even more preferably at least 150 bp upstream of the transcription start site. Preferably the promoter comprises or consists essentially of a nucleotide sequence of approximately 73 bp in length between −94 bp and −22 bp as shown in FIG. 4b and FIG. 5b.

In further preferred form, the present invention provides a nucleic acid molecule comprising or consisting essentially of the construct designated mProm208 or the construct designated mProm628 as shown in FIG. 4 or FIG. 5b.

An even smaller portion of the nucleotide sequences mentioned above may be used as long as the promoter activity is retained. Such nucleotide sequences may be fragments being 200 nucleotides or fewer in length (e.g. 150, 100, 50, 40, 35, 30, 25, or 20). Restriction enzymes or nucleases may be used to digest the nucleic acid, followed by the appropriate assay (for example as illustrated herein using luciferase constructs) to determine the minimal sequence required. A preferred embodiment of the present invention provides a nucleic acid molecule with the minimal nucleotide sequence shown in FIG. 4a or FIG. 4b required for promoter activity. The minimal promoter is situated between −272 bp and −42 bp as shown in FIG. 4a and between −94 bp and −22 bp as shown in FIG. 4b.

The promoter may comprise one or more sequence motifs or elements conferring developmental and/or tissue-specific regulatory control or expression. Other regulatory sequences may be included, for instance as identified by mutation or digest assay in an appropriate expression system or by sequence comparison with available information, e.g. using a computer to search on-line databases.

By "promoter" is meant a sequence of nucleotides from which transcription may be initiated of DNA operably linked downstream (i.e. in the 3' direction on the sense strand of double-stranded DNA). In the present case, the sequence of nucleotides is derived from either hTR promoter region or the mouse terc promoter. In other words, the nucleotide sequence may be identical to that of the hTR or the terc promoter in both size and sequence, or it may have been modified by insertion, addition, deletion or substitution of one or more nucleotides without fundamentally altering the essential activity of the promoter as compared to the hTR or terc promoter activity respectively. The essential activity can be determined by analysis of individual promoter elements as to their size, sequence and susceptibility to transcriptional control elements as described herein. Further, within the meaning of the term "promoter" is a sequence of nucleotides derived from either hTR promoter region or the mouse terc promoter which on its own lacks the essential activity but which can regain activity on addition of further nucleotide sequence, particularly nucleotide sequence comprising further promoter elements known to those skilled in the art.

"Operably linked" means joined as part of the same nucleic acid molecule, suitably positioned and orientated for transcription to be initiated from the promoter. DNA operably linked to a promoter is "under transcriptional initiation regulation" of the promoter.

The present invention extends to a promoter which is an allele, mutant, variant or derivative, by way of nucleotide addition, substitution or deletion of a promoter sequence as provided herein. Systematic or random mutagenesis of nucleic acid to make an alteration to the nucleotide sequence may be performed using any technique known to those skilled in the art. One or more alterations to a promoter sequence according to the present invention may increase or decrease promoter activity, or increase or decrease the magnitude of the effect of a substance able to modulate the promoter activity.

"Promoter activity" is used to refer to ability to initiate transcription. The level of promoter activity is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridise with the mRNA and which are labelled or may be used in a specific amplification reaction such as the polymerase chain reaction. Use of a reporter gene as discussed further below facilitates determination of promoter activity by reference to protein production.

In various embodiments of the present invention a promoter which has a sequence that is a fragment, mutant, allele, derivative or variant, by way of addition, insertion, deletion or substitution of one or more nucleotides, of the sequence of the hTR promoter shown in FIG. 4a or the terc promoter shown in FIG. 4b, has at least about 60% homology with one or both of the shown sequences, preferably at least about 70% homology, more preferably at least about 80% homology, more preferably at least about 90% homology, more preferably at least about 95% homology. Such homology may be found over a sequence of at least 10 nucleotides, preferably of at least 20 nucleotides, more preferably of at least 30 nucleotides and even more preferably of at least 40 nucleotides. Such fragments themselves individually represent aspects of the present invention.

The sequence in accordance with an embodiment of the invention may hybridise with one or both of the shown sequences, or the complementary sequences (since DNA is generally double-stranded). The sequence may have the ability to promote transcription (i.e. have "promoter activity") in normal embryonic tissues and germline stem cells.

In accordance with the present invention, nucleic acids having the appropriate level of sequence homology with the respective promoter regions may be identified by using hybridization and washing conditions of appropriate stringency. For example, hybridizations may be performed, according to the method of Sambrook et al., (22) using a hybridization solution comprising: 5×SSC, 5× Denhardt's reagent, 0.5–1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_m = 81.5° C. + 16.6 \log[Na+] + 0.41(\% G+C) - 0.63(\% \text{formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the respective promoter sequences of the present invention.

On the basis of the nucleotide sequences given herein (FIG. 4a and FIG. 4b), oligonucleotide probes or primers may be designed. Generally specific primers are upwards of 14 nucleotides in length but not more than 18 to 20. Those skilled in the art are well versed in the design of primers for use processes such as PCR. Primer sequences which themselves individually form part of the present invention are given in FIG. 6.

Further provided by the present invention is a nucleic acid construct comprising a TR promoter region or a fragment, mutant, allele, derivative or variant thereof able to promote transcription, operably linked to a heterologous gene, e.g. a coding sequence. By "heterologous" is meant a gene other than TR gene. Modified forms of TR are generally excluded. Generally, the gene may be transcribed into mRNA which may be translated into a peptide or polypeptide product which may be detected and preferably quantitated following expression. A gene whose encoded product may be assayed following expression is termed a "reporter gene", i.e. a gene which "reports" on promoter activity.

The reporter gene preferably encodes an enzyme which catalyses a reaction which produces a detectable signal, preferably a visually detectable signal, such as a coloured product. Many examples are known, including β-galactosidase and luciferase. β-galactosidase activity may be assayed by production of blue colour on substrate, the assay being by eye or by use of a spectrophotometer to measure absorbance. Luminescence, for example that produced as a result of luciferase activity, may be quantitated using a spectrophotometer. Radioactive assays may be used, for instance using chloramphenicol acetyltransferase, which may also be used in non-radioactive assays. The presence and/or amount of gene product resulting from expression from the reporter gene may be determined using a molecule able to bind the product, such as an antibody or fragment thereof. The binding molecule may be labelled directly or indirectly using any standard technique.

Those skilled in the art are well aware of a multitude of possible reporter genes and assay techniques which may be used to determine gene activity. Any suitable reporter/assay may be used and it should be appreciated that no particular choice is essential to or a limitation of the present invention.

Expression of a reporter gene from the promoter may be in an in vitro expression system or may be intracellular (in vivo). Expression generally requires the presence, in addition to the promoter which initiates transcription, a translational initiation region and transcriptional and translational termination regions. One or more introns may be present in the gene, along with mRNA processing signals (e.g. splice sites).

The present invention also provides a nucleic acid vector comprising a promoter as disclosed herein. Such a vector may comprise a suitably positioned restriction site or other means for insertion into the vector of a sequence heterologous to the promoter to be operably linked thereto.

Suitable vectors can be chosen or constructed containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Procedures for introducing DNA into cells depend on the host used, but are well known.

Thus, a further aspect of the present invention provides a host cell containing a nucleic acid construct comprising a promoter element, as disclosed herein, operably linked to a heterologous nucleic acid coding sequence or a gene. In particular, the promotor of the present invention may be used to drive expression of an exogenous protein in selected cells. For example, the coding sequence or gene may encode a cytotoxin which can then be selectively expressed in target cells e.g. tumour cells. Many such cytotoxins are known to the skilled person. They may include cytotoxins derived from viruses, bacteria or bacteriophages. Alternatively, the heterologous gene may encode a endogenous protein and the promoter may be used to increase the expression of said endogenous protein in selective cells.

A still further aspect provides a method comprising introducing such a construct into a host cell. The introduction may employ any available technique, including, for eukaryotic cells, calcium phosphate transfection, DEAE-Dextran transfection, electroporation, liposome-mediated transfection and transduction using retrovirus.

The introduction may be followed by causing or allowing expression of the heterologous gene under the control of the promoter, e.g. by culturing host cells under conditions for expression of the gene.

In one embodiment, the construct comprising promoter and gene is integrated into the genome (e.g. chromosome) of the host cell. Integration may be promoted by inclusion in the construct of sequences which promote recombination with the genome, in accordance with standard techniques.

Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology*, Second Edition, Ausubel et al. eds., John Wiley & Sons, 1992, the disclosure of which is incorporated herein by reference.

Nucleic acid molecules, constructs and vectors according to the present invention may be provided isolated and/or purified (i.e. from their natural environment), in substantially pure or homogeneous form, free or substantially free of a TR coding sequence, or free or substantially free of nucleic acid or genes of the species of interest or origin other than the promoter sequence. Nucleic acid according to the present invention may be wholly or partially synthetic. The term "isolate" encompasses all these possibilities.

Nucleic acid constructs comprising a promoter (as disclosed herein) and a heterologous gene (reporter) may be employed in screening for a substance able to modulate activity of the promoter. For therapeutic purposes, e.g. for treatment of cancers, a substance able to regulate the promoter may be sought. A method of screening for ability of a substance to modulate activity of a TR promoter may comprise contacting an expression system, such as a host cell, containing a nucleic acid construct as herein disclosed with a test or candidate substance and determining expression of the heterologous gene.

The level of expression in the presence of the test substance may be compared with the level of expression in the absence of the test substance. A difference in expression in the presence of the test substance indicates ability of the substance to modulate gene expression. A decrease in expression of the heterologous gene compared with expression of another gene not linked to a promoter as disclosed herein indicates specificity of the substance for disrupting the TR promoter.

A promoter construct may be transfected into a cell line using any technique previously described to produce a stable cell line containing the reporter construct integrated into the genome. The cells may be grown and incubated with test compounds for varying times. The cells may be grown in 96 well plates to facilitate the analysis of large numbers of compounds. The cells may then be washed and the reporter gene expression analysed. For some reporters, such as luciferase the cells will be lysed then analysed.

Constructs comprising one or more developmental and/or time-specific regulatory motifs (as discussed) may be used to screen for a substance able to modulate the corresponding aspect of the promoter activity, e.g. cancer related expression.

There is interest in prolonging the cellular lifespan of normal cells and keeping them normal rather than them aging or senescing. In this regard, the present invention provides the ability to upregulate or switch on at least TR and the protein component gene hTERT. This application may provide immortal normal cells for treating age related diseases or to get unlimited amounts of commercially important normal cells. Alternatively, applications for substances able to suppress promoter activity are also provided, for example, for use in cancer therapy. Following identification of a substance which modulates or affects TR gene promoter activity, the substance may be investigated further. Furthermore, it may be manufactured and/or used in preparation, i.e. manufacture or formulation, of a composition such as a medicament, pharmaceutical composition or drug. These may be administered to individuals.

Thus, the present invention extends in various aspects not only to a substance identified using a nucleic acid molecule as a modulator of TR gene promoter activity, in accordance with what is disclosed herein, but also a pharmaceutical composition, medicament, drug or other composition comprising such a substance, a method comprising administration of such a composition to a patient, e.g. for decreasing TR gene expression for instance in treatment of cancers, use of such a substance in manufacture of a composition for administration, e.g. for decreasing TR gene expression for instance in treatment of cancers, and a method of making a pharmaceutical composition comprising admixing such a substance with a pharmaceutically acceptable excipient, vehicle or carrier, and optionally other ingredients.

Administration will preferably be in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, eg decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Also included within the scope of the present invention are substances that disrupt the ability of the TR gene promoter as herein described to regulate expression of the TR gene. These substances include any member that is capable of directly down-regulating telomerase RNA gene expression or which specifically blocks transcriptional activation of the TR gene promoters through interaction of the 5' regulatory sequences, for example, antisense oligonucleotides, transcription factors, synthetic oligonucleotides and peptide nucleic acids (hybrid molecules between peptides and nucleic acids) or factors that disrupt signal transduction pathways. Having identified the proximal region of the hTR promoter necessary to direct hTR transcription, a number of potential recognition sites for transcription factors have been identified by the present inventor (see FIG. 10). The present invention provides such transcription factors or functional fragments thereof for use in the modifying hTR transcription.

The present inventors have further devised reporter constructs, which form part of the invention, which can be introduced into cells or cell free systems to monitor promoter activity. This allows regulation of transcription and the development of small molecules specifically designed to disrupt the hTR transcriptional machinery. The reporter cell lines so produced also form part of the invention and are ideally suited to test any commercial telomerase inhibitors which may be evaluated, in combination with standard telomerase assays for specificity and mode of action. Therefore, the present invention provides methods and kits for testing telomerase inhibitors and molecules specifically designed to disrupt hTR transcriptional machinery. Further, the present invention extends to the use of these reporter constructs to monitor promoter activity and regulate transcription.

The identification of the transcription factors regulating telomerase RNA gene expression and the elucidation of the specific molecules of the signal transduction pathways regulating expression will provide a wealth of targets for anticancer agents. Inhibitors may be developed by rational design based on the molecular understanding of telomerase RNA gene expression or the screening of pharmaceutical compounds in screens based on promoter/reporter activity.

Therefore, the present invention provides a method of identifying transcription factors capable of regulating TR gene expression comprising the steps of screening for compounds which disrupt TR gene promoter activity as determined by reporter activity. Telomerase inhibitors identified by such methods as described above are also within the scope of the present invention.

The work performed by the present inventors shows examples of clear differentials in hTR expression between cancerous and adjacent normal tissue which support the possibility of effective telomerase-based therapy (Soder et al 1997b; and Table 1 below). Indeed, the presence of high levels of hTR expression in specific cancers shows that the hTR/terc promoter may be used for genetic therapies designed to target therapeutic genes to tumours, via tumour specific gene expression.

Therefore, the present invention provides the use of nucleic acid molecules comprising promoter, promoter constructs or fragments thereof as described above for gene therapy. This includes the preparation of a medicament for use in gene therapy.

Vectors such as viral vectors have been used in the prior art to introduce genes into a wide variety of different target cells. Typically the vectors are exposed to the target cells so that transfection can take place in a sufficient proportion of the cells to provide a useful therapeutic or prophylactic effect from the expression of the desired polypeptide. In the present case, transcription and therefore expression of the desired polypeptide will be under the control of the promoter according to the present invention. The transfected nucleic acid comprising the promoter sequence and the sequence encoding the desired polypeptide may be permanently incorporated into the genome of each of the targeted tumour cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer.

Genetically directed enzyme prodrug therapy, (GDEPT), comprises two parts: a tumour specific promoter and the enzyme prodrug system. The properties of an optimal tumour selective transcriptional activation system can be summarized as, ideally tumour specific, only expressed in nonessential tissues, no cross-specificity with unusual but essential cell types, regulatory elements from gene cloned and sequenced, specific transcription factor binding sites identified, enhancer and inhibitory factors understood. The telomerase RNA gene promoters according to the present invention have these characteristics.

The present invention therefore provides the use of nucleic acid molecules comprising promoters as described herein to drive expression of enzyme-prodrug activation systems such as viral thymidine kinase and Gancyclovir, although many other systems known to those skilled in the art may also used. Targeted gene expression via the telomerase RNA gene promoter may also be used in gene replacement strategies for cancer therapy. The present invention also provides a system for use in the control of neoplasia in a human or aminal subject comprising a vector or other delivery system capable of selectively infecting tumour cells in said subject, said vector carrying a DNA or RNA sequence encoding an enzyme operably linked to a promoter sequence of the present invention, in association with a prodrug capable of being converted into an active compound by the action of said enzyme. The present invention further extends to a method of treating neoplasia in a human or animal subject requiring such treatment which comprises administering to the host an effective amount of a prodrug and a modified virus, said modified virus capable of selectively infecting tumour cells in said subject, said virus carrying a DNA or RNA sequence encoding an enzyme capable of converting said prodrug to an active compound, said DNA or RNA sequence being operably linked to a promoter sequence in accordance with the present invention.

The present invention also expends to a method of treating neoplasia in a human or animal subject requiring such treatment which comprises administering to the host an effective amount of a prodrug and a non-viral vector system, said non-viral vector system capable of being selectively introduced into tumour cells in said subject, said vector system carrying a DNA or RNA sequence encoding an enzyme capable of coverting said prodrug to an active compound, said DNA or RNA sequence being operably linked to a promoter in accordance with the present invention effective in expressing said enzyme in said cells. This aspect of the present invention is described in more detail below.

Genomic sequences encompassing the promoter region of hTR and terc have been cloned into green fluorescent protein (GFP) vectors and luciferase gene reporter vectors to assay for promoter activity, and deletion and mutation constructs have been developed. By introducing these constructs into primary cultures of keratinocytes/fibroblasts and neoplastic cell lines, which have varying levels of telomerase activity and telomerase RNA gene expression, genomic regions controlling repression or activation of hTR/terc expression may be identified. Human embryonic cells and murine embryonic stem cells may be used to study the developmental regulation of the expression.

The present invention also provides DNA binding assays for identifying transcription factors in crude cell extracts. As specific promoter regions have been identified by the present inventors, specific DNA-protein interactions may be analysed by gel mobility shift assay and DNase I footprinting which are well known techniques to those skilled in the art (Gene Transcription, eds Hames, B. D. and Higgins, S. J., IRL press, Oxford University Press, Oxford 1993). In addition, in vitro transcription assays for the hTR/terc promoters may be developed to study transcription factor interactions. Protein extracts from a) cell lines with and without telomerase RNA gene expression; b) early and late passage primary keratinocytes and fibroblasts; and c) tumour biopsies from patients, may be assayed for the involvement of previously characterised transcription factors by the use of purified transcription factors, oligonucleotide competition studies and antibodies to previously characterised factors. Should it be required, appropriate methods for the identification of the proteins responsible for the DNA-binding activity, such as UV crosslinking and protein purification and gene cloning may be performed. Proteins identified in this way will be considered as targets for inhibition and also form part of the invention.

The invention further provides a method for transcriptional analysis using transgenic mice. Transgenic mice with the human and mouse promoter/reporter constructs may be generated. Such transgenic mammals form part of the present invention. Also, the invention provides a method of creating transgenic mammals comprising the steps of injecting constructs into eggs of the mammal and re-implanting the eggs into the female mammal. Ideally the mammal will be a mouse although those skilled in the art will readily contemplate the use of other mammals such as rats or rabbits. Mice carrying constructs in the germline may be used to establish transgenic lines. The invention also includes the use of human or mouse promoter/reporter constructs for the generation of transgenic mammals. The use of transgenic mice for the analysis of transcription factors has a number of advantages over tissue culture cell line models, for example, cell types not easily maintained in culture may be studied; gene expression during animal development may be studied; relevant mouse models of human disease may be developed; reporter mice may be crossed with mouse strains with other transgenes or mouse knockouts to evaluate the biological effects of these genes on telomerase RNA gene promoter activity; and compounds or molecules thought to modulate promoter activity can be tested in vivo, thus taking into account pharmacology of the test compounds. This may be important if modulators of promoter activity are to be used clinically.

In a further aspect, the present invention provides a method for identifying genes regulating telomerase RNA gene expression comprising the step of introducing reporter constructs stably into cell lines and single chromosomes into the cell lines via microcell-mediated chromosome transfer (England, N. L. et al Carcinogenesis Vol. 17(8) pp 1567–1575, 1996). This allows for fluctuations in reporter gene activity due to genes on the single chromosome to be monitored. This will identify genes carrying regulators of promoter expression and thus the signal transduction pathway controlling telomerase RNA gene transcription. Gene products identified in this way will be considered as targets for inhibition and form part of the present invention.

The present invention provides methods for identifying genes regulating telomerase RNA gene expression comprising the steps of introducing reporter constructs stably into cell lines and expression libraries transfected into the reporter lines. The expression libraries may be made from cells known to repress or activate telomerase activity and telomerase RNA expression. Fluctuations in reporter activity due to genes in the expression library may then be monitored, and the genes cloned. Gene products identified in this way will be considered as targets for inhibition and form part of the present invention.

In a further aspect, the present invention provides a method for testing candidate genes for promoter regulating activity, comprising the steps of transfecting candidate genes into cell lines containing the promoter/reporter constructs and monitoring fluctuations in reporter activity due to said candidate genes.

The present invention extends to the use of the TR gene promoter for any of the methods given above. This includes the use of any promoter/reporter constructs, preferably those identified in FIG. 4 and FIG. 5.

Aspects and embodiments of the present invention will now be further described by way of example only with reference to the accompanying drawings. Further aspects of the invention will be apparent to those or ordinary skilled in the art. All documents mentioned in this text are incorporated herein by reference.

BRIEF DESCRIPTION OF THE DRAWINGS

FIG. 1 shows the 1765 bp genomic nucleotide sequence (SEQ ID NO: 1) of human telomerase gene (hTR) encompassing the gene promoter region. Transient expression of hTR-reporter gene constructs in HeLa and GM847 cells identified indicate that the elements responsible for promoter activity are contained in a 231 bp region upstream of the transcriptional start site.

FIG. 2 shows the 4044 bp genomic nucleotide sequence (SEQ ID NO: 2) of mouse telomerase RNA gene (terc) encompassing the gene promoter region. Transient expression of terc-reporter gene constructs in SWISS3T3 and A9 cells identified the elements responsible for promoter activity are contained in a 73 bp region upstream of the transcriptional start site.

FIG. 4 shows the nucleotide sequence of the human (A, SEQ ID NO: 36) and mouse (B, SEQ ID NO: 37) telomerase RNA gene 5'-flanking regions. Putative regulatory motifs are underlined. Arrows indicate the transcriptional start sites, (Blasco et al., 1995; Fen et al., 1995) and numbers to the left of each Figure refer to the number of bases upstream of the transcriptional start site. The template regions are in bold and underlined. Sequences contained in promoter constructs are shown by vertical lines and labeled, hProm or mProm, (see FIGS. 1 and 3). The regions containing elements responsible for minimum promoter activity are highlighted in bold, (see text for details). The run of CpA dinucleotide repeats in the mouse promoter is shown in bold and italic.

FIG. 6 shows details of the oligonucleotide primers hTR5 (SEQ ID NO: 3), hTR14 (SEQ ID NO: 4), hTR13F (SEQ ID NO: 5), hTR17F (SEQ ID NO: 6), hTR10F (SEQ ID NO: 7), hTR20F (SEQ ID NO: 8), hTR11F (SEQ ID NO: 9), hTR21F (SEQ ID NO: 10), hTR6F (SEQ ID NO: 11), hTR22F (SEQ ID NO: 12), hTR5 (SEQ ID NO: 13), hTR23R (SEQ ID NO: 14), hTRe (SEQ ID NO: 15), hTRf (SEQ ID NO: 16), hTRg (SEQ ID NO: 17), hTRh (SEQ ID NO: 18), TRC3F (SEQ ID NO: 19), and TRC3R (SEQ ID NO: 20) used for human, and mTR16F (SEQ ID NO: 21), mtr25f (SEQ ID NO: 22), mTR17F (SEQ ID NO: 23), mtr26f (SEQ ID NO: 24), mTR18F (SEQ ID NO: 25), mtr27f (SEQ ID NO: 26), mTR19F (SEQ ID NO: 27), mtr28f (SEQ ID NO: 28), mTR20F (SEQ ID NO: 29), mtr29f (SEQ ID NO: 30), mTRr1 (SEQ ID NO: 31), mtr30 (SEQ ID NO: 32), mTR36F (SEQ ID NO: 33), mTRr1 (SEQ ID NO: 34), and mTRf1 (SEQ ID NO: 35) for mouse sequences. The positions of these primers can be seen on the maps provided in FIGS. 7 and 8.

FIG. 9 shows the sequence for the TR gene promoter from Balb/c clones (SEQ ID NO: 38). The sequence analysis shows that the sequence is identical to that of the P1 sequence (FIG. 4B) apart from minor polymorphisms.

FIG. 11 shows the basal hTR promoter (−107 to +69, SEQ ID NO: 39). This 176 bp region termed sequence 2923, which contains several potential Sp1 transcription regulation sites, retinoblastoma control elements (RCE) and promoter CCAAT-box transcriptional regulator site. Sequence elements are defined in FIG. 12.

FIG. 12 shows oligonucleotides h11 (SEQ ID NO: 40), h111 (SEQ ID NO: 41), h112 (SEQ ID NO: 42), h113 (SEQ ID NO: 43), h11c (SEQ ID NO: 44), H11d (SEQ ID NO: 45), h111a (SEQ ID NO: 46), h112b (SEQ ID NO: 47), h112C (SEQ ID NO: 48), h11e (SEQ ID NO: 49), h10 (SEQ ID NO: 50), h101 (SEQ ID NO: 51), h10 m11 (SEQ ID NO: 52), h10 m2 (SEQ ID NO: 53), h9 (SEQ ID NO: 54), h91 (SEQ ID NO: 55), h910 (SEQ ID NO: 56), h911 (SEQ ID NO: 57), h92 (SEQ ID NO: 58), h921 (SEQ ID NO: 59), h93 (SEQ ID NO: 60), h930 (SEQ ID NO: 61), h4 (SEQ ID NO: 62), h41m (SEQ ID NO: 63), h5 (SEQ ID NO: 64), and h5m (SEQ ID NO: 65) used in the cloning and mutagenesis of the hTR promoter region.

FIG. 16 shows site-directed mutagenesis of the Sp1-1 binding region. It shows Sp1-1 (h9, SEQ ID NO: 54) is the critical region for the hTR promoter. A series of mutations were introduced into the h9 (SEQ ID NO: 54) region by 4 bp changes. Mutations are: h9 m1 (identical to h91, SEQ ID NO: 66), h9 m11 (identical to h911, SEQ ID NO: 67), h9 m2 (identical to h92, SEQ ID NO: 68), h9 m21 (identical to h921, SEQ ID NO: 69), and h9 m3 (identical to h93, SEQ ID NO: 70). Lane 1: no competitor. Lane 2: competition by Sp1-1 itself (h9). Lanes 3, 4, and 7: competition by h9 m1, h9 m11, and h9 m3. Lanes 5 and 6: no competition exhibited by mutations h9 m2 and h9 m21. This indicates that mutations h9 m2 and h9 m21 base pair regions are responsible for DNA-binding activity. Mutation of the TATA-box still competes with wild-type DNA-binding.

FIG. 17 concerns functional analysis of promoter mutants. It shows the scheme for introducing specific mutations into the hTR promoter. In brief, the mutant fragments were cloned into the luciferase basic vector, and the mutant confirmed by sequence. Mutant constructs were then transfected into 5637 cells to analyze luciferase activity. 5637 cells are a bladder carcinoma cell line which is p53 and pRb negative.

FIG. 19 concerns scanning mutation analysis of the hTR proximal promoter region (−107 to +69). It shows constructs with hTR promoter sequence with hTR promoter sequence elements mutations. The parental wild-type sequence (2923, SEQ ID NO: 39) and the mutant sequences 29 m23 (SEQ ID NO: 71), 1011 (SEQ ID NO: 72), 29 m292 (SEQ ID NO: 73), 29 m921 (SEQ ID NO: 74), 102 (SEQ ID NO: 75), 910 (SEQ ID NO: 76), 911 (SEQ ID NO: 77), 92 (SEQ ID NO: 78), 921 (SEQ ID NO: 79), 930 (SEQ ID NO: 80), 26n23 (SEQ ID NO: 81), 29111 (SEQ ID NO: 82), 29112 (SEQ ID NO: 83), 111 (SEQ ID NO: 73 & SEQ ID NO: 82), 112 (SEQ ID NO: 73 & SEQ ID NO: 83), 113 (SEQ ID NO: 84), 115 (SEQ ID NO: 85), and 114 (SEQ ID NO: 86) are shown below.

Figure 3A:
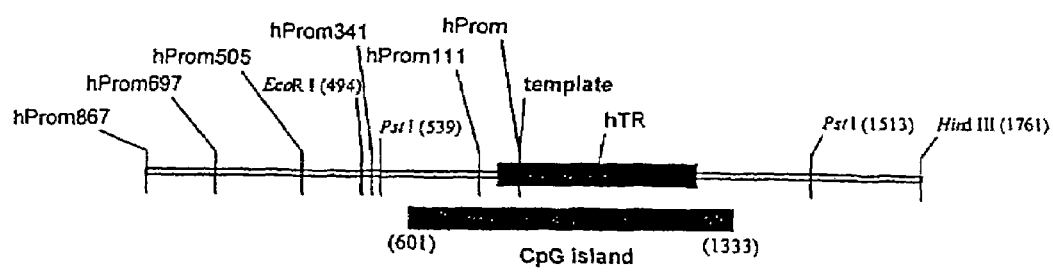
FIG. 3 shows the restriction enzyme map of the genomic clones encompassing the human and mouse telomerase RNA genes. A) show human telomerase RNA gene, hTR, genomic structure, 1765 bp; B) shows mouse telomerase RNA gene terc, genomic structure. The transcribed regions of hTR and terc are depicted as black boxes within the central regions of the genomic sequences and the site of the template sequence within the telomerase RNA genes is indicated. The position of the CpG islands are shown as a box beneath the genomic sequence. Numbers in brackets refer to the nucleotide position within the sequence. The 3'-end of all the human promoter fragments is shown as hProm and fragments extend 5' to hProm867, hProm697, hProm 341, and hProm111. The 3'-end of all the mouse promoter fragments is shown as mProm and fragments extend 5' to mProm 628, mProm458, mProm418, mProm267, mProm208, and mProm136. The numbers after the prefix, hProm or mProm refer to the number of nucleotides of genomic sequence contained in the promoter fragment.

First Trancriptional Unit
  hTR: telomerase RNA gene promoter
  PLAP: Placental Alkaline Phosphatase reported gene
  Tk: HSV thymidine kinase—sensitivity to ganciclovir
  Sh ble: Zeocin antibiotic resistance gene Second Trancriptional Unit
  hEF1-HTLV prom: elongation factor 1a & part of HTLV promoter
  codA::upp: bacterial cytosine deaminase & uracil phosphoribosytransferase—sensitivity to 5FU & 5-fluorocytosine.

DETAILED DESCRIPTION

Preparation of tissue sections for in situ hybridisation Formalin fixed paraffin embedded tissue blocks were obtained from Pathology Department files. Tissue sections were deparaffinised, rehydrated through graded concentrations of ethanol, (100%, 90%, 70%, 50%, 30% EtOH, 10 sec. each), rinsed in 0.85% sodium chloride for 5 minutes, followed by PBS for 5 minute. Sections were fixed in 4% paraformaldehyde/PBS for 20 minutes, rinsed in PBS, and treated with proteinase K (40 µg/ml) in 50 mM Tris-HCl pH 7.5, 5 mM EDTA for 7.5 minutes at room temperature. After rinsing for 5 minutes in PBS, sections were post fixed in 4% paraformaldehyde/PBS for 5 minutes, rinsed in water, and acetylated in freshly prepared 0.25% acetic anhydride/0.1M triethanolamine for 10 minutes. The slides were rinsed in 0.85% saline, followed by PBS for 5 minutes each and dehydrated in gradually increasing concentrations of ethanol prior to hybridisation.

Probe Preparation for In Situ Hybridisation

The riboprobe plasmid containing telomerase RNA sequences used for RNA in situ hybridisation is as previously described (Soder et al., 1997b). Control riboprobes were human histone H3 and glyceraldehyde 3-phosphate dehydrogenase (GAPDH), (Ambion, Tex.). The probes were labelled with ($^{35}$S)-UTP using a RNA labelling kit (Amersham, UK). Transcripts were purified using a Sephadex G-50 column (Pharmacia), phenol/chloroform extracted and precipitated in ethanol. The probes were resuspended in 50 mM dithiothreitol. Northern blot analysis of normal human tissue confirmed the specificity and sensitivity of the hTR probe to detect hTR expression in normal testis, (data not shown).

Hybridisation and Washing Procedures

Sections were hybridised overnight at 52° C. in 60% formamide, 0.3M NaCl, 10 mM Tris-HCl (pH 7.5), 5 mM EDTA, 10% dextran sulphate, 1× Denhardts (0.02% BSA, 0.02% Ficoll, 0.02% polyvinylpyrrolidone), 0.5 mg/ml yeast tRNA, 50 mM DTT (freshly added), and 50 000 cpm/ul $^{35}$S-labelled cRNA probe. The tissue was washed stringently at 50° C. in 5×SSC, 0.1% β-mercaptoethanol for 25 minutes, at 65° C. in 50% formamide, 2×SSC, 1% β-mercaptoethanol for 25 minutes, and washed twice at 37° C. in 0.5M NaCl, 10 mM Tris-HCl pH 7.5, 5 mM EDTA for 15 minutes before treatment with 20 µg/ml RNaseA at 37° C. for 30 minutes. RNase A only digests single stranded RNA. This removes single stranded, and therefore unhybridised probe, leaving the RNA:RNA duplexes intact. Thus this step helps reduce background probe signal. Following washes in 50% formamide, 2×SSC, 1% β-mercaptoethanol at 65° C. for 20 minutes, and twice in 2×SSC at 50° C. for 15, the slides were dehydrated and dipped in 0.1% gelatine/0.01% chromealun, and then in Hypercoat Nuclear LM-1 emulsion (Amersham) and exposed for 2 weeks in light tight boxes with desiccant at 4° C. The microautradiographs were developed in 20% Phenisol for 2.5 minutes, washed in 1% acetic and water each for 30 seconds, fixed in 30% sodium thiosulphate for 5 minutes, rinsed in water 30 minutes, and counter-stained with haematoxylin.

Cloning of Sequences Encompassing the Human and Mouse Telomerase RNA Genes

The present inventors have previously reported the identification of genomic clones in P1 vectors containing hTR and terc transcribed sequences (Soder et al., 1997b; Soder et al., 1997c). The human P1 clone, 9913, is derived fron a human foreskin fibroblast P1 library and the mouse P1 clone, 11792, is derived from a mouse C127 fibroblast P1 library. Briefly, in order to subclone the promoter regions, the P1 clones were digested with EcoRI and HindIII and ligated into pBluscript. Colonies containing telomerase RNA gene sequences were identified by hybridisation with PCR generated probes as previously described (Soder et al., 1997b; Soder et al., 1997c). Plasmid DNA was prepared from positively hybridising colonies, and inserts sequenced on both strands by dideoxy chain termination using the ABI PRISM dye terminator cycle sequencing kit (PE Applied Biosystems, Warrington, UK) and 25 ng oligonucleotide primers, Dye labelled products were resolved and detected using the Applied Biosystems DNA sequencer ABI373. Sequence was analysed using the Sequencing Analysis program 3.0. Homology searches were carried out using BLAST (Basic Local Alignment Search Tool), National Centre for Biotechnology Information (NCBI). Sequence was analysed for potential transcription factor binding sites by TESS: Transcription Element Search Software on the WWW, Jonathan Schug and G. Christian Overton, Technical Report CBIL-TR-1997-1001-v0.0, of the Computational Biology and Informatics Laboratory, School of Medicine, University of Pennsylvania. Identification of CpG islands was carried out using GRAIL: Gene Recognition and Assembly Internet Link, Computational Biology Section of the Life Science Division, Oak Ridge National Laboratory. The full sequences have been submitted to GenBank.

Construction of Luciferase Reporter Gene Constructs

The structures of the telomerase RNA gene-luciferase constructs used in the study are shown in FIGS. 5 and 4. Promoter-luciferase constructs were made by inserting PCR products into pGL3-Basic, (Promega). Orientation and sequence of each insert was checked by sequencing. Details of the primers are given in FIG. 6.

Transfection and Luciferase Assays

All transfections were carried out in duplicate in 6-well plates, (35 mm diameter). Cells were seeded at $6\times10^4$ cell per well and cultured overnight. Transfection was carried out using SuperFect Transfection Reagent, (Qiagen), according to the manufacturers instructions. Cells were exposed to the transfection mix for three hours and harvested for analysis after 48 hours. Equivalent amounts of cellular protein as determined by Bio-Rad assay, (BioRad), were used in the luciferase assay. Luciferase assays were performed according to the manufacturers protocols, (Promega). To ensure reproducibility in the assays, particular care was taken over the following: DNA used for transfection was quantified by spectrophotometry and direct visualisation by gel electrophoreses. All transfections were carried out in duplicate wells and this was found to be a good measure of the reproducibility of transfection. In each experiment, all deletion constructs were analysed together with both the basic cloning vector, pGL3-Basic and the positive control vector, pGL3-Control, which contains SV40 promoter and enhancer sequences. Each extract was measured for luciferase activity at least twice. All transfections were carried out at least three times. Initial transfection conditions were determined by using promoter fragments liked to a green fluorescent protein reporter gene, (Clontech), as this allowed direct visualisation of promoter activity in live cells, (data not shown). The present inventors found it important to transfect and analyse the cells at sub-confluence and that it was important to avoid harsh transfection protocols such as electroporation, resulting in poor cell viability.

Tumour Specific Regulation of Telomerase RNA Gene Expression Visualized by In Situ Hybridization.

The patterns of hTR expression were examined in epithelial cancer of lung, ovary, breast and cervix, (Table 1). Twenty six percent of non-small cell lung cancers, (NSCLC), were hTR positive. However, the NSCLC group consists of squamous, adenocarcinoma and large-cell anaplastic variants. Interestingly however, expression was almost exclusively limited to the squamous variants, (p=0.006), with 41% of squamous NSCLC expressing hTR but only 8% of adenocarcinoma and large-cell anaplastic NSCLC expressing hTR. This data suggests that hTR may be differentially regulated during the oncogenesis of squamous and non-squamous NSCLC. Indeed, the low frequency of detectable hTR expression in adenocarcinoma of the lung was also observed in adenocarcinomas of ovary and breast, (Table 1). In addition, metastatic carcinoma in hilar lymph nodes of 19 of the NSCLC cases were available for a comparative study with the paired primary carcinomas. All 6 cases which expressed hTR in the primary carcinoma retained expression in the metastasis and all 13 primary carcinomas which lacked detectable hTR expression remained negative in the metastasis, (Table 1). Thus, expression levels appear stable between primary and metastatic carcinomas and expression of hTR is not associated with metastasis of pulmonary carcinomas.

Cancer of the uterine cervix is a heterogeneous group of lesions, which like NSCLC can be subdivided into squamous and adenocarcinoma (Benda, 1994). The present inventors studied 87 cervical lesions for hTR expression, (Table 1). hTR expression was detected in 44% of the cervical carcinomas, however in contrast to NSCLC, there was no significant difference in frequency of expression between invasive squamous carcinoma, (44%), and invasive adenocarcinoma, (32%). The data for adenocarcinoma of the cervix also contrast those for invasive adenocarcinoma of the breast, (13%), and ovary, (17%), (Table 1), and suggest that regulation of hTR expression may be different for cervical cancer and therefore relate to the aetiology of the disease (Benda, 1994; Klingelhutz et al., 1996). Interestingly, hTR expression was readily detected in preinvasive cervical cancer, (40%, see Table 1), and there was no significant difference in frequency between invasive and preinvasive lesions. In addition, the case of glandular intraepithelial neoplasia of the cervix has heterogeneous expression of hTR (data not shown), thus allowing the evolution of hTR expressing cells to be followed in their histological context.

The primitive germ cells of the male are found in the seminiferous tubules and the present inventors examined 22 sections from normal testis and uninvolved tubules from testicular cancer patients to establish the pattern of hTR expression in normal seminiferous tubules, (data not shown). Of the 22 sections, 21 showed hTR expression in the primitive germ cells located in the basal layers of the seminiferous epithelium, (Table 1). The intimate relationship between germ cells and the supportive Sertoli cells, means that expression of hTR in the Sertoli cells cannot be excluded. Mature germ cells (spermatids and spermatazoa) when present, did not express hTR. Thus, the in situ assay can detect normal levels of hTR expression in primitive germ line stem cells and the distribution of hTR expression in the testis is consistent with its proposed role in the maintenance of telomere length in the germ line. A series of 22 testicular germ cell tumours were also analysed for hTR expression. As shown in Table 1, 73% of testicular germ cell tumours were positive for hTR expression, and there was no significant difference between teratomas and seminomas of the testis. Interestingly, within hTR-positive teratomas, mature tissues never had detectable hTR expression whatever their differentiation. Similarly, 15 benign ovarian teratomas composed of fully mature differentiated tissues had no detectable hTR expression, (Table 1). Thus, the differentiated teratomas may recapitulate the down regulation of hTR during early embryonic or foetal development, (Wright et al., 1996). In five of the testicular seminomas there was no detectable hTR expression, (Table 1), but in each seminoma case, germ cells within adjacent normal seminiferous tubules expressed hTR, suggesting either that hTR expression has been repressed during oncogenesis, or that seminomas without detectable levels of hTR arise from germ cells with low or no hTR expression.

TABLE 1

Frequency of hTR expression.

| Tumour | Tissue histology | Frequency | % |
|---|---|---|---|
| Testicular Germ Cell Tumours | normal testicular germ cells | 21/22 | 95 |
| | [a]teratoma | 7/8 | |
| | seminoma | 8/13 | |
| | intratubular | 1/1 | |
| | Total | 16/22 | 73 |
| Ovarian Germ Cell Tumours | [b]benign ovarian teratomas | 0/15 | 0 |
| Non-small Cell Lung Cancer | squamous | 13/32 | 41 |
| | adenocarcinoma (18)/large cell (7) | 2/25 | 8 |
| | [c]Total | 15/57 | 26 |
| Epithelial Ovarian Cancer | [d]adenocarcinoma | 6/34 | 17 |
| Breast Cancer | [e]invasive adenocarcinoma | 7/54 | 13 |
| | ductal carcinoma in situ, (DCIS) | 0/19 | 0 |
| | [f]DCIS, recurrent | 1/4 | |
| | Phylloides | 0/6 | |
| | Total | 8/83 | 10 |
| Cervical Cancer | invasive squamous | 15/34 | 44 |
| | invasive adenocarcinoma | 7/22 | 32 |
| | [g]invasive adenosquamous | 7/11 | |
| | Invasive Total | 29/67 | 43 |
| | squamous intraepithelial neoplasia | 4/5 | |
| | glandular intraepithelial neoplasia | 2/10 | |
| | [h]mixed squamous/glandular | 3/5 | |
| | intraepithelial neoplasia Preinvasive Total | 8/20 | 40 |
| | [i]All cervix samples | 38/87 | 44 |

TABLE 1-continued

Frequency of hTR expression.

| Tumour | Tissue histology | Frequency | % |
|---|---|---|---|
| Metastasis: Non-small Cell Lung Cancer | positive in primary & metastasis negative in primary & metastasis | 6/6 13/13 | |

Table 1. Frequency of hTR expression.
[a]The single teratoma without detectable hTR expression was of intermediate maturity and also expressed GAPDH, (data not shown), and therefore the lack of expression is not due to loss of RNA from the sample.
[b]To test for RNA integrity in the ovarian teratomas, a group of 6 were analysed for GAPDH expression and all were found to be positive.
[c]A group of 33 NSLC were tested for histone H3 expression, 22 of which did not have detectable levels of hTR expression and all 33 were positive An additional 4 hTR negative NSCLC samples tested for GAPDH expression were positive.
[d]Two ovarian cancers, (1 hTR negative), were tested for histone H3 expression and both were positive.
Three ovarian cancers were tested for GAPDH expression and all were positive.
[e]A group of 10 invasive breast cancers, (7 hTR negative), were tested for histone H3 expression and all were positive.
In addition, 11 breast cancers lacking detectable levels of hTR expression were tested and were positive for GAPDH expression.
[f]Four specimens of DCIS were obtained from patients who had in the previous 5 years been diagnosed and treated for the presence of preinvasive breast cancer, (DCIS).
The primary biopsies for all 4 were lacking detectable levels of hTR expression, however one recurrent DCIS biopsy had detectable hTR expression.
[g]Adenosquamous cancers of the cervix.
Where samples were positive for hTR expression, all elements were positive.
[h]Preinvasive cervical cancer.
In lesions with mixed glandular and squamous elements, where samples were positive for hTR expression, all elements were positive.
[i]Two cervical cancers, (1 lacking detectable levels of hTR expression), were tested for histone H3 expression and both were positive.
Three cervical cancers were tested for GAPDH expression and all were positive.
In total, 28 samples, (25 lacking detectable levels of hTR expression), were tested and were positive for GAPDH expression and 47 samples, (31 lacking detectable levels of hTR expression), were tested and were positive for histone H3 expression.
Visual inspection suggested that histone H3-positive cells were present in comparable numbers in the carcinomas lacking detectable levels of hTR expression and in the hTR positive carcinomas.
The same areas of tissue were examined for both hTR and histone H3 expression, thus, the lack of detectable hTR expression is unlikely to be due simply to the presence of quiescent cells in the tumours, (Holt et al., 1996b).

Cloning of Genomic Sequences Encompassing the Human and Mouse Telomerase RNA Genes.

Figure 3B:
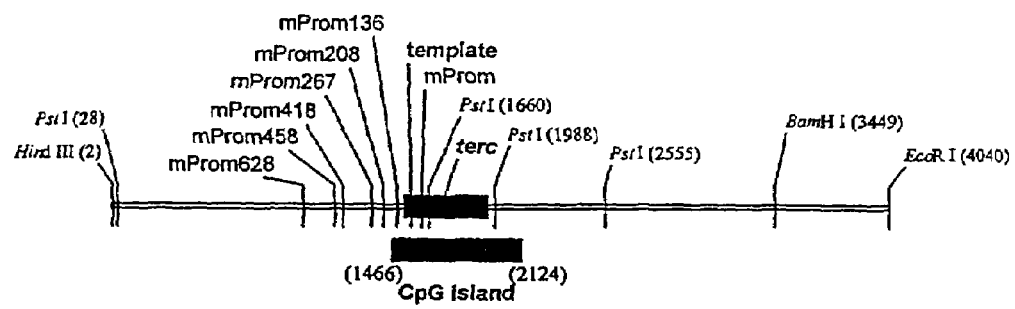

In order to obtain sequences flanking the genes, the P1 genomic clones were digested with EcoRI and HindIII, subcloned into the plasmid vector, pBluescript, and colonies containing hTR or terc sequences identified by hybridisation to PCR generated probes specific for the genes. A 1.3 kb genomic clone encompassing hTR was isolated as was a 4 kb genomic clone encompassing terc, (FIG. 3).

A BLAST search using the 1.3 kb human sequence identified three high-scoring segment pairs: HSU85256, HSU86046 and MMU33831. HSU85256, (598 bp of sequence), and HSU86046, (545 bp of sequence), are published sequences for the transcribed region of the human telomerase RNA gene and confirmed that we had cloned genomic sequences encompassing hTR (Bryan et al., 1997; Feng et al., 1995). MMU33831 is the sequence of the transcribed region of the mouse telomerase RNA gene which has previously been shown to have homology to the human gene (Blasco et al., 1995).

A BLAST search using the 4 kb mouse sequence identified both the published human gene sequences, (HSU85256, HSU86046), and the published sequence for the transcribed region of the mouse gene, MMU33831, (591 bp of sequence) (Blasco et al., 1995; Bryan et al., 1997; Feng et al., 1995). In order to confirm that the genomic sequence obtained from the P1 subclone was genuine, the present inventors cloned 5'-flanking sequences using genomic DNA from Balb/c mice in PCR reactions. Sequence analysis of the Balb/c clones were identical to the P1 sequence except for minor polymorphism's, (FIG. 9). A schematic representation of the 4 kb of sequence information encompassing the mouse telomerase RNA gene is shown in FIG. 3.

Analysis of Nucleotide Sequence Encompassing the Human and Mouse Telomerase RNA Genes.

To investigate the relationship between the human and mouse genomic clones, sequence comparisons were carried out. The transcribed regions of the two genes showed 67% identity in keeping with the published estimate, (Feng et al., 1995). However, no significant sequence identity could be identified in either the 5'- or 3'-regions flanking the transcribed sequences.

Both the human and mouse sequences were analysed for CpG islands by GRAIL. CpG islands were defined as regions larger than 200 bp, with an average GC content greater than 50% and the ratio of observed versus expected CpGs greater than 0.6 (Gardiner-Garden & Frommer, 1987). Interestingly, both the human and mouse genes lie within CpG islands, (see FIG. 3). The human gene is covered by a CpG island 733 bp in length, with a GC content of 66% and a ratio of observed versus expected CpGs of 0.89. The mouse gene is covered by a CpG island of 659 bp in length, with a GC content of 64% and a ratio of observed versus expected CpGs of 0.81.

The 5'-flanking regions of the human and mouse telomerase RNA genes were also analysed for potential transcription factor recognition sites. As shown in FIG. 4, a number of potential binding sites can be identified, including consensus sequences for glucocorticoid/progesterone/androgen receptor binding, AP1 and Ets family members. CCAAT box's are found in both genes close to the published transcriptional start sites (Blasco et al., 1995; Feng et al., 1995), however, there is no obvious TATA box in the mouse gene with the human gene TATA box consensus sequence being in the reverse orientation. The mouse promoter region also contains a run of CpA dinucleotide repeats which may be of use in developing microsatellite genetic markers for this gene.

Transfection Assays Detect Promoter Activity in the 5'-Flanking Regions of the Human and Mouse Telomerase RNA genes.

To identify whether the 5'-flanking DNA of the telomerase RNA genes exhibited promoter activity, sequences were fused to a firefly luciferase reporter gene, (pGL3-Basic). The transcriptional start sites for both the human and mouse telomerase RNA genes have been established (Blasco et al., 1995; Feng et al., 1995). Various promoter constructs containing the transcriptional start site were therefore generated, (see FIGS. 4, 5).

Figure 5A:
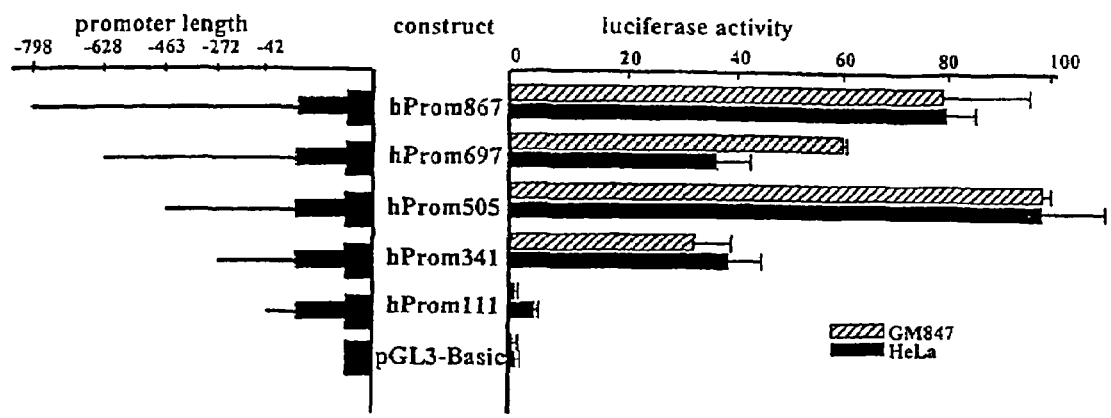
FIG. 5 shows the detection of promoter activity in the 5'-flanking regions of human and mouse telomerase RNA genes. For each construct, the length of sequence upstream from the transcriptional start site is shown to the left and the luciferase activity to the right. A) Diagram comparing luciferase activity from human promoter constructs in GM847 and HeLa cells. Data from each construct is plotted as a percentage of the hProm505 luciferase activity as this construct consistently gave the highest activity in human cells. For each construct the mean and standard deviation for duplicate transfected wells is shown. B) Diagram comparing luciferase activity from mouse promoter constructs in SWISS3T3 and A9 cells. Data for each construct is plotted as a percentage of the mProm458 luciferase activity as this construct consistently gave the highest activity in mouse cells. For each construct the mean and standard deviation for duplicate transfected wells is shown.

Human promoter constructs containing truncated portions of the 5'-flanking region were transiently transfected into HeLa and GM847 cells, (FIG. 5a). HeLa is a telomerase positive cervical carcinoma cell line, GM847 is a SV40-immortalised skin fibroblast cell line which expresses the telomerase RNA component but is telomerase-negative, (Bryan et al., 1997). As shown in FIG. 5a, promoter activity was observed in both cell lines with fragments containing 341 bp or more, (from position –272, see FIGS. 4a, 5a). The highest luciferase activity was observed with construct hProm505 which contains a 505 bp fragment, (position –436, see FIG. 4). Construct hProm111, which contains only 111 bp of 5'-flanking sequence (position –42 see FIGS. 4a, 5a), produced a dramatically reduced level of luciferase activity (FIG. 5a). Thus a minimal promoter sequence can be defined as extending 272 bp upstream of the transcription start site, and that elements responsible for promoter activity must be contained in a 231 bp region between –272 bp and –42 bp (FIGS. 4a and 5a).

Figure 5B:
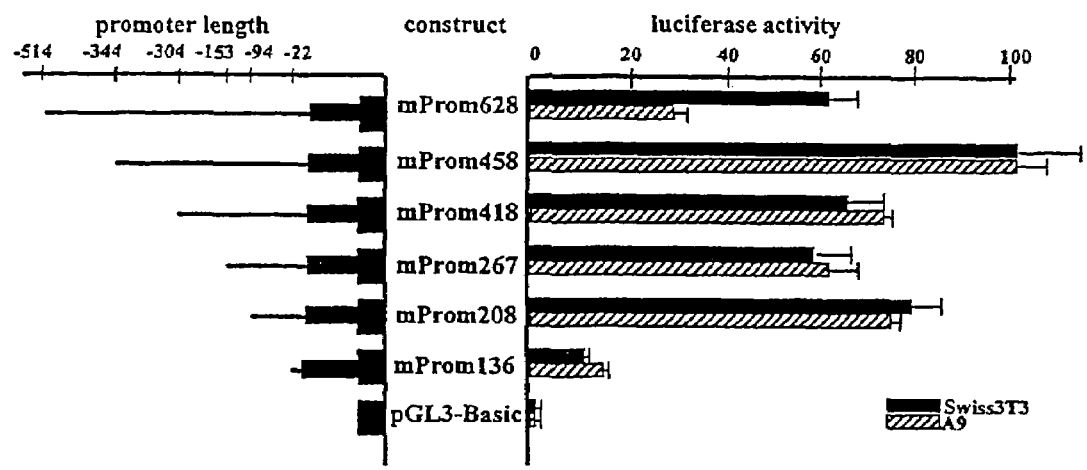
Figure 7A:
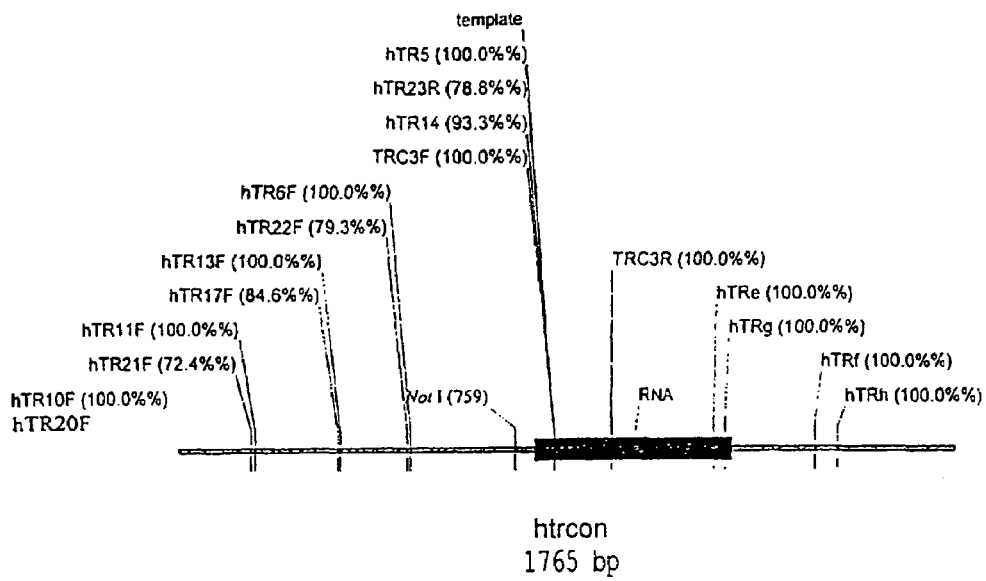
FIG. 7 A) shows a map of the 1765 bp hTR construct with the position of primers (see FIG. 6) shown. In each case the percentage homology of the primer is indicated. B) shows a map of the 1765 bp hTR construct with the restriction sites marked.
Figure 7B:
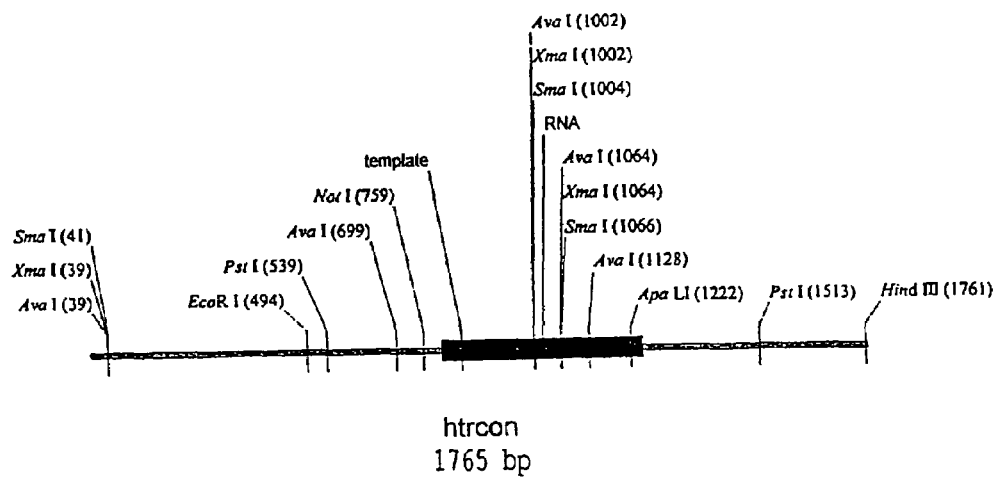
Figure 8A:
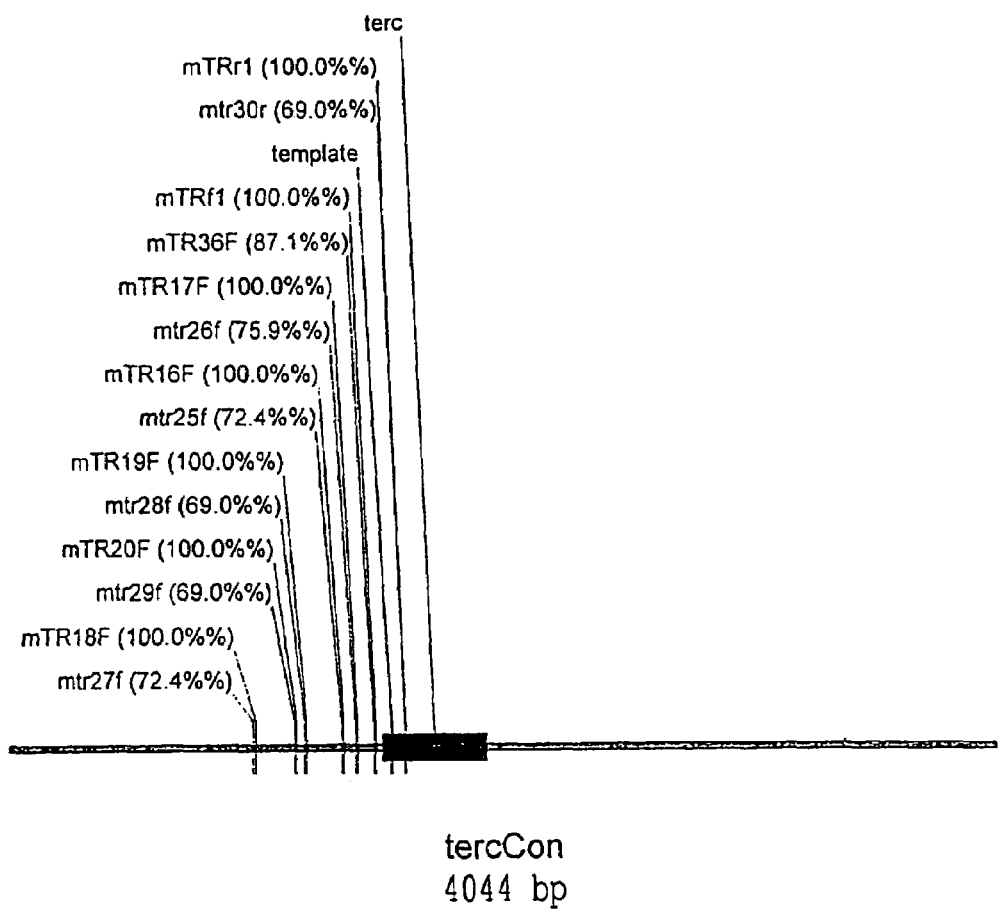
FIG. 8 A) shows a map of the 4044 bp mouse terc construct with the position of the primers (see FIG. 6) shown. In each case the percentage of homology of the primer is indicated. B) shows a map of the 4044 bp terc construct with the restriction sites marked.
Figure 8B:
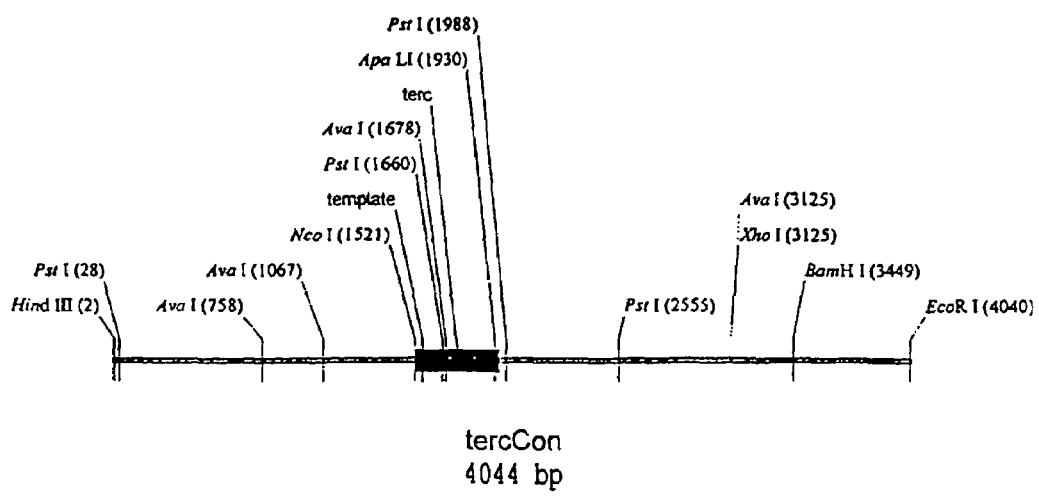
Figure 10:
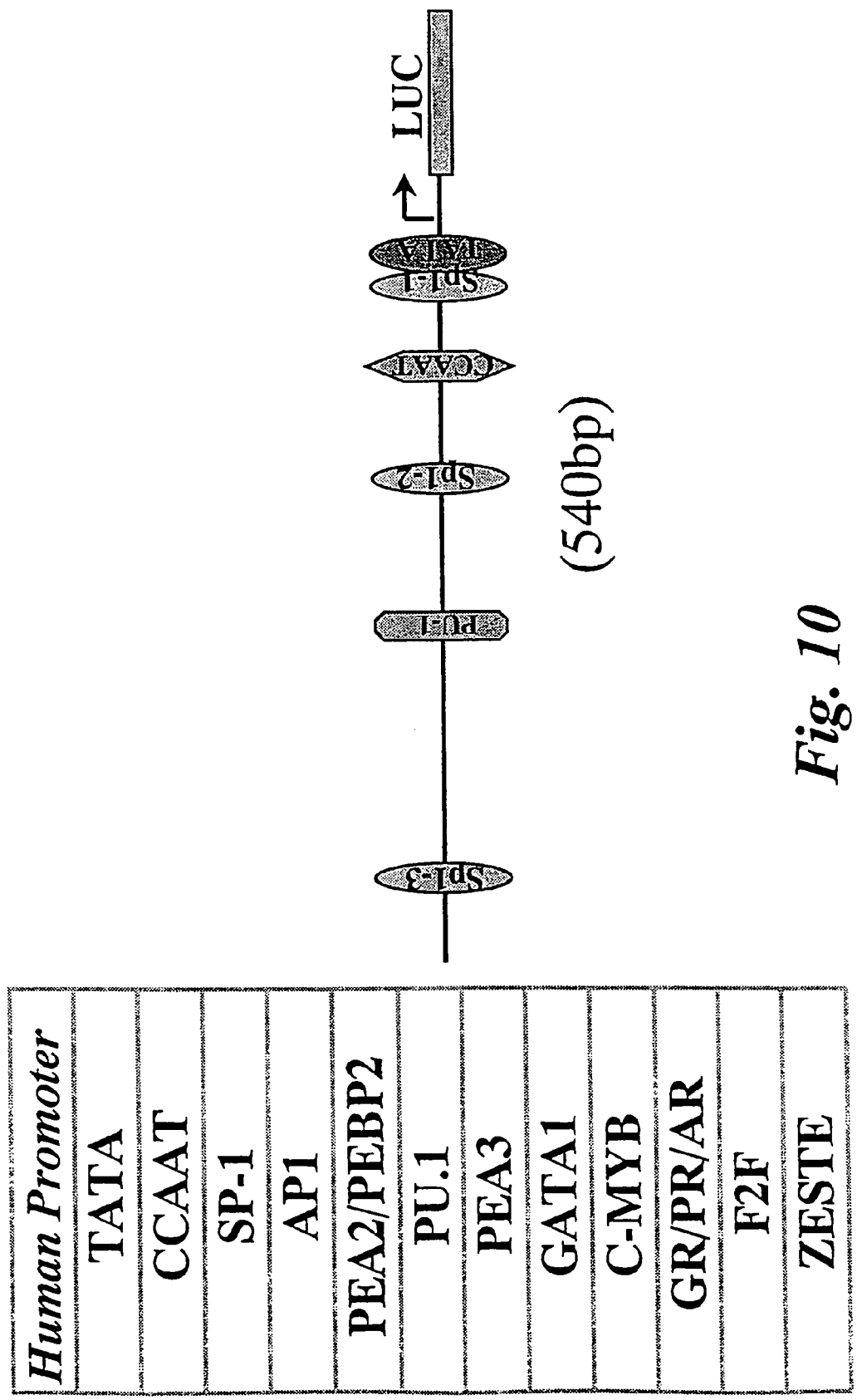
FIG. 10 shows potential transcription factor binding sites with the hTR promoter.

Mouse promoter constructs containing various truncated portions of the 5'-flanking region were transiently transfected into SWISS3T3 and A9 cells, (FIG. 5b). SWISS3T3 cells are an embryo derived line and A9 cells are of areolar and adipose origin. Both cell lines are telomerase positive. As shown on FIG. 5b, promoter activity was observed in both cell lines with fragments containing 208 bp or more, (from position –94, see FIG. 4b). Construct mProm136, which contains only 136 bp of 5'-flanking sequence, (position –22, see FIG. 4b), produced dramatically reduced levels of luciferase activity, (FIG. 4b). Thus, a minimal promoter sequence can be defined as extending 94 bp upstream of the transcription start site, and that elements responsible for promoter activity must be contained in a 73 bp region between –94 bp and –22 bp, (FIGS. 4b and 5b).

Transfection of the human promoter construct hProm867 into mouse cells gave very strong promoter activity, with up to twice that of the strongest mouse construct, and transfection of the mouse promoter construct, mProm628 into human cells also showed luciferase activity at around 25% of the strongest human construct, (data not shown).

Identification of Transcription Factor Binding Sites in the hTR Promoter by Gel Shift Assays In order to identify the key sequence elements involved in transcription factor binding, protein extracts from cell lines were assayed for their ability to detect specific DNA sequence elements within the hTR promoter by gel shift assays. Fluorescence assays may also be used and detected by microscopy, microplate reader or cytometry. Such elements are then considered candidates for regulating hTR in vivo. These studies concentrated on the 176 bp region of the hTR promoter shown in FIG. 11 as part of the sequence shown in FIGS. 1 and 4a. This 176 bp region is termed sequence 2923 and contains several potential Sp1 transcription regulation sites, retinoblastoma control elements, (RCE) and the promoter CCAAT-box transcriptional regulator site, (see FIG. 11). The oligonucleotide sequence elements used in the analysis of transcriptional regulation are shown in FIG. 12.

Identification of Protein Interaction with the CCAAT Sequence Element.

Figure 13:
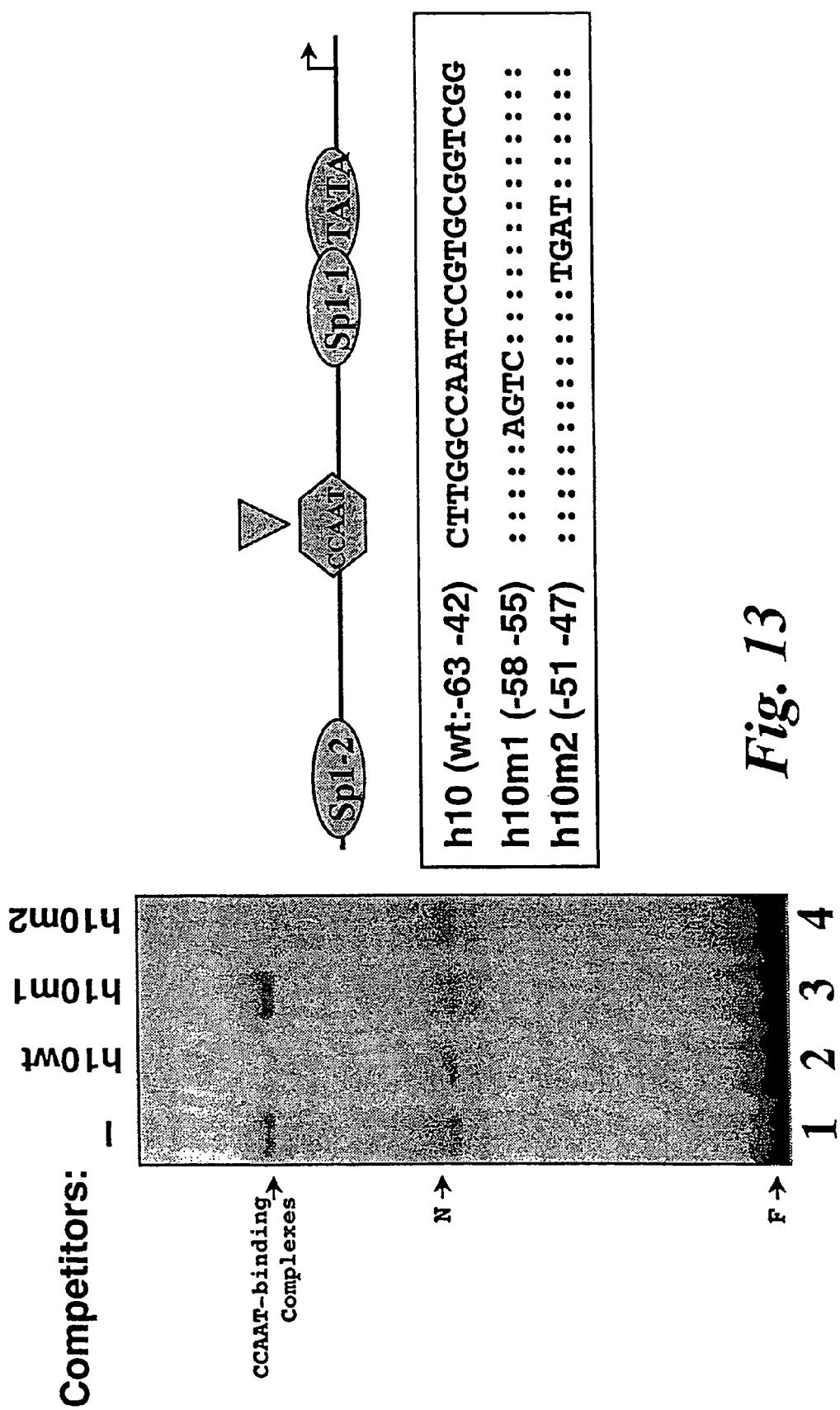
FIG. 13 concerns mutagenesis of the CCAAT-binding site. It shows a gel shift assay with the h10 sequence for the CCAAT-binding site. The h10 sequence (SEQ ID NO: 50) can bind to the HeLa nuclear extract protein and be competed with itself (h10). Mutation h10 m1 (identical to h101, SEQ ID NO: 51) does not compete with oligonucleotide h10, whereas h10 m2 (SEQ ID NO: 52) still competes. The CCAAT site was mutated from CCAA to AGTC leading to loss of binding activity. This suggests that the CCAAT site is a functional region for DNA-binding proteins.

A CCAAT box element is found upstream of the transcriptional start site for hTR, (see FIG. 11). In order to identify whether cellular proteins interact with this site in the hTR promoter, protein extract from the HeLa cell line was used in an electophoretic mobility shift assay, (EMSA) with oligonucleotide sequence elements corresponding to the normal wild type hTR sequence termed h10 in FIGS. 12 & 13, (see FIGS. 11, 12 & 13). FIG. 13 shows that the h10 oligonucleotide sequence containing the hTR CCAAT-box can bind proteins in a specific fashion as competition for binding with the h10 oligonucleotide sequence itself aboloshes the complex as does an oligonucleotide with mutations outside the CCAAT region, (see sequence h10 m2, FIGS. 12 & 13). Addition of oligonucleotide sequences with mutations intoduced into the CCAAT site cannot compete for protein binding, (sequence h10m1 in FIGS. 12 & 13). This suggests that the CCAAT-box sequence element is a functional region for DNA binding proteins and may regulate the hTR promoter.

Identification of Two Sp1 Sequence Elements in the hTR Promoter.

Figure 14:
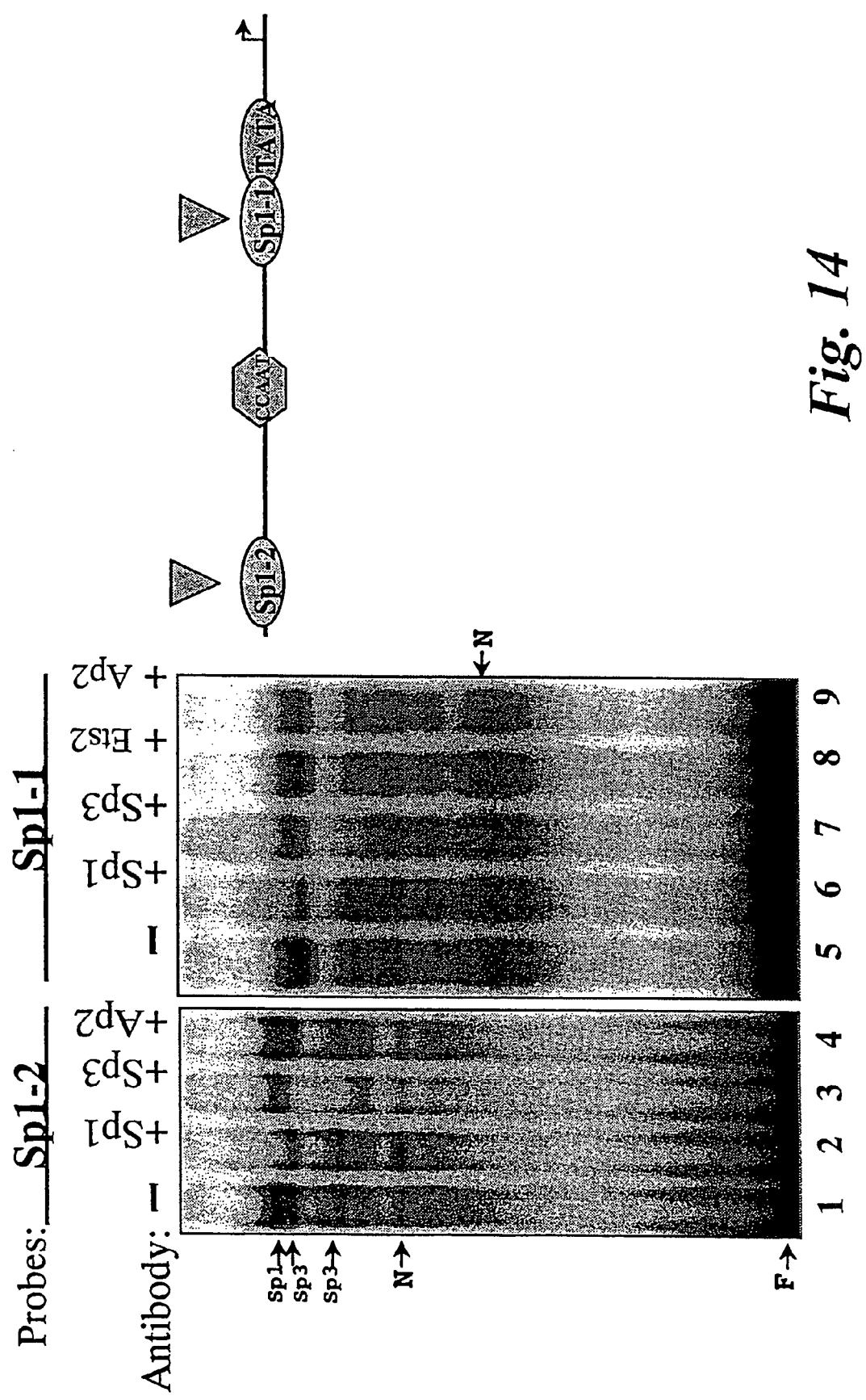
FIG. 14 shows nuclear factors binding to the Sp1 sites in the hTR promoter. Two separate DNA regions can be recognized by HeLa protein extracts and produce one Sp1 (top) band-shift, and two Sp3 (bottom) band shifts. This shows two Sp1 binding sites present in the proximal hTR promoter region.
Figure 15:
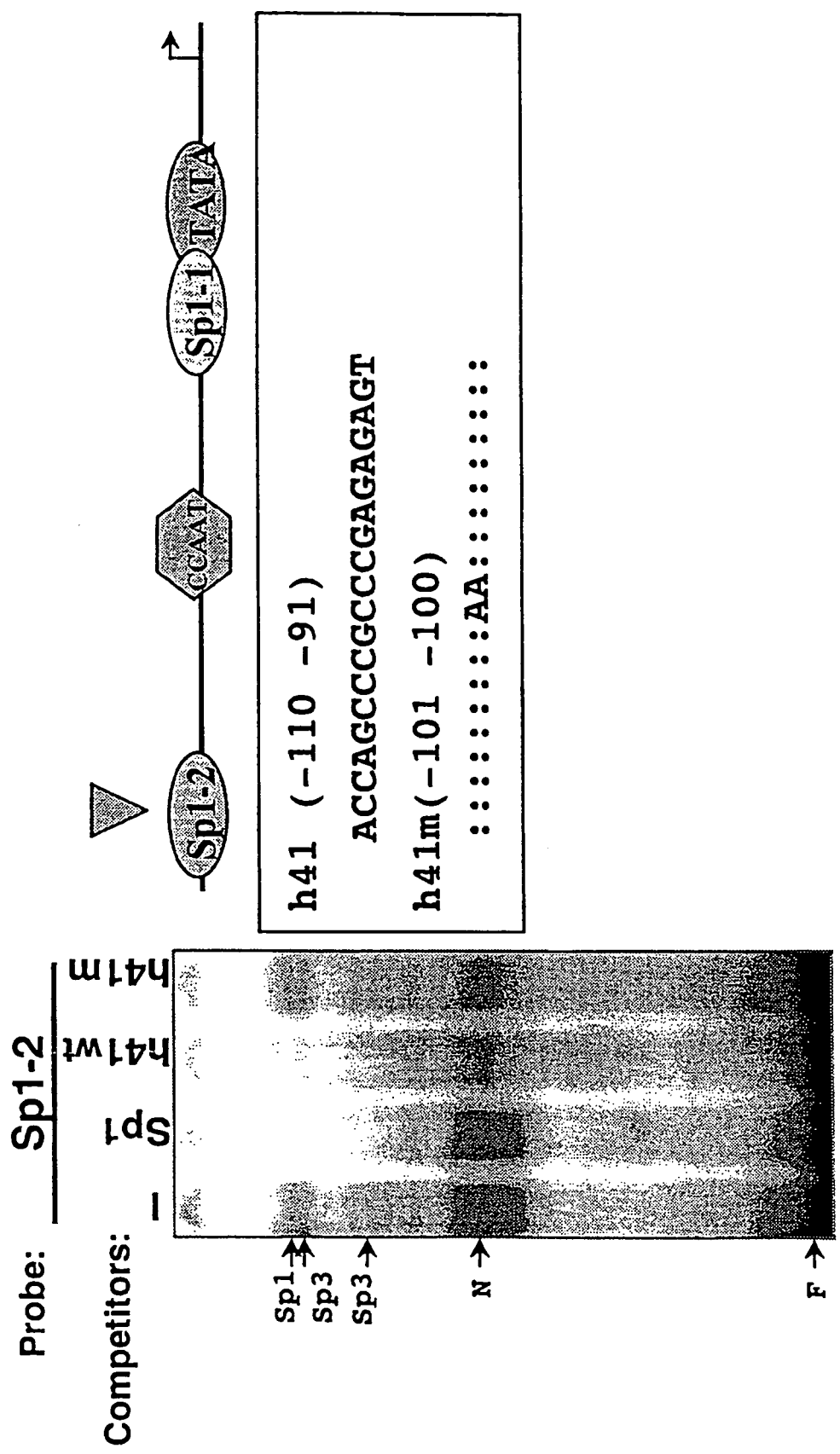
FIG. 15 shows site-directed mutagenesis of the Sp1-2 binding sites. It shows that specific Sp1 binding can be blocked by two bp nuclear changes in the Sp1-2 (h41, identical to h4, SEQ ID NO: 62) sequence. Lane 1: no competitor. Lane 2: competition by Sp1 consensus sequence. Lane 3: competition by Sp1-2 (h41) itself. Lane 4: no competition exhibited by mutation h41m (SEQ ID NO: 63).

Two Sp1 sequence elements are found upstream of the 25' hTR transcriptional start site, (FIG. 11). In order to identify whether cellular proteins interact with these sites in the hTR promoter, protein extract from the HeLa cell line was used in an electophoretic mobility shift assay, (EMSA) with oligonucleotide sequence elements corresponding to the normal wild type hTR sequences termed h4, (Sp1-2, see FIGS. 11 & 12), and h9, (Sp1-1, see FIGS. 11 & 12). As can be seen from FIGS. 14, 15, 16, hTR promoter sequence containing Sp1-1 and Sp1-2 sequence elements form DNA/protein complexes characteristic of binding of Sp1 and Sp3 transcription factors. This suggests that the hTR promoter may be regulated by the Sp family of transcription factors.

Functional Analysis of hTR Promoter Sequence Elements in Cell Lines

The gel shift assays discussed above identified a number of sequence elements which form specific DNA/protein complexes which may regulate the activity of the hTR promoter. In order to confirm these sequence elements function in the regulation of the hTR promoter in vivo, mutations were introduced into these sites within the context of the basal promoter region of the hTR gene. The ability of these mutations to drive the hTR promoter in comparison to the wild type promoter sequence was then analysed. The overall scheme of this approach is shown in FIG. 17.

Figure 18:
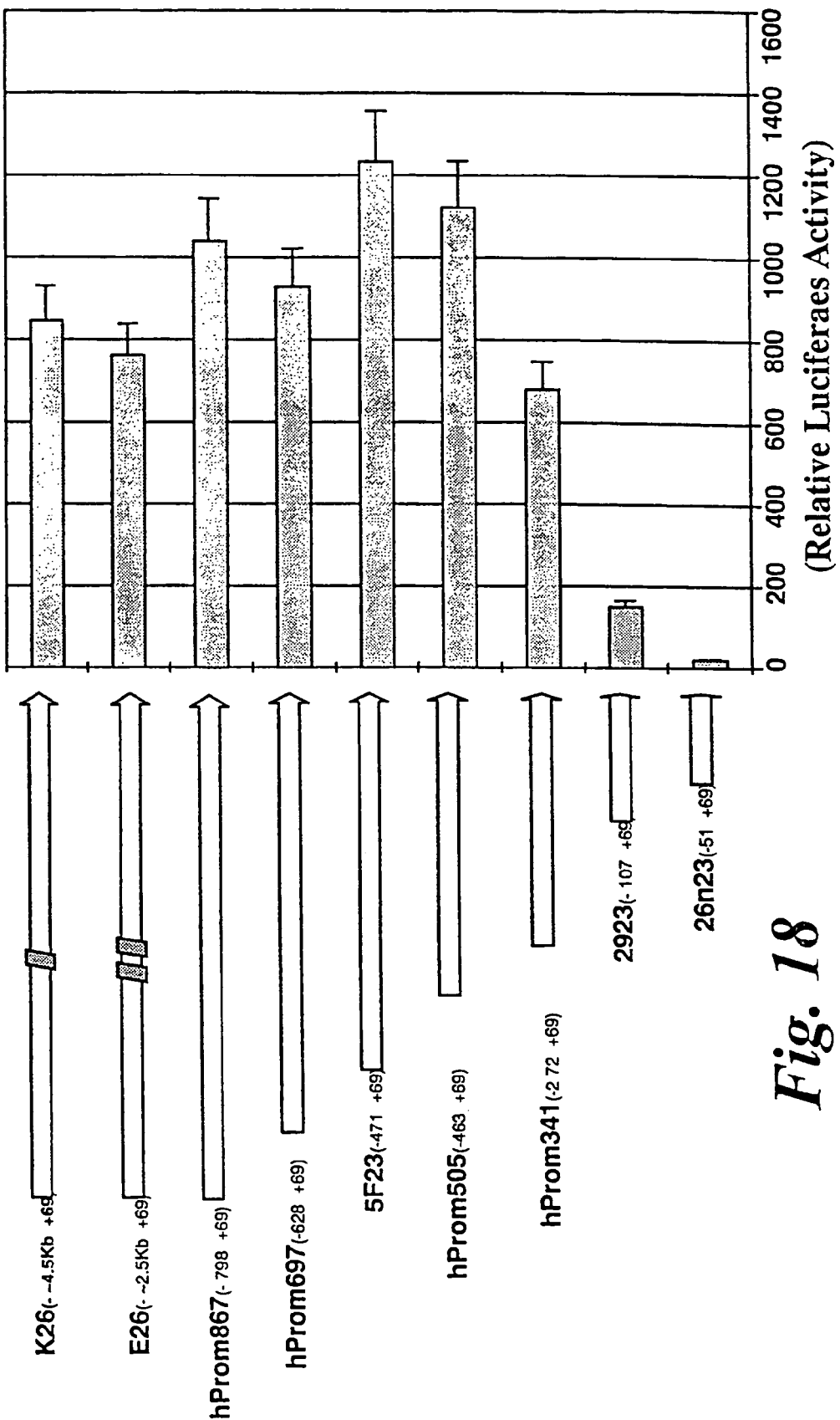
FIG. 18 shows deletion analysis of the 5'-flanking region of the hTR gene in HeLa cells. The wild-type promoter sequence used in this study is the hTR 2923 (SEQ ID NO: 39) shown in FIG. 11. The promoter activity of this clone relative to the previously described promoter clones (FIG. 5A) is shown.
Figure 20:
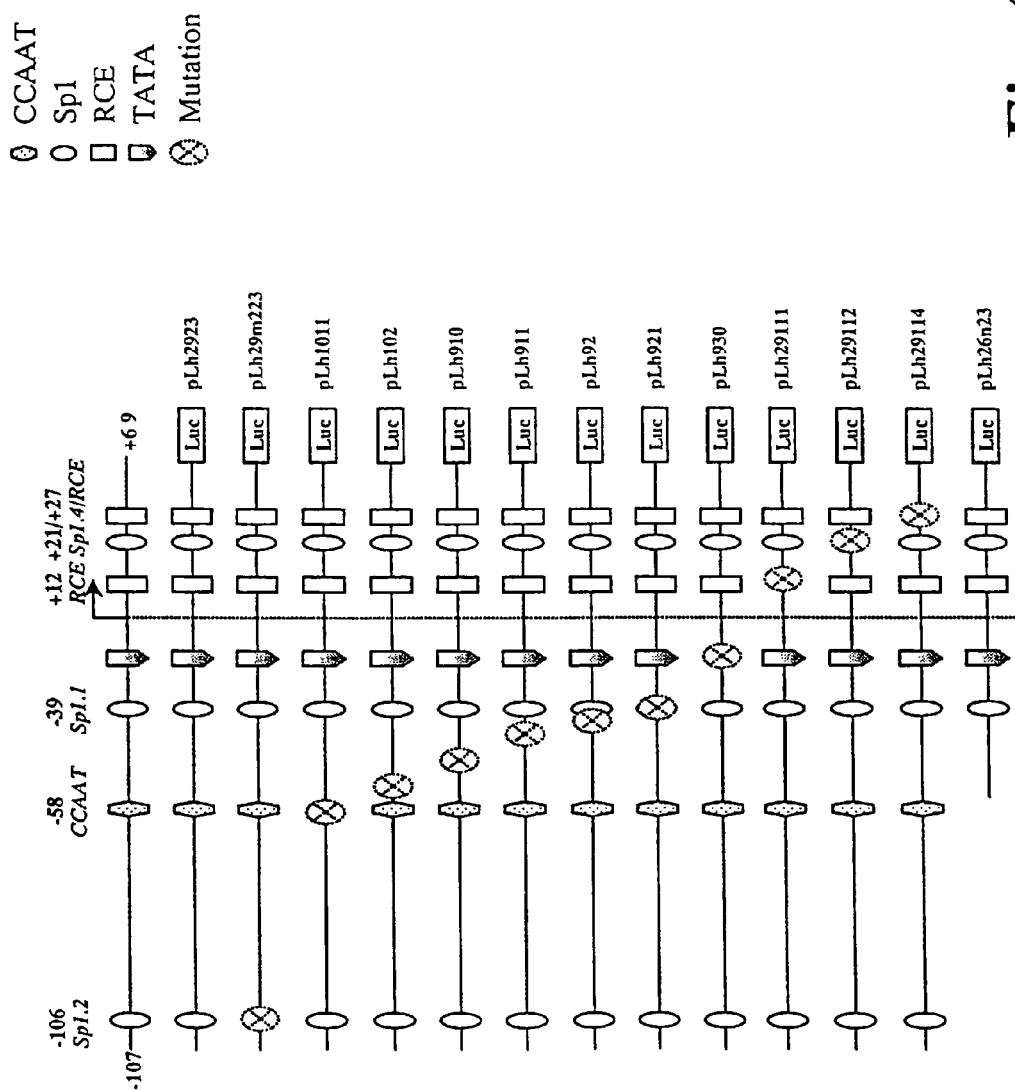
FIG. 20 shows a diagrammatic version of the mutant promoter constructs described in FIG. 19, which were used to assay for promoter activity.
Figure 21:
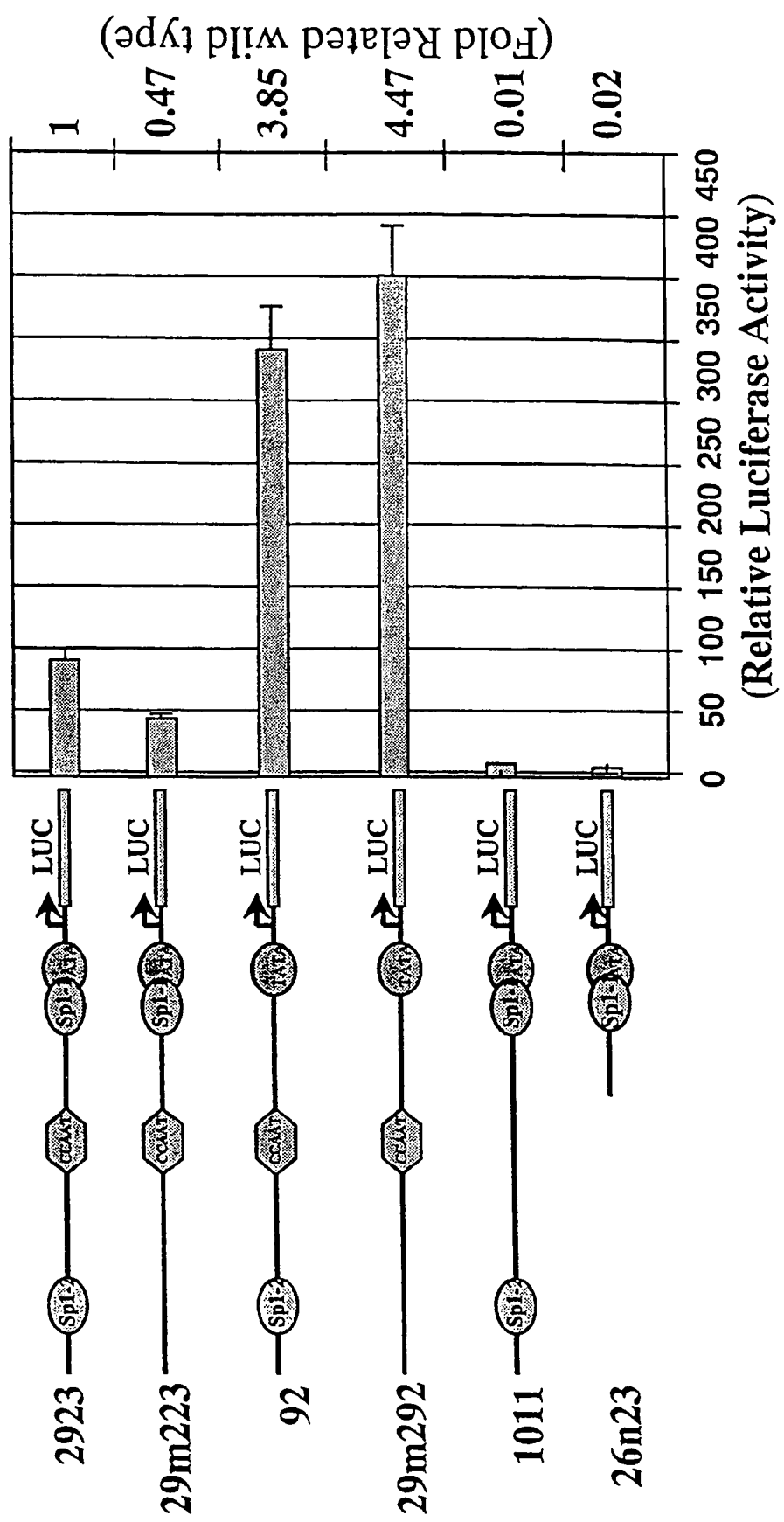
FIG. 21 concerns mutation analysis of the hTR promoter in 5637 cells. It shows the ability of the mutant promoters to drive gene expression in comparison to the wild-type promoter sequence in cell lines. The left side shows the mutation constructs, the right side shows luciferase activity relative to the wild-type (2923). Mutation Sp1-1 decreases the basal activity. Mutation Sp1-1 or both Sp1 and Sp1-2 significantly increase the basal activity about 4 to 4.5 fold. Mutation CCAAT site abolished promoter activity completely. This result suggests that CCAAT-binding factor is essential element for basal hTR promoter activity. Two Sp1 elements involved in the hTR gene regulation. Sp1-1 is a site for negative regulation.

The wild type promoter sequence used in this study is the hTR 2923 sequence shown in FIG. 11. The promoter activity of this clone relative to the previously described promoter clones, (see FIG. 5a), is shown in FIG. 18. In order to analyse the function of hTR promoter sequence elements in cell lines, constructs with hTR promoter sequence element mutations were made and these are shown in FIGS. 19 & 20. The ability of the mutant promoters to drive gene expression was assayed in comparison to the wild type promoter sequence in cell lines as shown in FIG. 21. FIG. 21 shows firstly that mutation of the Sp1-2 sequence element reduces promoter activity, (construct 29 m223), sugesting this element is the site of action for an activator of the hTR promoter; secondly that mutation of the Sp1-1 sequence element significantly increases basal promoter activity by 4–4.5 fold, (construct 92 and 29 m292), sugesting this element is the site of action for an inhibitor of hTR promoter activity; and thirdly that mutation or deletion of the CCAAT sequence element abolishes hTR promoter activity, (costruct 1011 & 26n23), suggesting this element is the site of action for an activator of hTR promoter activity.

Thus the inventor has identified key regulatory sequence elements involved in hTR promoter activation and repression.

Identification of Genes Modulating hTR Promoter Activity

In order to identify genes regulating telomerase RNA gene expression, candidate genes are transfected into cell lines containing the hTR promoter/reporter constructs. Fluctuations in reporter activity due to candidate genes can are monitored and conclusive evidence presented for their activity.

The analysis of hTR sequence elements presented above sugests the involvement of the Sp family of transcription factors in regulation of the hTR promoter. Therefore, the inventor co-transfected into cell lines the luciferase reporter gene under control of the hTR promoter together with expression vectors for the following three transcriptional regulators: Sp1, Sp3, and pRb.

The transcriptional regulators Sp1 and Sp3 both recognise the same DNA sequence, the so called Sp1 site. Transcriptional regulation by the Sp family of proteins is complex, but in general Sp1 activates genes whereas Sp3 can repress promoter activity. The retinoblastoma gene product, pRb, is classically thought of as a tumour suppressor gene and has numerous roles as a modulator of gene transcription and cell cycle regulator. The Rb gene was the first tumour suppressor gene to be cloned. pRb has roles in: mediating transcriptional repression of RNA polymerase II, (Pol II), transcribed promoters; mediating transcriptional repression of RNA polymerase III, (Pol III), transcribed promoters; mediating transcriptional activation of RNA polymerase II, (Pol II), dependant promoters. This last role in mediating transcriptional activation is possibly the least well understood and studied. However, many important genes are activated by pRb, such as, TGF-B2, Il-6, the retinoblastoma gene itself, and cyclin D1, (Herwig & Strauss, 1997; Lania et al., 1997; Sellers & Kaelin, 1996; Tenen et al., 1997).

The Sp1 Transcription Factor Activates the hTR Promoter.

Figure 22:
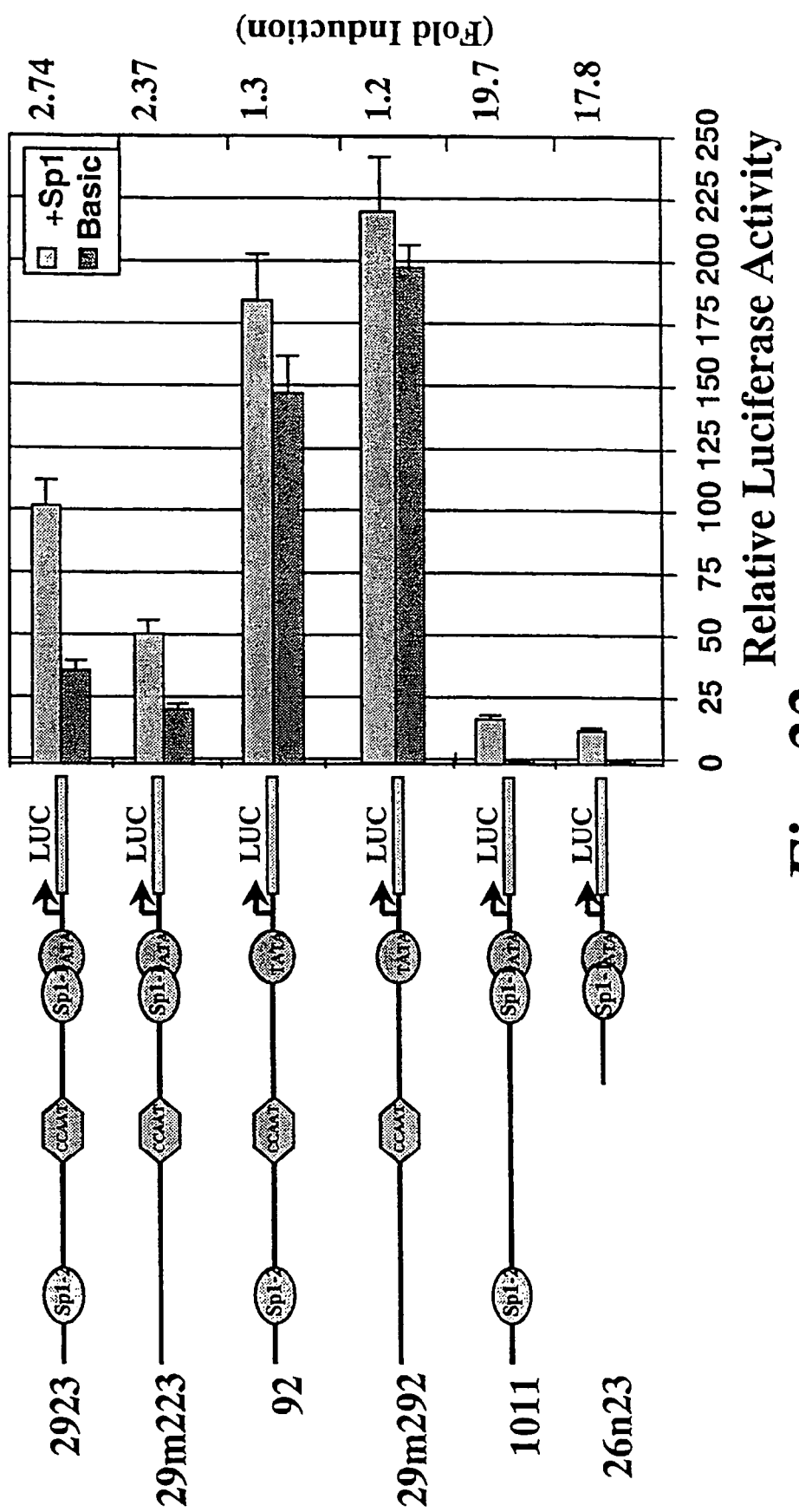
FIG. 22 shows Sp1 activation of the hTR promoter in 5637 cells. Left side shows mutant constructs, right side shows related luciferase activity, right column shows fold induction by Sp1.

The ability of the Sp1 transcription factor to modulate the hTR promoter was assessed by co-transfecting the hTR promoter constructs shown in FIG. 22, with an Sp1 expression vector. From FIG. 22 it can be seen that Sp1 is an activator of the hTR promoter.

The Sp3 Transcription Factor Represses the hTR Promoter.

Figure 23:
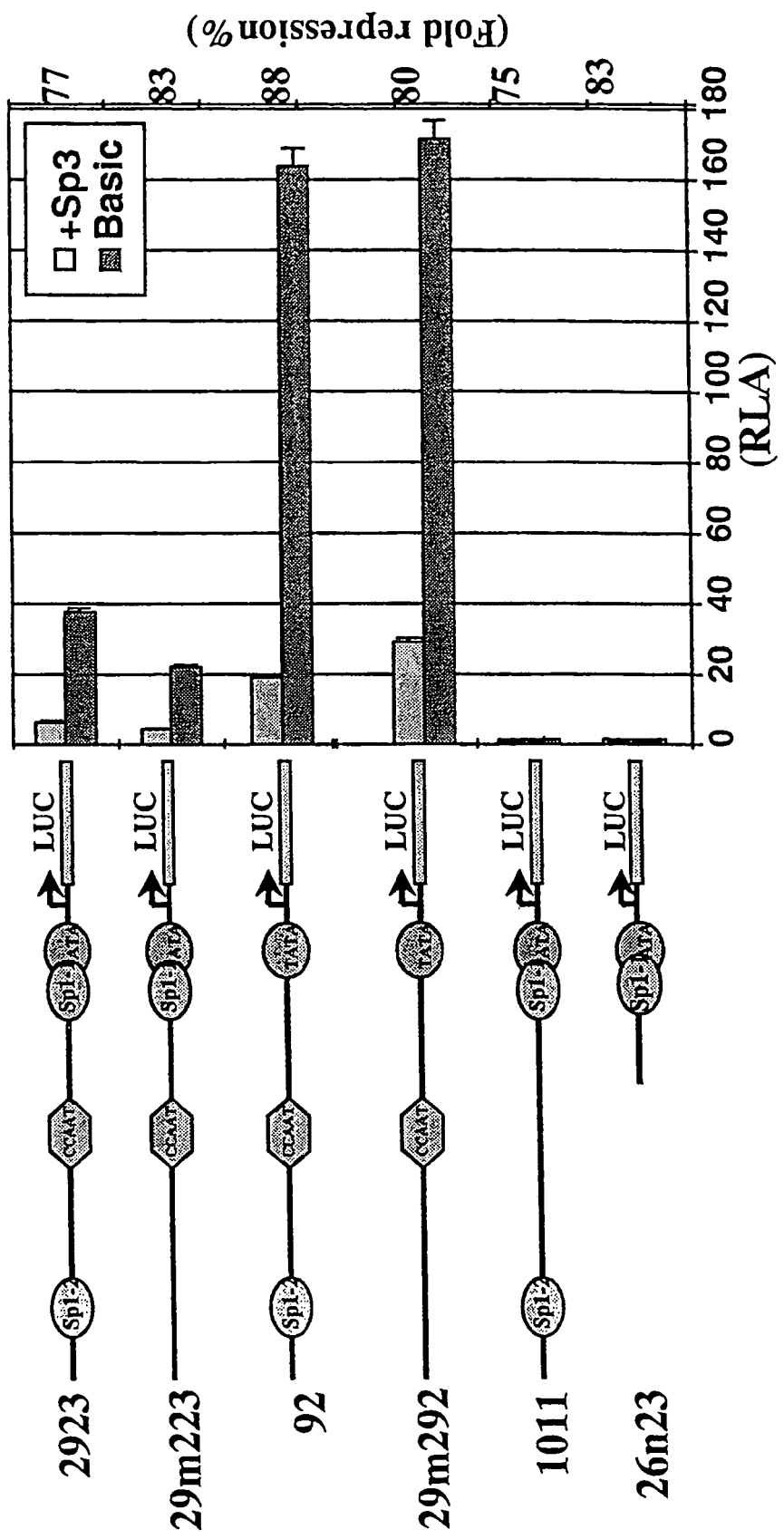
FIG. 23 shows Sp3 repression of the hTR promoter in 5637 cells. Left side shows mutant constructs, right side shows related luciferase activity, right column show fold repression by Sp3.

The ability of the Sp3 transcription factor to modulate the hTR promoter was assessed by co-transfecting the hTR promoter constructs shown in FIG. 23, with an Sp3 expression vector. From FIG. 23 it can be seen that Sp3 is an repressor of the hTR promoter.

The Retinoblastoma Gene Product, pRb, Activates the hTR Promoter

Figure 24:
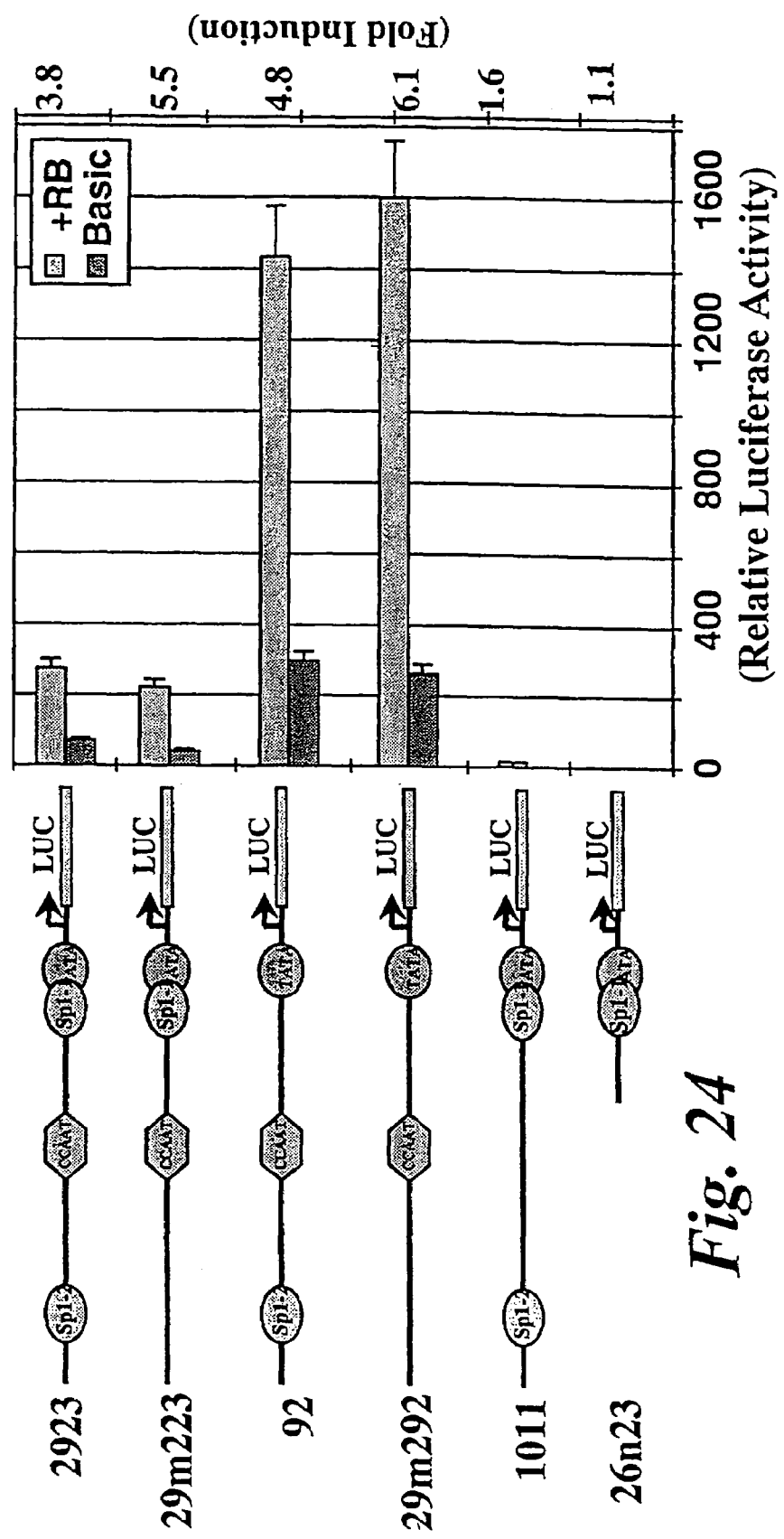
FIG. 24 concerns pRB interaction with Sp1 family and CCAAT factors. It shows activation of the hTR promoter in 5637 cells by the retinoblastoma gene product. Left side shows mutant constructs, right side shows related luciferase activity, right column shows fold induction by pRb.
Figure 25:
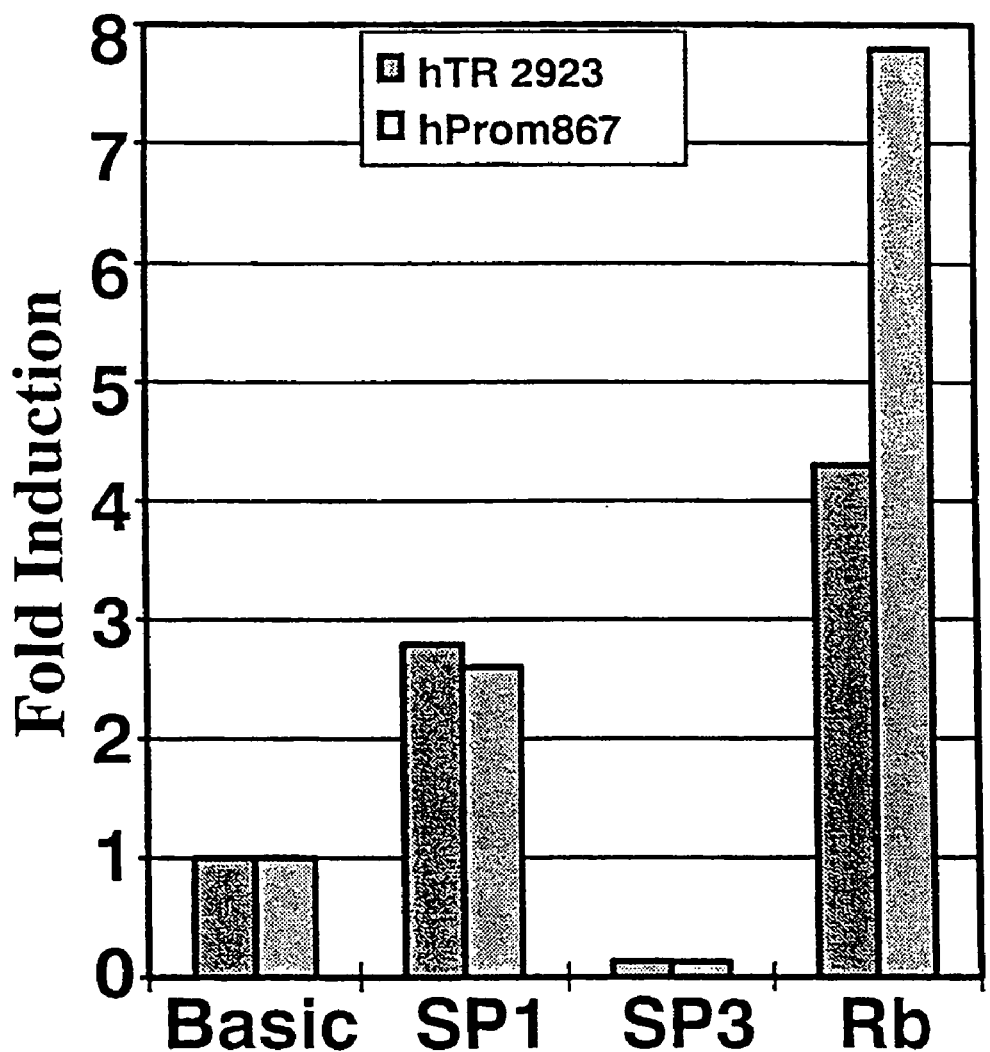
FIG. 25 shows a summary of the transcriptional regulation of the hTR gene promoter by Sp1, Sp3 and pRb. Two constructs were used, hTR 2923 and hProm867 as described in FIG. 18. Basic refers to the promoter activity of the constructs in the absence of Sp1, Sp3 or pRb. As can been seen, SP1 and Rb stimulate hTR gene expression and Sp3 supresses hTR gene expression to background.

The ability of the pRb to modulate the hTR promoter was assessed by co-transfecting the hTR promoter constructs shown in FIG. 24, with an pRb expression vector. From FIG. 24 it can be seen that pRb is an activator of the hTR promoter. For a summary of the above data see FIG. 25.

Genetically Directed Enzyme Prodrug Therapy (GDEPT).

The term "GDEPT" is used to include both viral and non-viral delivery systems. Examples of suitable vector systems include vectors based on the Molony murine leukaemia virus are known (Ram. Z et al, Cancer Research (1993) 53. 83–88; Dalton and Treisman, Cell (1992) 68. 597–612). These vectors contain the Murine Leukaemia virus (MLV) enhancer system cloned upstream at the β-globin minimal promoter. This vector further contains a polylinker to facilitate cloning, followed by the β-globin 3'-untranslated region and polyadenylation sites.

Suitable viral vectors further include those which are based upon a retrovirus. Such vectors are widely availbel in teh art, Culver et al (Science (1992) 256. 1550–1552) also describe the use of retroviral vectors in GDEPT. Such vectors or vectors derived from such vectors may also be used. Other retroviruses may also be used to make vectors suitable for use in the present invention. Such retroviruses include rous sarcoma virus (RSV). The promoters from such viruses may be used in vectors in a manner analogous to that described for MLV.

In general the vector may be any RNA or DNA vector used in VDEPT or GDEPT therapies.

The enzyme may be any enzyme which is not normally expressed in the surface of a cell, nor released into circulation, particularly a mammalian (especially human) cell, and which is capable of modifying or killing the target cell e.g. a cancer cell.

The enzyme may be linked to a signal sequence which directs the enzyme to the surface of a mammalian cell. This will usually be a mammalian signal sequence or a derivative thereof which retains the ability to direct the enzyme to the cell surface. This will be needed unless the enzyme has an endogenous signal sequence which does this. Even if the enzyme does have such a signal sequence, it can be replaced by another signal sequence where this is desirable or appropriate. Suitable signal sequences include those found in transmembrane receptor tyrosine kinases such as the c-erbB2 (HER2/neu) signal sequence or variants thereof which retain the ability to direct expression of the enzyme at the cell surface. The c-erbB2 signal sequence can be obtained by reference to Coussens et al (1985) Science. 230. 1132–1139.

The enzyme may be expressed at the surface of a cell. This means that it will be expressed in such a fashion as to have the enzyme exposed outside the cell so that it may interact with the prodrug, but will still be attached to the plasma membrane by virtue of a suitable plasma membrane anchor. A suitable anchor will be a polypeptide anchor which is expressed by the vector. For example, the enzyme which is linked to a sequence which is a transmembrane region which anchors the enzyme in the membrane of the cell. Such a transmembrane region can be derived from transmembrane receptor kinases, such as cerbB2, EGF receptors and CSF-1 receptors.

Vectors encoding the enzyme, together with, when required, a signal sequence and/or transmembrane region may be made using recombinant DNA techniques known per se in the art. The sequences encoding the enzyme, signal sequence and transmembrane regions may be constructed by splicing synthetic or recombinant nucleic acid sequences together, or by modifying existing sequences by techniques such as site directed mutagenesis. Reference may be made to "molecular cloning" by Sambrook et al (1989) Cold Spring Harbor) for discussion for standard recombinant DNA techniques.

The enzyme will be expressed in the vector using a promoter sequence or functional part thereof according to the present invention capable of activated in the cell to which the vector is targeted. The promoter sequence according to the present invention will be operably linked to the enzyme and its associated sequences. The promoter sequences according to the present invention may be modifed by techniques known in the art. Certain regions of the promoter sequence must be retained to ensure cell, e.g. tumour cell, specificity whereas other regions may be modified or delted without significant loss of specificity (see FIG. 5). The degree of regulation of such candidate promoter regions as described herein, can be tected and assessed by techniques known to those skilled in the art.

"Operably linked" refers to a juxtaposition wherein the promoter sequence and the enzyme-coding sequence are in a relationship permitting the coding sequence to be expressed under the control of the promoter sequence. Thus, there may be elements such as 5' non-coding sequence between the promoter sequence and coding sequence which is not native to either the promoter or nor the coding sequence. Such sequences can be included in the vector if they do not impair the correct control of the coding sequence by the promoter.

The vectors for use in GDEPT or VDEPT systems comprising the promoter sequence or functional fragment thereof in accordance with the present invention can be used in a method of treatment of the human or animal body. Such treatment includes a method of treating the growth of neoplastic cells which comprises administering to a patient in need of treatment the GDEPT or VDEPT systems. It is also possible that the vectors may be used to treat cells which are diseased through infection of the human or animal body by bacteria, viruses or parasites.

For use of the vectors in therapy, the vectors will usually be packaged into viral particles and the particles delivered to the site of the tumour, as described in for example Ram et al (ibid).

The viral particles maybe modified to include an antibody, fragment thereof (including a single chain) or tumour-directed ligand to enhance targetting of the tumour. Alternatively the vectors may be packaged into liposomes. The liposomes may be targeted to a particular tumour. This can be achieved by attaching a tumour-directed antibody to the liposome. Viral particles may also be incorporated into liposomes. The particles may be delivered to the tumour by any suitable means at the disposal of the physician. Preferably, the viral particles will be capable of selectively infecting the tumour cells. By "selectively infecting" it is meant that the viral particles will primarily infect tumour cells and that the proportion of non-tumour cells infected is such that the damage to non-tumour cells by administration of a prodrug will be acceptably low, given the nature of the disease being treated. Ultimately, this will be determined by the physician.

One suitable route of administration is by injection of the particles in a sterile solution. While it is possible for the prodrugs to be administered alone it is preferably to present them as pharmaceutical formulations. The formulations comprise a prodrug, together with one or more acceptable carriers thereof and optionally other therapeutic ingredients. The carrier or carriers must be "acceptable" in the sense of being compatible with the other ingredients of the formulation and not deleterious to the recipients thereof, for example, liposomes. Suitable liposomes include, for example, those comprising the positively charged lipid (N[1-(2,3-dioleyloxy)propyl]-N,N,N-triethylammonium (DOTMA), those comprising dioleoylphosphatidylethanolamine (DOPE), and those comprising 3β[N-(n'N'-dimethylaminoethane)-carbamoyl]cholesterol(DC-Chol).

Viruses, for example isolated from packaging cell 25' lines may also by administered by regional perfusion or direct intratumoral direction, or direct injection into a body cavity (intracaviterial administration), for example by intraperitoneum injection.

Formulations suitable for parenteral or intramuscular administration include aqueous and non-aqueous sterile injection solutions which may contain anti-oxidants, buffers, bacteriostats, bactericidal antibiotics and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose containers, for example sealed ampoules and vials, and may be stored in a freeze-dried (lyophilized) condition requiring only the addition of the sterile liquid carrier, for example water, for injections, immediately prior to use. Injection solutions and suspensions may be prepared extemporaneously from sterile powders, granules and tablets of the kind previously described.

It should be understood that in addition to the ingredients particularly mentioned above the formulations may include other agents conventional in the art having regard to the type of formulation in question. Of the possible formulations, sterile pyrogen-free aqueous and non-aqueous solutions are preferred.

The doses may be administered sequentially, eg. at daily, weekly or monthly intervals, or in response to a specific need of the patient. Preferred routes of administration are oral delivery and injection, typically parenteral or intramuscular injection or intratumoural injection.

In using the system of the present invention the prodrug will usually be administered following administration of the vector incorporating the promoter of the present invention and encoding an enzyme. Typically, the vector will be administered to the patient and then the uptake of the vector by transfected or infected (in the case of viral vectors) cells monitored, for example by recovery and analysis of a biopsy sample of targeted tissue.

The exact dosage regime will, of course, need to be determined by individual clinicians for individual patients and this, in turn, will be controlled by the exact nature of the prodrug and the cytotoxic agents to be released from the prodrug but some general guidance can be given. Chemotherapy of this type will normally involve parenteral administration of both the prodrug and modified virus and administration by the intravenous route is frequently found to be the most practical. For glioblastoma the route is often intratumoural. A typical dosage range of prodrug generally will be in the range of from about 1 to 150 mg per kg per patient per day, which may be administered in single or multiple doses. Preferably the dose range will be in the range from about 10 to 75, e.g. from about 10 to 40, mg per kg per patient per day. Other doses may be used according to the condition of the patient and other factors at the discretion of the physician.

Tumours which may be treated using the system of the present invention include any tumours capable or being treated by a GDEPT or VDEPT system and thus are not limited to any one particular class of tumours. Particularly suitable tumour types include breast, colorectal and ovarian tumours, as well as pancreatic, melanoma, glioblastoma, hepatoma, small cell lung, non-small cell lung, muscle and prostate tumours.

The system of the invention may also be used to treat infections diseases, for example, and any other condition which requires eradication of a population of cells.

It will be understood that where treatment of tumours is concerned, treatment includes any measure taken by the physician to alleviate the effect of the tumour on a patient. Thus, although complete remission of the tumour is a desirable goal, effective treatment will also include any measures capable of achieving partial remission of the tumour as well as a slowing down in the rate of growth of a tumour including metastases. Such measures can be effective in prolonging and/or enhancing the quality of life and relieving the symptoms of the disease.

Tumour Specific Gene Expression for Genetic Therapy Via Telomerase RNA Gene Promoters.

The present studies point to examples of clear differentials in hTR expression between cancerous and adjacent normal tissue which support the application of effective telomerase-based therapy. Indeed, the presence of high levels of hTR expression in specific cancers suggest the TR promoter may be an interesting focus for genetic therapies designed to target therapeutic genes to tumours, via tumour specific gene expression. Therefore, the present inventor provide use of the TR promoters to drive expression of enzyme-prodrug activation systems such as viral thymidine kinase and ganciclovir, although many other systems may also be used (see above). Targeted gene expression via the telomerase RNA gene promoter may also be used in gene replacement strategies for cancer therapy.

Figure 26:
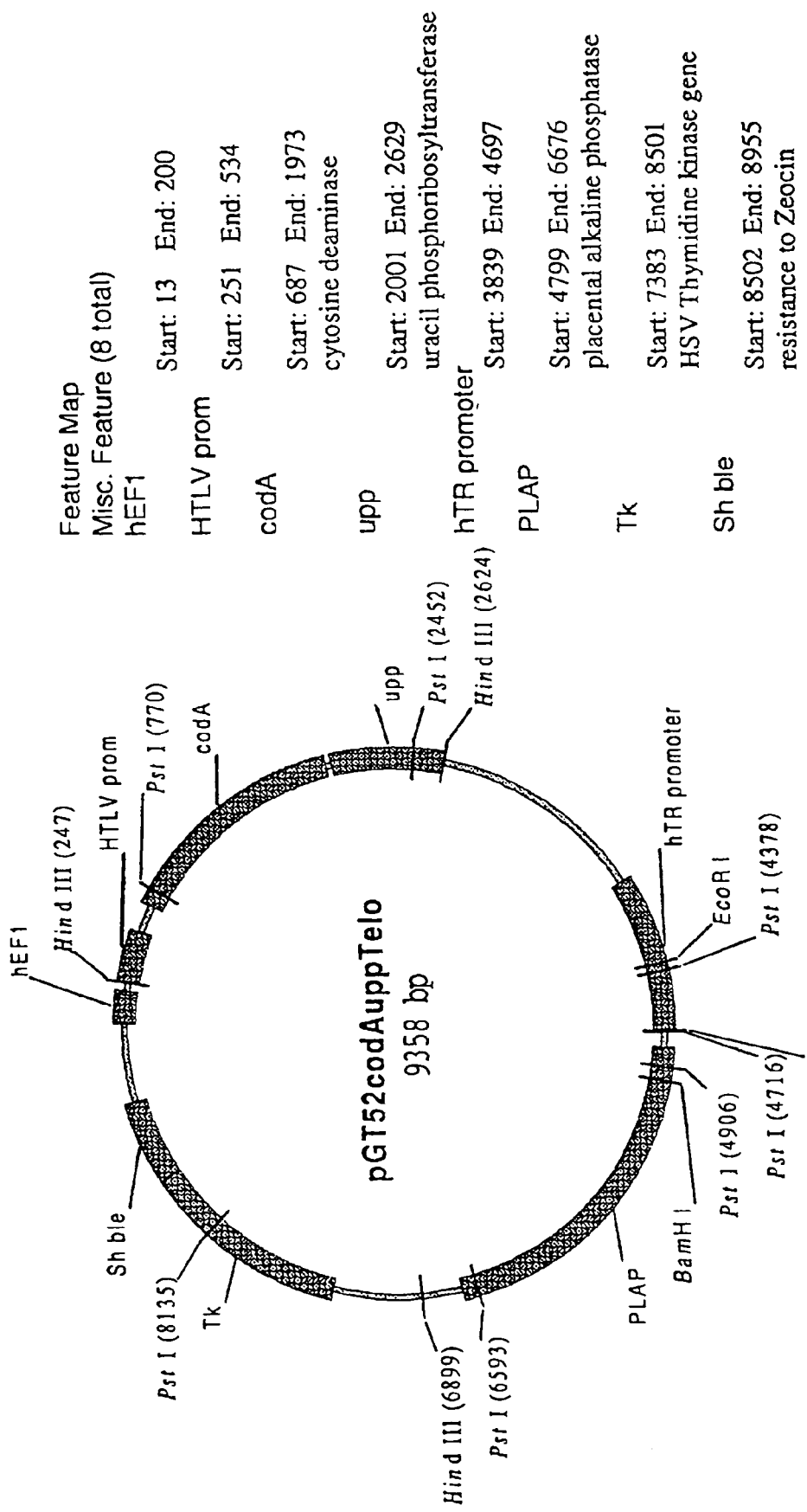
FIG. 26 shows a map of the hTR suicide gene vector pGT52-codAuppTelo and the genetic components of the vector.
Figure 27:
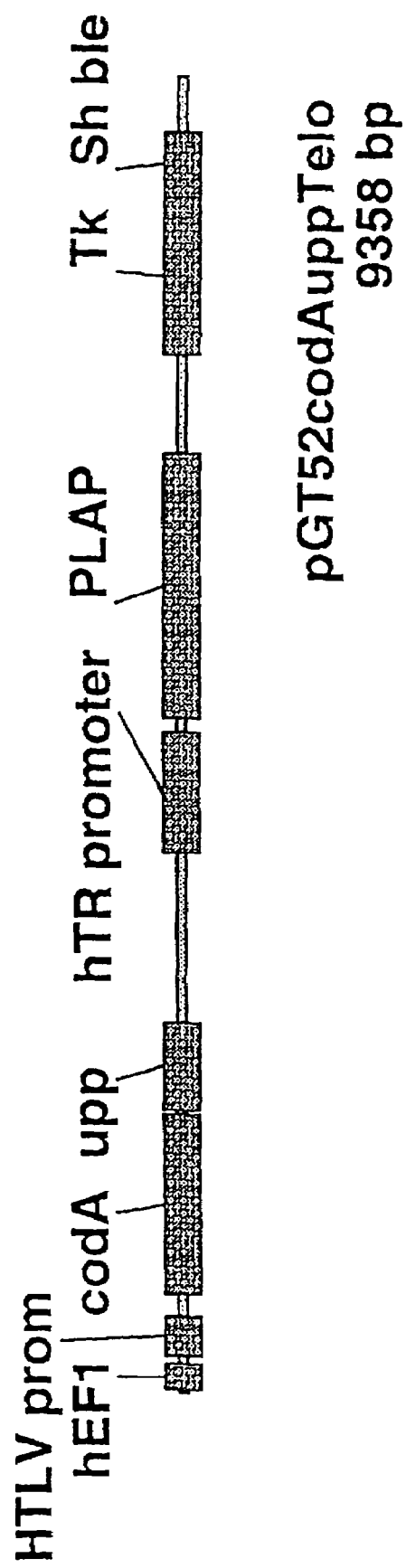
FIG. 27 shows details of the two transcriptional units of the hTR suicide gene vector pGT52-codAuppTelo. The pGT52-codAuppTelo vector consists of two transcriptional units. First Transcriptional Unit contains the following parts: hTR, telomerase RNA gene promoter; PLAP, Placental Alkaline Phosphatase reporter gene; Tk, HSV thymidine kinase conferring sensitivity to ganciclovir; Sh ble, Zeocin antibiotic resistance gene. Second Transcriptional Unit contains the following parts: hEF1-HTLV promoter, elongation factor 1a & part of HTLV promoter; codA::upp, bacterial cytosine deaminase & uracil phosphoribosytransferase conferring sensitivity to the drugs 5FU & 5-fluorocytosine.

To this end, the present invention provides a first generation suicide gene therapy vector using the hTR promoter sequence, namely pGT52-codAuppTelo, (FIGS. 26 & 27). The hTR promoter sequences used to generate pGT52-codAuppTelo are hProm867 as shown in FIG. 4a. These sequences were inserted into the commercially available gene therapy vector pGT62-codAupp, (Invivogen, San Diago, Calif., USA), in place of the CMV promoter sequences.

The pGT52-codAuppTelo vector consists of two transcriptional units. First Transcriptional Unit contains the following parts: hTR, telomerase RNA gene promoter; PLAP, Placental Alkaline Phosphatase reporter gene; Tk, HSV thymidine kinase conferring sensitivity to ganciclovir; Sh ble (*Streptoalloteichus hindustanus* bleomycin gene), Zeocin antibiotic resistance gene. Second Transcriptional Unit contains the following parts: hEF1-HTLV promoter, elongation factor 1a and part of HTLV promoter; codA::upp, bacterial cytosine deaminase and uracil phosphoribosytransferase conferring sensitivity to the drugs 5FU and 5-fluorocytosine.

Cells expressing the telomerase RNA gene will therefore activate the hTR promoter and cause expression of the HSV thymidine kinase gene, (Tk). Expression of the HSV Tk gene sensitises cells to the drug Ganciclovir. Thus, cells activating the hTR promoter in the suicide gene vector will be killed on exposure to Ganciclovir.

Materials and Methods

Site-Directed Mutagenesis and Constructs:

The PCR mutagenesis were performed separately by using Site-directed mutagenesis kit [Stratagene, QuikChange™]. The primers used for the construction of site-replaced mutants of the Sp1, CCAAT, RCE and TATA binding sites are shown in FIG. 12.

The PCR reactions were performed using the following standard condition; All PCRs were performed using 2 µl of pC2923 (−107/+69) plasmid DNA(50 ng/µl) as template, 1.5 mM MgCl$_2$, 0.2 mM dNTP's, 25 nM of site-replaced primer and 1.0 µl (2.5 U/µl) Pfu DNA polymerase in 50 µl reaction volume. A total of 16 cycles were used after originally denaturing at 95° C. for 30 seconds. In each cycle, the protocal was as follows:

30 seconds denaturing at 95° C.

30 seconds annealing at 55° C.

6 minutes elongation at 68° C. (2 minutes/Kb plasmid length)

Then, mutants of luciferase reporter construct were constructed by subcloning the mutation fragments into Xho I/Hind III linearized pGL3 Basic vector.

Annealing and Gel Purification of Oligonucleotides

To anneal the two complememtary oligonucleotides, the same molar ratio of oligonucleotides were mixed in TE buffer, the oligo was treated at 95° C. for 5 minutes in either the Perkin-Elmer Cetus DNA Thermal Cycler or the Perkin-Elmer Cetus Cycler 9600, then the Cycler was switched off to cool down slowly (about 4.5 hours). Then, the annealing oligo were loaded in the 12% PAGE gel and band excised. Finally, the pellet was resuspended in 25 ul TE and quantitated.

Preparation of Nuclear Cell Protein Extracts

Nuclear protein preparation: Approximately $10^{10}$ cells were washed in PBS and then twice with TMS (5 mM Tris-HCl pH 7.5, 2.5 mM $MgCl_2$, 125 mM sucrose). Cells were lysed in 200 ml of TMS plus 0.25% Triton X-100, and nuclei were harvested by centrifugation (1,600×g, 20 minutes). Nuclei were washed three times in 200 ml of TMS and resuspended in approximately 5 ml of TMS (5 to 10 mg of DNA per ml), and 0.1 volumes of 4 m NaCl was added dropwise with stirring. The solution was centrifuged at 10,000×g for 20 minutes and the supernatant was spun at 100,00×g for 60 minutes. Solid ammonium sulfate was added to 0.35 g/ml and left on ice for 30 minutes. The precipitate was pelleted at 10,000×g for 30 minutes and redissolved in 5 ml of E50 buffer (50 mM ammonium sulfate, 20 mM HEPES, pH 7.9, 5 mM $MgCl_2$, 0.1 mM EDTA, 0.1%[v/v] Brij 35, 20%[v/v] glycerol, 1 mM DTT) and dialyzed for 16 hours against 1 litter of storage buffer (50 mM NaCl, 20 mM HEPES, pH 7.9, 5 mM $MgCl_2$, 20%[v/v] glycerol, 1 mM DTT). The crude protein extract was cleared by centrifugation at 100.00×g for 60 minutes, and aliquots were stored at –70° C.

Electrophoresis Mobility Gel Shift Assay (EMSA)

Electrophoresis Mobility Shift Assay (EMSA) was performed by EMSA kit [Promega].

Typical 5'-kinase labeling reactions included the DNA to be labeled, [gg-$^{32}$P]dATP[Amersham], T4 polynucleotide kinase, and buffer [Promega]. Synthesized oligomers were 5'-end-labeled with [gg32P] dATP (5,000 mCi/mmol) and were used as probes in EMSA. 5.5 ug of Hela nuclear proteins were incubated in 15 ul of reaction containing 4% glycerol, 1 mM $MgCl_2$, 0.5 mM dithiothreitol(DTT), 0.5 mM EDTA, 50 mM NaCl, 10 mM Tris-HCl, pH7.5 and 2.0 ug poly(dI-dC), with or without excess molar of unlabeled DNA competitors, on ice for 10 min, followed by addition of 5,000–10,000 cpm of the probe. For competition experiments, nonradioactive double-stranded oligodeoxynucleotides were added in 100-fold molar excess prior to addition of the probe. For supershift assays, rabbit anti-human polyclonal antibodies specific against Sp1, Sp3, Rb, Ap-2 (Santa Cruz Biotechnology) were added to the reaction mixture 25 minutes prior to the addition of the probe. All DNA-protein complexes were resolved on 5% native polyacrylamide gels run in 22.3 mM Tris, 22.3 mM boric acid, and 0.5 mM EDTA. Visualization was performed using both a computing PhosphorImager with ImageQuant software analysis (Molecular Dynamics) and autoradiography on Kodak XAR-5 films.

SuperFect™ Transfection (OIAGEN)

For co-transfection of wild type (pL2930,107/+69) and each individual mutation luciferase reporter construct, 3 ug plasmid DNA was mixed with 3 ug of Sp1, or Sp3 (pCMVSp1 and pCMVSp3), or Sp1 plus Sp3, or pCMVb expression vector, 0.25 ug pRB(pCMV-pRb) was used for co-transfection. 7.5 µl Superfect™ Transfection Reagent [QIAGEN] was added to the DNA solution and mixed by pipetting up and down 5 times to get complexes.

DISCUSSION

In general, there are no significant sequence homologies between the promoter regions of the human and mouse telomerase RNA genes. Indeed, there is considerable debate as to whether telomere length is regulated in a similar fashion in humans and mouse (Blasco et al., 1997; Kipling, 1997a; Kipling, 1997b; Zakian, 1997). However, mouse models represent a valuable resource with which to study the role of telomerase in cellular senescence and tumour progression and mouse models are likely to be required to investigate new therapies based on telomerase inhibition. In addition, the developmental regulation of telomerase will be more easily approached in mice (Bestilny et al., 1996; Blasco et al., 1995; Blasco et al., 1997; Blasco et al., 1996; Broccoli et al., 1996; Prowse & Greider, 1995). Thus, any differences between the two species may in fact aid understanding of the function for telomerase in maintaining genome stability and will be important in developing good murine models for human disease or developmental processes.

Despite the lack of sequence similarity between the human and mouse telomerase RNA gene promoter regions, they both have consensus sites for the binding of transcription factors implicated in haematopoiesis and leukaemogenesis such as GATA-1, PU.1, PEA2/PEBP2, C/EBP, and c-Ets-2 (Tenen et al., 1997). This data will therefore be used in the detection of telomerase activity in normal and malignant haematopoietic cells (Bodnar et al., 1996; Cheng et al., 1997; Holt et al., 1997; Norrback & Roos, 1997; Pan et al., 1997). The human and mouse telomerase RNA genes do share an interesting similarity, in that they both lie in CpG islands, and thus their expression may be regulated by methylation. DNA methylation is thought to be important for gene regulation during normal development and cellular senescence, and abnormal methylation patterns may be a fundamental change in tumour progression (Baylin et al., 1991; Bird, 1996; Laird & Jaenisch, 1996; Vertino et al., 1994; Wilson & Jones, 1983). Thus it has been suggested that aberrant CpG island methylation during the normal ageing process, could contribute to immortalisation by interfering with expression of "mortality" genes, of which hTR and terc can be included (Vertino et al., 1994; Wilson & Jones, 1983).

Turning to the functional analysis of the cloned sequences, the minimal promoter for hTR resides within a region of 272 bp upstream of the published transcriptional start site, (Feng et al., 1995), (FIGS. 5a, 4a). There are a number of potential transcription factor binding sites in this region including consensus sequences for AP1, Sp1, PEA2/PEBP2, PEA3 and PU.1. Interestingly, the expression in the fos/jun family of proteins, which determine AP1 activity, are suppressed during the onset of senescence and would be predicted to lead to a reduction in AP1 activity in senescent cells (Campisi, 1997; Irving et al., 1992; Riabowol et al., 1992; Seshadri & Campisi, 1990). AP1 also responds to protein kinase C, and it has recently been demonstrated that hTR expression is induced by protein kinase C during T-cell activation (Bodnar et al., 1996). Extending the promoter region to 463 bp upstream of the transcriptional start site, increases the luciferase activity to its maximum level, (FIGS. 5a, 4a). This region contains several consensus binding sites for glucocorticoid/progesterone/androgen receptor binding, which may contribute to the maximal activity demonstrated by hProm505. A reduction in promoter activity is observed on extending the promoter fragments to include more 5'-sequence, (FIG. 5a), suggesting that sequences towards the 5'-end of the clone may influence promoter activity in a negative fashion.

The minimal promoter for terc resides in a 94 bp region upstream of the published transcriptional start site, (Blasco et al., 1995), (FIGS. 5b, 4b). A striking feature of this region is the presence of three AP-2 consensus sites, two of which are coupled to c-Ets-2 sites and all these elements are contained in the 73 bp region required for promoter activity, (FIGS. 5b, 4b). Oncogenic Ras gene signalling has been shown to operate through c-Ets-2 binding sites, thus there is a testable relationship between oncogene activation during tumour progression and telomerase RNA gene transcriptional activity (Galang et al., 1994; Wasylyk et al., 1994). A reduction in promoter activity is observed on extending the promoter fragments to include more 5'-sequence, (FIG. 5b, mProm628), suggesting that sequences towards the 5'-end of the clone may influence promoter activity in a negative fashion.

In summary, the present inventor has provided the art with DNA sequence elements and gene products which regulate the hTR promoter. Thus, the inventor has identified the first direct molecular controls on signal transduction pathways affecting telomerase expression. The major findings are firstly, that the retinoblastoma gene product stimulates hTR promoter activity; secondly, that the Sp1 transcription factor stimulates hTR promoter activity; thirdly, that the Sp3 transcription factor is a potent repressor of hTR promoter activity; fourthly that mutation of the hTR CCAAT sequence elements abrogates promoter activity; and fifthly, that the hTR Sp1-1 sequence element is a site for a repressor of hTR promoter activity.

These studies show that alterations in the amounts or activities of Sp1/Sp3/pRb/CCAAT factors in a cell or signal transduction specific manner may contribute to hTR gene expession. Further, these studies provide evidence for the signal transduction pathways which may be operating in normal cells to regulate hTR gene expression. They provide a focus for studies designed to uncover how cancer cells reactivate or upregulate hTR gene expression. Transcription factors complexes on the hTR promoter as provided herein offer direct targets for developing inhibitory or gene-mimetic molecules, and assays for screening for them. The understanding of the molecular basis for hTR gene regulation will be of value in the manipulation of telomerase expression, for example, in age related disease or optimal extension of cellular lifespan of commercially useful cells. These studies further provide insight into the regulation of other components of the telomerase enzyme, for example, the protein component, hTERT.

REFERENCES

Avilion, A. A., Piatyszek, M. A., Gupta, J., Shay, J. W., Bacchetti, S. & Greider, C. W. (1996). *Cancer Research*, 56, 645–650.

Baylin, S. B., Makos, M., Wu, J., Yen, R. W., De, B. A., Vertino, P. & Nelkin, B. D. (1991). *Cancer Cells*, 3, 383–390.

Benda, J. A. (1994). Semin. In Oncol., 21, 3–11.

Bestilny, L. J., Brown, C. B., Miura, Y., Robertson, L. D. & Riabowol, K. T. (1996). *Cancer Research*, 56, 3796–3802.

Bird, A. P. (1996). *Cancer Surveys*, 28.

Blasco, M. A., Funk, W., Villeponteau, B. & Greider, C. W. (1995). *Science*, 269, 1267–1270.

Blasco, M. A., Lee, H., Hande, M. P., Samper, E., Lansdorp, P. M., DePinho, R. A. & Greider, C. W. (1997). *Cell*, 91, 25–34.

Blasco, M. A., Rizen, M., Greider, C. W. & Hanahan, D. (1996). *Nature Genetics*, 12, 200–204.

Bodnar, A. G., Kim, N. W., Effros, R. B. & Chiu, C. P. (1996). *Experimental Cell Research*, 228, 58–64.

Breslow, R. A., Shay, J. W., Gazdar, A. F. T. and Srivastava S., (1997). J. Natl. Cancer Inst., 89, 618–623.

Broccoli, D., Chong, L., Oelmann, S., Fernald, A. A., Marziliano, N., Van, S. B., Kipling, D., Le, B. M. M. & De, L. T. (1997). *Human Molecular Genetics*, 6, 69–76.

Broccoli, D., Godley, L. A., Donehower, L. A., Varmus, H. E. & De, L. T. (1996). *Molecular & Cellular Biology*, 16, 3765–3772.

Bryan, T. M., Marusic, L., Bacchetti, S., Namba, M. & Reddel, R. R. (1997). *Human Molecular Genetics*, 6, 921–926.

Burger, A. M., et al (1997). Br. J. Cancer, 75, 516–522.

Cai, W., Hu, L. & Foulkes, J. G. (1996). *Current Opinion in Biotechnology*, 7, 608–615.

Campisi, J. (1997). *European Journal of Cancer Part A*, 33, 703–709.

Cheng, A. J., Liao, S. K., Chow, S. E., Chen, J. K. & Wang, T. C. (1997). *Biochemical & Biophysical Research Communications*, 237, 438–444.

Connors, T. A. (1995). *Gene Therapy*, 2, 702–709.

Feng, J., Funk, W. D., Wang, S. S., Weinrich, S. L., Avilion, A. A., Chiu, C. P., Adams, R. R., Chang, E., Allsopp, R. C., Yu, J., Le, S., West, M. D., Harley, C. B., Andrews, W. H., Greider, C. W. & Villeponteau, B. (1995). *Science*, 269, 1236–1241.

Galang, C. K., Der, C. J. & Hauser, C. A. (1994). *Oncogene*, 9, 2913–2921.

Gardiner-Garden, M. & Frommer, M. (1987). *Journal of Molecular Biology*, 196, 261–282.

Harley, C. B. and Villeponteau, B. (1995), Curr. Opin. Genet. Develop., 5, 249–255.

Herwig, S. Et al (1997). Eur. J. Biochem, 246, 581–601

Hiyama, E., et al (1996). J. Natl. Cancer Inst., 88, 116–122.

Hiyama, E., et al (1995a). Nature Med., 1, 249–255.

Hiyama, K., et al (1995b). J. Nl. Cancer Inst., 87, 895–902.

Holt, S. E., Wright, W. E. & Shay, J. W. (1997). *European Journal of Cancer Part A*, 33, 761–766.

Holt, S. E., Shay, J. W. and Wright W. E. (1996a). Nature Biotech., 14, 836–839.

Holt, S. E., et al (1996b). Mol. Cell. Biol., 16, 2932–2939.

Irving, J., Feng, J., Wistrom, C., Pikaart, M. & Villeponteau, B. (1992). *Experimental Cell Research*, 202, 161–166.

Kim, N. W. (1997). *European Journal of Cancer Part A*, 33, 781–786.

Kim, N. W., et al (1994) Science 266, 2011–2015.

Klingelhutz, A. J. et al (1996). Nature, 380, 79–82.

Kipling, D. (1997a). *Human Molecular Genetics*, 6, 1999–2004.

Kipling, D. (1997b). *European Journal of Cancer Part A*, 33, 792–800.

Kuniyasu, H., Domen, T., Hamamoto, T., Yokozaki, H., Yasui, W., Tahara, H. & Tahara, E. (1997). *Japanese Journal of Cancer Research*, 88, 103–107.

Laird, P. W. & Jaenisch, R. (1996). *Annual Review of Genetics*, 30.

Lania, L. et al (1997). Int. J. Biochem. Cell Biol. 29, 1313–1323.

Li, H., Zhao, L. L., Funder, J. W. & Liu, J. P. (1997). *Journal of Biological Chemistry*, 272, 16729–16732.

Lundbiad, V. and Wright, W. E. (1996). Cell, 87, 369–375.

Mandal, M. & Kumar, R. (1997). *Journal of Biological Chemistry*, 272, 14183–14187.

Miller, N. & Whelan, J. (1997). *Human Gene Therapy*, 8, 803–815.

Morin, G. B. (1996). Seminars in Cell and Developmental Biology, 7, 5–13.

Morin, G. B. (1997). *European Journal of Cancer Part A*, 33, 750–760.

Nakamura, T. M., Morin, G. B., Chapman, K. B., Weinrich, S. L., Andrews, W. H., Lingner, J., Harley, C. B. & Cech, T. R. (1997). *Science*, 277, 955–959.

Norrback, K. F. & Roos, G. (1997). *European Journal of Cancer Part A*, 33, 774–780.

Pan, C., Xue, B. H., Ellis, T. M., Peace, D. J. & Diaz, M. O. (1997). *Experimental Cell Research*, 231, 346–353.

Parkinson, E. K. et al. (1997), Euro. J. Cancer 33, 727–734.

Peterson, M. G. & Baichwal, V. R. (1993). *Trends in Biotechnology*, 11, 11–18.

Prowse, K. R. & Greider, C. W. (1995). *Proceedings of the National Academy of Sciences of the United States of America*, 92, 4818–4822.

Raymond, E. et al (1996) Curr. Opin. Biothech., 7, 583–591.

Riabowol, K., Schiff, J. & Gilman, M. Z. (1992). *Proceedings of the National Academy of Sciences of the United States of America*, 89, 157–161.

Seller, W. R. et al (1996). Biochim. Biophys. Acta, 1288, M1–5.

Seshadri, T. & Campisi, J. (1990). *Science*, 247, 205–209.

Sharma, S., Raymond, E., Soda, H., Sun, D., Hilsenbeck, S. G., Sharma, A., Izbicka, E., Windle, B. & Von Hoff, D. D. (1997). *Annals of Oncology*, 8, 1063–1074.

Shay, J. W. & Bacchetti, S. (1997). *European Journal of Cancer Part A*, 33, 787–791.

Shay J. W. & Wright W. E. (1996). Current Opinion in Oncology 8 66–71.

Soder, A. I., Going, J. J., Kaye, S. B. & Keith, W. N. (1997a). *Oncogene*, in press.—16 979–983 (1998)

Soder, A. I., Hoare, S. F., Muir, S., Going, J. J., Parkinson, E. K. & Keith, W. N. (1997b). *Oncogene*, 14, 1013–1021.

Soder, A. I., Hoare, S. F., Muire, S., Balmain, A., Parkinson, E. K. & Keith, W. N. (1997c). *Genomics*, 41, 293–294.

Tenen, D. G., Hromas, R., Licht, J. D. & Zhang, D. E. (1997). *Blood*, 90, 489–519.

Vertino, P. M., Issa, J. P., Pereira-Smith, O. M. & Baylin, S. B. (1994). *Cell Growth & Differentiation*, 5, 1395–1402.

Villeponteau, B. (1996). Seminars in Cell and Developmental Biology 7, 15–21.

Wasylyk, C., Maira, S. M., Sobieszczuk, P. & Wasylyk, B. (1994). *Oncogene*, 9, 3665–3673.

Wellinger, R. J. & Sen, D. (1997). *European Journal of Cancer Part A*, 33, 735–749.

Wilson, V. L. & Jones, P. A. (1983). *Science*, 220, 1055–1057.

Wright, W. E., Piatyszek, M. A., Rainey, W. E., Byrd, W. & Shay, J. W. (1996). *Developmental Genetics*, 18, 173–179.

Yashima, K. Piatyszek M. A. Saboorian H. M. Virmani A. K. Brown D. Shay J. W. and Gazdar A. F. (1997). J. Clin. Path., 50, 110–117.

Zakian, V. A. (1997). *Cell*, 91, 1–3.

Zhao, J. Q. et al (1998) Oncogene 16 1345–1350.

---

The invention claimed is:

1. An isolated promoter sequence for the human telomerase RNA (hTR) gene, consisting of SEQ ID NO: 36, or a sequence having 95% homology with SEQ ID NO: 36, said sequence or functional fragment initiating transcription of DNA operably linked downstream of said promoter sequence.

2. An isolated promoter sequence, hProm505, consisting of nucleotides 422 to 867 of SEQ ID NO: 36 or a sequence having 95% homology therewith.

3. The isolated promoter sequence according to claim 1 wherein the promoter sequence is construct hProm867 SEQ ID NO: 36.

4. The isolated promoter sequence according to claim 1 or claim 2 operably linked to a heterologous nucleic acid coding sequence.

5. A nucleic acid construct comprising the promoter sequence according to claim 1 or claim 2, operably linked to a heterologous gene.

6. The nucleic acid construct according to claim 5, wherein the heterologous gene encodes a cytotoxin.

7. A vector comprising the isolated promoter sequence according to claim 1 or claim 2.

8. An isolated host cell comprising the isolated promoter sequence according to claim 1 or claim 2.

9. An isolated host cell comprising the nucleic acid construct according to claim 5.

10. An isolated host cell comprising the nucleic acid construct according to claim 6.

11. An isolated promoter sequence hProm697, consisting of nucleotides 170 to 867 of SEQ ID NO: 36 or a sequence having 95% homology therewith.

12. An isolated promoter sequence hProm341, consisting of nucleotides 527 to 867 of SEQ ID NO: 36 or a sequence having 95% homology therewith.

13. The nucleic acid construct according to claim 5, wherein the heterologous gene encodes an enzyme capable of converting a prodrug to an active compound.

14. An isolated promoter sequence for the human telomerase RNA (hTR) gene, comprising construct hProm697, nucleotides 170 to 867 of SEQ ID NO: 36, said promoter sequence initiating transcription of DNA operably linked downstream of said promoter sequence.

15. The isolated promoter sequence according to claim 14, wherein the promoter sequence comprises construct hProm867 (SEQ ID NO: 36).

16. The isolated promoter sequence according to claim 14 operably linked to a heterologous nucleic acid coding sequence.

17. A nucleic acid construct comprising the promoter sequence according to claim 15, operably linked to a heterologous gene.

18. An isolated host cell comprising the promoter sequence of claim 14.

19. An isolated host cell comprising the sequence of claim 16.

20. An isolated host cell comprising the sequence of claim 17.

* * * * *

UNITED STATES PATENT AND TRADEMARK OFFICE
CERTIFICATE OF CORRECTION

PATENT NO. : 7,084,267 B1 Page 1 of 1
APPLICATION NO. : 09/601267
DATED : August 1, 2006
INVENTOR(S) : William Nicol Keith It is certified that error appears in the above-identified patent and that said Letters Patent is hereby corrected as shown below:

On the Title Page, Item (73) should read
Assignee: The University Court of the University of Glasgow
   Glasgow, United Kingdom Signed and Sealed this Twenty-third Day of September, 2008

JON W. DUDAS
*Director of the United States Patent and Trademark Office*